(12) United States Patent
Sharma et al.

(10) Patent No.: US 7,456,184 B2
(45) Date of Patent: Nov. 25, 2008

(54) MELANOCORTIN RECEPTOR-SPECIFIC COMPOUNDS

(75) Inventors: Shubh D. Sharma, Cranbury, NJ (US); Yi-Qun Shi, East Brunswick, NJ (US); Zhijun Wu, Plainsboro, NJ (US); Ramesh Rajpurohit, Hillsboro, NJ (US); Annette M. Shadiack, Somerset, NJ (US); Papireddy Purma, Plainsboro, NJ (US); Kevin D. Burris, Washington Crossing, PA (US)

(73) Assignee: Palatin Technologies Inc., Cranbury, NJ (US)

( * ) Notice: Subject to any disclaimer, the term of this patent is extended or adjusted under 35 U.S.C. 154(b) by 611 days.

(21) Appl. No.: 10/837,519

(22) Filed: Apr. 30, 2004

(65) Prior Publication Data

US 2004/0224957 A1    Nov. 11, 2004

Related U.S. Application Data

(60) Provisional application No. 60/546,393, filed on Feb. 19, 2004, provisional application No. 60/467,442, filed on May 1, 2003.

(51) Int. Cl.
    A61K 31/497    (2006.01)
    C07D 403/02    (2006.01)
(52) U.S. Cl. .................................. 514/254.09; 544/373
(58) Field of Classification Search ................. 544/373; 514/254.09
    See application file for complete search history.

(56) References Cited

U.S. PATENT DOCUMENTS

| | | | |
|---|---|---|---|
| 4,148,923 A | 4/1979 | Giudicelli et al. | |
| 4,239,763 A | 12/1980 | Milavec et al. | |
| 4,626,549 A | 12/1986 | Molloy et al. | |
| 4,680,289 A | 7/1987 | Applezweig | |
| 4,711,957 A | 12/1987 | Lai | |
| 4,766,125 A | 8/1988 | Van Daele et al. | |
| 4,937,267 A | 6/1990 | Holloway et al. | |
| 4,943,578 A | 7/1990 | Naylor et al. | |
| 4,968,684 A | 11/1990 | Van Daele et al. | |
| 4,997,836 A | 3/1991 | Sugihara et al. | |
| 5,120,713 A | 6/1992 | Mugica | |
| 5,292,726 A | 3/1994 | Ashton et al. | |
| 5,344,830 A | 9/1994 | Mills et al. | |
| 5,348,955 A | 9/1994 | Greenlee et al. | |
| 5,464,788 A | 11/1995 | Bock et al. | |
| 5,550,131 A | 8/1996 | Sugihara et al. | |
| 5,574,031 A | 11/1996 | Abramo et al. | |
| 5,599,809 A | 2/1997 | Hickey et al. | |
| 5,672,602 A | 9/1997 | Burkholder et al. | |
| 5,736,539 A | 4/1998 | Graham et al. | |
| 5,753,445 A | 5/1998 | Fillit et al. | |
| 5,753,653 A | 5/1998 | Bender et al. | |
| 5,798,359 A | 8/1998 | Shue et al. | |
| 5,804,578 A | 9/1998 | Chakravarty et al. | |
| 5,856,326 A | 1/1999 | Anthony et al. | |
| 5,968,938 A | 10/1999 | Williams et al. | |
| 6,020,334 A | 2/2000 | Fukushi et al. | |
| 6,033,656 A | 3/2000 | Mikami et al. | |
| 6,127,424 A | 10/2000 | Martin et al. | |
| 6,140,354 A | 10/2000 | Dax et al. | |
| 6,162,805 A | 12/2000 | Hefti | |
| 6,191,117 B1 | 2/2001 | Kozachuk | |
| 6,207,665 B1 | 3/2001 | Bauman et al. | |
| 6,207,699 B1 | 3/2001 | Rothman | |
| 6,214,831 B1 | 4/2001 | Yokoo et al. | |
| 6,294,539 B1 | 9/2001 | Lou et al. | |
| 6,316,470 B1 | 11/2001 | Kover et al. | |
| 6,350,760 B1 | 2/2002 | Bakshi et al. | |
| 6,372,747 B1 | 4/2002 | Taveras et al. | |
| 6,376,509 B1 | 4/2002 | Bakshi et al. | |
| 6,410,548 B2 | 6/2002 | Nargund et al. | |
| 6,432,959 B1 | 8/2002 | Cooper et al. | |
| 6,458,790 B2 | 10/2002 | Palucki et al. | |
| 6,469,006 B1 | 10/2002 | Blair et al. | |

(Continued)

FOREIGN PATENT DOCUMENTS

WO    WO 98/10653    3/1998

(Continued)

OTHER PUBLICATIONS

Adan, Roger A., et al., "Identification of Antagonist for Melanocortin MC3, MC4, and Mc5 Receptors", *European Journal of Pharmacology, Section 269* (1994), (1994),331-337.

(Continued)

*Primary Examiner*—James O. Wilson
*Assistant Examiner*—Ebenezer Sackey
(74) *Attorney, Agent, or Firm*—Morgan, Lewis & Bockius LLP

(57) ABSTRACT

A melanocortin receptor-specific compound of the general formula of structure I:

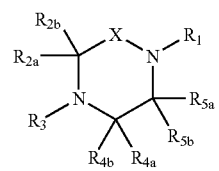

where X, $R_1$, $R_{2a}$, $R_{2b}$, $R_3$, $R_{4a}$, $R_{4b}$, $R_{5a}$ and $R_{5b}$ are as defined in the specification, which compound binds with high affinity to one or more melanocortin receptors and is optionally an agonist, an antagonist, an inverse agonist or an antagonist of an inverse agonist, and may be employed for treatment of one or melanocortin receptor-associated conditions or disorders, and methods for the use of the compounds of the invention.

15 Claims, 4 Drawing Sheets

U.S. PATENT DOCUMENTS

| | | |
|---|---|---|
| 6,472,398 B1 | 10/2002 | Palucki et al. |
| 6,486,165 B2 | 11/2002 | Zhang et al. |
| 6,531,476 B1 | 3/2003 | Heymans et al. |
| 6,534,503 B1 | 3/2003 | Dines et al. |
| 6,534,509 B1 | 3/2003 | Bauman et al. |
| 6,555,537 B2 | 4/2003 | Bauman et al. |
| 6,569,861 B2 | 5/2003 | Bakthavatchalam et al. |
| 6,579,968 B1 | 6/2003 | Blood et al. |
| 6,699,873 B1 | 3/2004 | Maguire et al. |
| 6,734,175 B2 | 5/2004 | Hadcock et al. |
| 2001/0018075 A1 | 8/2001 | Shigeyuki et al. |
| 2001/0047001 A1 | 11/2001 | Varkhedkar et al. |
| 2002/0004512 A1 | 1/2002 | Bakshi et al. |
| 2002/0010182 A1 | 1/2002 | Masaaki et al. |
| 2002/0032238 A1 | 3/2002 | Priepke et al. |
| 2002/0037837 A1 | 3/2002 | Takada et al. |
| 2002/0052383 A1 | 5/2002 | Bakthavatchalam et al. |
| 2002/0065277 A1 | 5/2002 | Hadcock et al. |
| 2002/0072604 A1 | 6/2002 | Carpino et al. |
| 2002/0082263 A1 | 6/2002 | Lou et al. |
| 2002/0107253 A1 | 8/2002 | Koh et al. |
| 2002/0107255 A1 | 8/2002 | Blimberg et al. |
| 2002/0128270 A1 | 9/2002 | Neya et al. |
| 2002/0137664 A1 | 9/2002 | Bakshi et al. |
| 2002/0143141 A1 | 10/2002 | Chen et al. |
| 2002/0173512 A1 | 11/2002 | Moltzen et al. |
| 2002/0177598 A1 | 11/2002 | Bauman et al. |
| 2002/0183316 A1 | 12/2002 | Pan et al. |
| 2003/0004162 A1 | 1/2003 | Treadway |
| 2003/0013721 A1 | 1/2003 | Meghani et al. |
| 2003/0040520 A1 | 2/2003 | Guzi et al. |
| 2003/0055247 A1 | 3/2003 | Cosford et al. |
| 2003/0060473 A1 | 3/2003 | Neya et al. |
| 2003/0069169 A1 | 4/2003 | Macor et al. |
| 2003/0083228 A1 | 5/2003 | Carpino et al. |
| 2003/0083335 A1 | 5/2003 | Hayward |
| 2003/0092732 A1 | 5/2003 | Yu et al. |
| 2003/0096827 A1 | 5/2003 | Yu et al. |
| 2003/0105106 A1 | 6/2003 | Chiang et al. |
| 2003/0109556 A1 | 6/2003 | Mazur et al. |
| 2003/0125334 A1 | 7/2003 | Chiang et al. |
| 2003/0139425 A1 | 7/2003 | Bauman et al. |
| 2003/0144277 A1 | 7/2003 | DeLucca |
| 2003/0149019 A1 | 8/2003 | Bremberg et al. |
| 2003/0158205 A1 | 8/2003 | Baumann et al. |
| 2003/0158209 A1 | 8/2003 | Dyke et al. |
| 2003/0166637 A1 | 9/2003 | Lehmann-Lintz et al. |
| 2003/0181441 A1 | 9/2003 | Mcclure et al. |
| 2003/0191136 A1 | 10/2003 | Bakthavatchalam et al. |
| 2003/0195212 A1 | 10/2003 | Lundstedt et al. |
| 2004/0024211 A1 | 2/2004 | Boyce et al. |
| 2004/0053933 A1 | 3/2004 | Pontillo et al. |

FOREIGN PATENT DOCUMENTS

| | | |
|---|---|---|
| WO | WO 00/05373 | 2/2000 |
| WO | WO 01/21647 | 3/2000 |
| WO | WO 00/40247 | 7/2000 |
| WO | WO 00/74679 | 12/2000 |
| WO | WO 01/10842 | 2/2001 |
| WO | WO 01/12176 | 2/2001 |
| WO | WO 01/18210 | 3/2001 |
| WO | WO 01/21634 | 3/2001 |
| WO | WO 01/23392 | 4/2001 |
| WO | WO 01/30343 | 5/2001 |
| WO | WO 02/00259 | 6/2001 |
| WO | WO 01/55106 | 8/2001 |
| WO | WO 01/55107 | 8/2001 |
| WO | WO 01/55109 | 8/2001 |
| WO | WO 01/91752 | 12/2001 |
| WO | WO 02/00654 | 1/2002 |
| WO | WO 02/12178 | 2/2002 |
| WO | WO 02/18437 | 3/2002 |
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/70511 | 9/2002 |
| WO | WO 02/079146 | 10/2002 |
| WO | WO 02/079203 | 10/2002 |
| WO | WO 02/081443 | 10/2002 |
| WO | WO 02/085925 | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 | 2/2003 |
| WO | WO 03/066587 | 2/2003 |
| WO | WO 03/020724 | 3/2003 |
| WO | WO 03/031410 | 4/2003 |
| WO | WO 03/053927 | 7/2003 |
| WO | WO 03/061660 | 7/2003 |
| WO | WO 03/092690 | 11/2003 |
| WO | WO 03/093234 | 11/2003 |

OTHER PUBLICATIONS

Adan, Roger A., et al., "Inverse Agonism Gains Weight", *Trends in Pharmacological Sciences*, vol. 24 No. 6, (Jun. 2003),315-321.

Door, Robert T., et al., "Evaluation of Melanotan-II, A Superpotent Cyclic Melanotropic Peptide in a Pilot Phase Clinical Study", *Life Science*, vol. 58, No. 20 (1996),1777-1784.

Grant, G A., "Synthetic Peptides: A Users Guide", *GA Grant, editor, W.H. Freeman & Co.*, New York 1992, (1992),11-24.

Hadley, M E., et al., "Discovery and Development of Novel Melanogenic Drugs: Melanotan-I and -II", Ronald. T. Borchardt, et al. editors; *Intergration of Pharmaceutical Discovery and Development: Case Histories, Plenum Press*, New York (1998), (1998),575-595.

Hruby, V J., et al., "Emerging Approaches in the Molecular Design of Receptor-Selective Peptide Ligands: Conformational, Topographical and Dynamic Considerations", *Biochemical Journal*, (1990) 268, (1990),249-262.

Mitsunobu, Oyo, "The Use of Diethyl Azodicarboxylate and Triphenylphosphine in Synthesis and Transformation of Natural Products", *Synthesis* vol. 1, (1981),1-28.

Toniolo, C, "Conformationally Restricted Peptides Through Short-Range Cyclizations", *International Journal Peptide Protein Research*, 35, (1990), (1990),287-300.

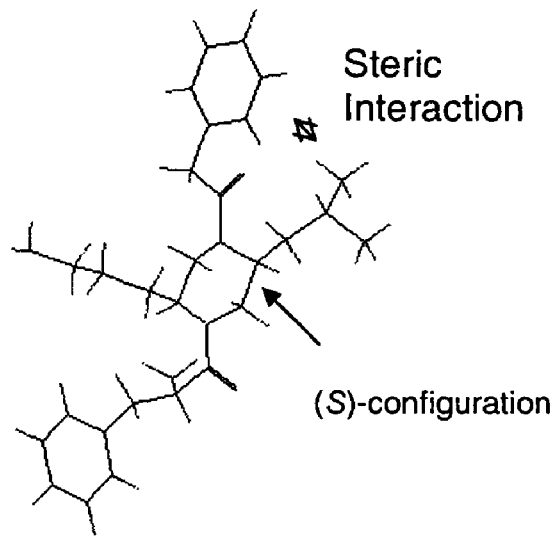
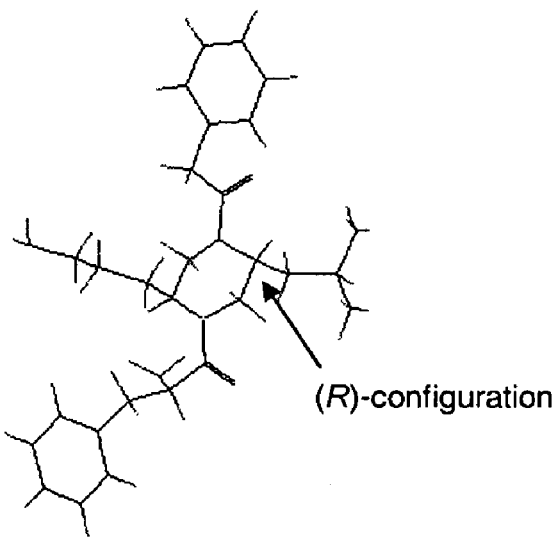
Fig. 1A  Fig. 1B
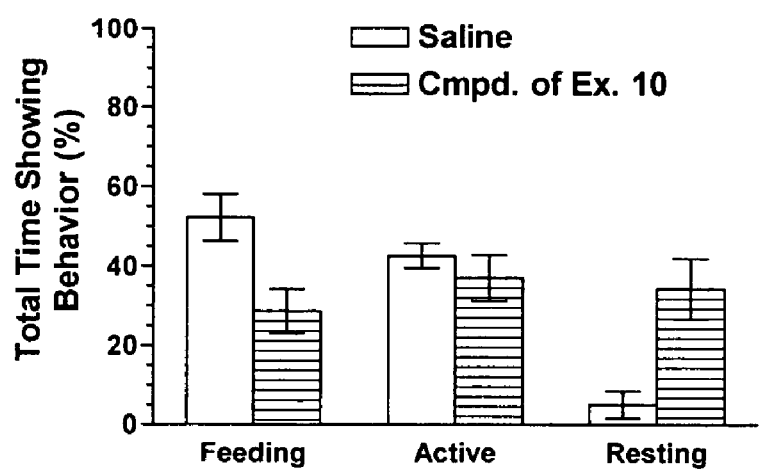
Fig. 2

MELANOCORTIN RECEPTOR-SPECIFIC COMPOUNDS

CROSS-REFERENCE TO RELATED APPLICATIONS

This application claims the benefit of the filing of U.S. Provisional Patent Application Ser. No. 60/546,393, entitled "Melanocortin Receptor-Specific Tetra-Substituted piperazine Compounds", filed on Feb. 19, 2004; and of U.S. Provisional Patent Application Ser. No. 60/467,442, entitled "Tetra-, Penta- and Hexa-Substituted piperazine Compounds and Derivatives", filed on May 1, 2003; and the specification of each thereof is incorporated herein by reference.

BACKGROUND OF THE INVENTION

1. Field of the Invention (Technical Field):

The present invention relates to tetra- and penta-substituted piperazine and piperazine-derivative ring compounds, the ring compounds optionally including one C=O or C=S member, that bind to one or more melanocortin receptors and are optionally agonists, antagonists, mixed agonist-antagonists or inverse agonists with respect to one or more melanocortin receptors, and use thereof for the treatment of metabolic, immune, infection-related and melanocortin receptor-mediated disorders.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Piperazines are an important class of molecular templates that have been employed in the development of several drugs. However, in the prior art generally only mono- or di-substituted piperazine templates have been employed. In a few instances a tri-substituted piperazine has been employed, such as indinavir (Merck), an HIV protease inhibitor drug that incorporates a tri-substituted piperazine.

Melanocortin Receptor-Specific Agents. A family of melanocortin receptor types and subtypes have been identified, including melanocortin 1 receptors (MC1-R) expressed on normal human melanocytes and melanoma cells, melanocortin 2 receptors (MC2-R) for adrenocorticotropin (ACTH) expressed in cells of the adrenal gland, melanocortin 3 and melanocortin 4 receptors (MC3-R and MC4-R), expressed primarily in cells in the hypothalamus, mid-brain and brainstem, and melanocortin 5 receptors (MC5-R), expressed in a wide distribution of tissues.

In general, compounds specific for MC1-R are believed to be useful for treatment of melanoma. Compounds specific for MC3-R or MC4-R are believed to be useful in regulation of energy homeostasis, including use as agents for attenuating food intake and body weight gain, for use in treatment of anorexia and cachexia, for treatment of obesity, and treatment of other food intake and metabolism-related indications. Compounds specific for MC3-R and MC4-R, among other melanocortin receptors, can further be used as agents for treatment of sexual dysfunction, including male erectile dysfunction. Other clinical uses are being explored, such as use of MC4-R antagonists as anxiolytic or antidepressant drugs. Other melanocortin receptor-specific compounds, such as MCR-1 agonists, can be used as tanning agents to increase melanin production in the skin, acting as chemo-preventive agents against harmful effects of UV solar radiation. Compounds specific for MCR-1 and MCR-3 may further be useful in regulation of inflammatory processes. Compounds specific for MCR-5 may be used for treatment of acne and related skin disorders due to over stimulation of sebaceous gland. Compounds specific for MCR-4 and MCR-5 may be used for treatment of depression. Compounds specific for MCR-3 may find use as a therapeutic for treating salt-induced hypertension. In general, the melanocortin system is involved in diverse physiological functions, including energy balance, pigmentation, sexual function and inflammation.

The mechanism of action of compounds specific for MC3-R or MC4-R as agents for attenuating food intake and body weight gain has not been fully elucidated. While most reports suggest that MC4-R agonists may be employed for attenuating food intake and body weight gain, it is clear that agouti-related protein (AgRP), an endogenous inverse agonist, plays a critical role in the regulatory system. At least one group has suggested that a neutral antagonist of AgRP may produce agonist-like effects in vivo. (Adan, R. A. H. and Kas, M. J. H. Inverse agonist gains weight. *TRENDS in Pharmacological Sciences* 24(6):315-321, 2003.) However, no such compounds have heretofore been described. Further, all or virtually all MC4-R agonists compounds reported for attenuating food intake or body weight gain in animal models have shown a "rebound" effect, with animals gaining weight equal to or, in most instances, exceeding controls on cessation of administration of the compounds. There is thus a need for compounds which attenuate food intake or body weight gain without causing a rebound effect on cessation of administration of the compound.

There is a significant need for compounds with high specificity for discrete melanocortin receptors, as well as for compounds that are agonists, inverse agonists, antagonists, or otherwise bind to specific melanocortin receptors. High affinity compounds for melanocortin receptors can be used to exploit varied physiological responses associated with melanocortin receptors, as agonists, antagonists, inverse agonists or otherwise. In addition, melanocortin receptors have an effect on the activity of various cytokines, and high affinity compounds for melanocortin receptors can be used to regulate cytokine activity.

Piperazine Compounds. There are piperazine and piperidine compounds known, such as those disclosed in WO 03/009850 (Amgen), WO 03/009847 (Amgen), WO 03/094918 (Neurocrine Biosciences), WO 03/1093234 (Procter & Gamble), WO 03/092690 (Procter & Gamble), WO 03/061660 (Eli Lilly and Company), WO 03/053927 (Taisho Pharm.), WO 03/031410 (Neurocrine Biosciences), WO 03/007949 (Merck & Co.), WO 02/092566 (Taisho Pharm.), WO 02/079146 (Bristol-Myers Squibb Company), WO 02/070511 (Bristol-Myers Squibb Company), WO 02/068388 (Merck & Co.), WO 02/068387 (Merck & Co.), WO 02/067869 (Merck & Co.), WO 02/059095 (Eli Lilly and Company), WO 02/00259 (Taisho Pharm.), and WO 00/74679 (Merck & Co.), asserted to be specific for melanocortin or related receptors. However, in general such compounds have at most two functional substituted groups, have relatively poor affinity and specificity, and are not suitable for use as a drug compound. There is a significant need for compounds with high specificity for discrete receptors, such as specific melanocortin receptors, as well as compounds that are agonists, inverse agonists, or antagonists for such receptors. High affinity compounds for such receptors can be used to exploit varied physiological responses associated with the receptors, either as agonists or antagonists. There is thus a need for compounds that are more selective, including higher affinity and specificity, and in particular for compounds that have at least four biologically active substituted groups. This invention addresses that need.

WO 02/085925, "Melanocortin Receptor Ligands", to The Proctor & Gamble Company, discloses ketopiperazine structures and methods of synthesis thereof, but does not disclose piperazine structures, piperazine structures with four substituted groups, methods to synthesize piperazine structures, methods to synthesize piperazine or ketopiperazine structures with four substituted groups, or methods to synthesize optically pure structures, and further does not disclose structures with a single substituent group that is a single D-Phe residue, or a derivative or homolog thereof, optionally with an amine capping group.

With respect to certain objects, methods, synthetic schemes, utilities, applications, definitions, protocols and other disclosures, this application is related to PCT/US02/25574, entitled Peptidomimetics of Biologically Active Molecules, filed on Aug. 12, 2002; to PCT/US01/50075, entitled Identification of Target-Specific Folding Sites in Peptides and Proteins, filed on Dec. 19, 2001; and to U.S. patent application Ser. No. 10/762,079, entitled Piperazine Melanocortin-Specific Compounds, filed on Jan. 20, 2004; and the specifications of each of the foregoing are incorporated herein by reference as if set forth in full.

BRIEF SUMMARY OF THE INVENTION

In one embodiment, the invention provides a compound having the formula of structure I:

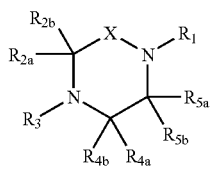

or an enantiomer, stereoisomer or diastereoisomer thereof, or a pharmaceutically acceptable salt thereof,
wherein
X is $CH_2$, C=O or C=S;
$R_1$ is -$L_1$-J;
One of $R_{2a}$ and $R_{2b}$ is -$L_2$—W and the remaining of $R_{2a}$ and $R_{2b}$ is hydrogen;
$R_3$ is -$L_3$-Q;
$L_1$ is a bond or a linker unit comprising from one to eight backbone atoms selected from the group consisting of carbon, sulfur, oxygen or nitrogen;
J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, two substituted or unsubstituted aromatic carbocyclic rings wherein the rings are joined by a bond or —O—, and substituted or unsubstituted aromatic fused heterobicyclic ring groups; wherein in each instance the rings include 5 or 6 ring atoms;
$L_2$ is a bond or —$(CH_2)_y$—;
W is a heteroatom unit with at least one cationic center, hydrogen bond donor or hydrogen bond acceptor wherein at least one heteroatom is nitrogen or oxygen;
$L_3$ is a bond or a linker unit comprising from one to nine backbone atoms selected from the group consisting of carbon, sulfur, oxygen or nitrogen;
Q is an aromatic carbocyclic ring selected from the group consisting of phenyl, substituted phenyl, naphthyl and substituted naphthyl;
One or two of $R_{4a}$, $R_{4b}$, $R_{5a}$, and $R_{5b}$ are independently -$L_2$-W or a $C_1$ to $C_6$ aliphatic linear or branched chain and the remaining of $R_{4a}$, $R_{4b}$, $R_{5a}$, and $R_{5b}$ are hydrogen, provided that at least one of $R_{4a}$ and $R_{4b}$ and at least one of $R_{5a}$ and $R_{5b}$ are hydrogen; and
y is at each occurrence independently from 1 to 6.

In one embodiment of the invention, X is $CH_2$ in the compound of structure I.

In another embodiment of the invention, in the compound of structure I, $L_1$ may be a linker unit selected from the group consisting of:
—$(CH_2)_y$—,
—$(CH_2)_y$—O—,
—$(CH_2)_y$—C(=O)
—$(CH_2)_y$—NH—,
—$(CH_2)_y$—NH—C(=O)—,
—$(CH_2)_y$—C(=O)—NH—,
—$(CH_2)_y$—C(=O)O,
—$(CH_2)_y$—S
—$(CH_2)_y$—$SO_2$—NH—,
—NH—C(=O)—,
—NH—C(=O)—$(CH_2)_y$—,
—NH—$SO_2$—$(CH_2)_y$—,
—NH—$(CH_2)_y$—,
—NH—$(CH_2)_y$—O—,
—$SO_2$—$(CH_2)_y$—,
—C(=O)—NH—,
—C(=O)—NH—$(CH_2)_y$—,
—C(=O)—$(CH_2)_y$—,
—C(=O)— and
—C(=O)—O—$(CH_2)_y$—,
where y is from 1 to 6.

In another embodiment of the invention, in the compound of structure I, J is a substituted or unsubstituted ring structure selected from the group consisting of

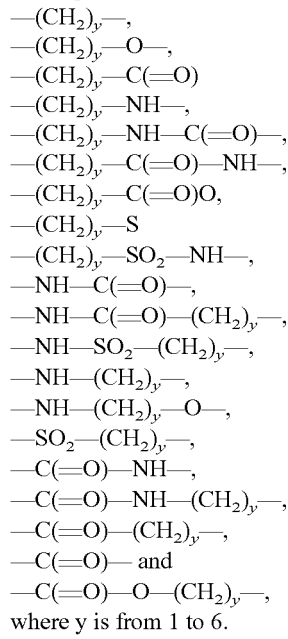

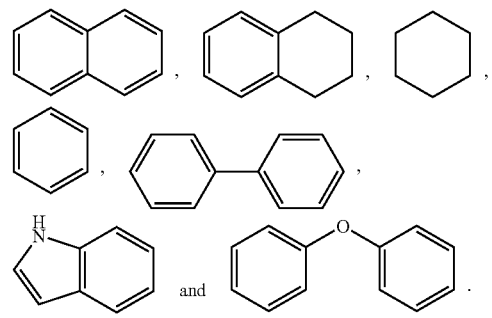

In another embodiment of the invention J is substituted with one or more ring substituents independently selected from the group consisting of hydroxyl, halogen, sulfonamide, alkyl or aryl groups attached directly or through an ether linkage in the compound of structure I.

In another embodiment of the invention, in the compound of structure I, $L_2$ is $(CH_2)_y$ wherein y is between 1 and 4.

In another embodiment of the invention, in the compound of structure I, W is a heteroatom unit with at least one cationic center selected from the group consisting of —NH$_2$ and —NH—C(=NH)—NH$_2$.

In another embodiment of the invention, in the compound of structure I, W may be a heteroatom unit with at least one cationic center, hydrogen bond donor or hydrogen bond acceptor selected from the group consisting of:

—NH—C(=O)—CH$_3$,
—C(=O)—NH—CH$_3$,
—NH—C(=NH)—NH—CH$_3$,
—NH—C(=NH)—NH—CH$_2$—CH$_3$,
—NH—C(=NH)—NH—CH$_2$—CH$_2$—CH$_3$,
—NH—C(=NH)—NH$_2$,
—NH—C(=O)—O—CH$_3$,
—NH—C(=O)—CH$_3$,
—NH—C(=O)—NH$_2$,
—NH—C(=O)—NH—CH$_3$,
—NH—SO$_2$—NH$_2$,
—NH—SO$_2$—CH$_3$,
—C(=O)—NH$_2$,
—OH,

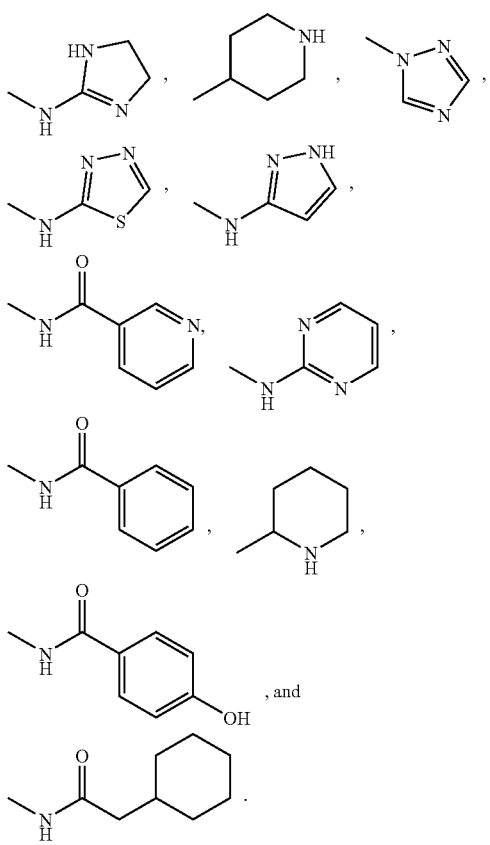

, and

In another embodiment of the invention, in the compound of structure I, L$_3$ may be a linker unit selected from the group consisting of:

—(CH$_2$)$_y$—,
—(CH$_2$)$_y$—O—,
—(CH$_2$)$_y$—O—C(=O)
—(CH$_2$)$_y$—N(R$_{6a}$,R$_{6b}$)—,
—(CH$_2$)$_y$—NR$_{6a}$—C(=O)—,
—(CH$_2$)$_y$—CH(NR$_{6a}$R$_{6b}$)—(CH$_2$)$_y$—,
—(CH$_2$)$_y$—C(=O)CH(NR$_{6a}$R$_{6b}$)—(CH$_2$)$_y$—,
—(CH$_2$)$_y$—C(=O)—,
—(CH$_2$)$_y$—C(=O)—NH—,
—(CH$_2$)$_y$—CH(CH$_3$)—O—,
—(CH$_2$)$_y$—CH(CH$_3$)—C(=O)—,
—(CH$_2$)$_y$—C(=O)—,
—(CH$_2$)$_y$—C(=O)—S—,
—(CH$_2$)$_y$—S—,
—(CH$_2$)$_y$—S—S—,
—(CH$_2$)$_y$—SO$_2$—NH—,
—NH—C(=O)—,
—NH—C(=O)—(CH$_2$)$_y$—,
—NH—SO$_2$—(CH$_2$)$_y$—,
—NH—(CH$_2$)$_y$—,
—NH—(CH$_2$)$_y$—O—,
—NH—(CH$_2$)$_y$—NH—,
—NH—(CH$_2$)$_y$—NH—C(=O)—,
—NH—(CH$_2$)$_y$—C(=O)—NH—,
—NH—(CH$_2$)$_y$—S—,
—NH—(CH$_2$)$_y$—S—S,
—NH—(CH$_2$)$_y$—C(=O)—,
—SO$_2$—(CH$_2$)$_y$—,
—C(=O)—(CH$_2$)$_y$—C(=O)—,
—C(=O)—(CH$_2$)$_y$—C(=O)—NH—,
—C(=O)—(CH$_2$)$_y$—NH—C(=O)—,
—C(=O)—NH—,
—C(=O)—NH—(CH$_2$)$_y$—,
—C(=O)—CH(NR$_{6a}$,R$_{6b}$)—(CH$_2$)$_y$—,
—C(=O)—(CH$_2$)$_y$—O—,
—C(=O)—CH(CH$_3$)—O—,
—C(=O)—CH(CH$_3$)—NH—,
—C(=O)—CH(CH$_3$)—NH—C(=O)—,
—C(=O)—(CH$_2$)$_y$—,
—C(=O)—(CH$_2$)$_y$—CH(NR$_{6a}$,R$_{6b}$)—,
—C(=O)—(CH$_2$)$_y$—CH(NR$_6$,R$_{6b}$)—(CH$_2$)$_y$—,
—C(=O)—(CH$_2$)$_y$—CH(NHR$_{6a}$,R$_{6b}$)—C(=O)—,
—C(=O)—(CH$_2$)$_y$—S,
—C(=O)—(CH$_2$)$_y$—S—S—,
—C(=O)—,
—C(=O)—O—(CH$_2$)$_y$—,

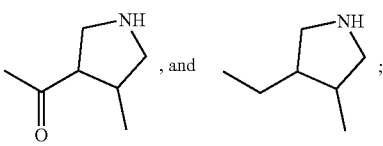

, and wherein

R$_{6a}$ and R$_{6b}$ are each independently selected from the group consisting of hydrogen, R$_7$ and R$_7$—R$_8$;

R$_7$ is an amino acid residue or an amine capping group, provided that if R$_8$ is present, R$_7$ is an amino acid residue;

R$_8$ is H or an amine capping group; and y is from 1 to 6, provided that where any linker unit includes two y index values, the total of such y index values is from 2 to 6.

In the compound of structure I, the amino acid residue at R$_7$, if provided, may be an L-amino acid selected from the group consisting of Abu, 2-Abz, 3-Abz, 4-Abz, Achc, Acpc, Aib, Amb, Arg(Tos), Asp(anilino), Asp(3-Cl-anilino), Asp(3, 5-diCl-anilino), 11-Aun, AVA, Beta-hHyp(Bzl), Cha, Chg, Cmpi, Disc, Dpr(beta-Ala), GAA, GBzA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, IgI, Hyp(2-Naphthyl), Hyp(Phenyl), 2-Aic, Idc, 1-Aic, Beta-homoSer(Bzl), Ser(2-Naphthyl), Ser (Phenyl), Ser(4-Cl-Phenyl), Ser(2-Cl-Phenyl), Thr(Bzl), Tic, Beta-homoThr(Bzl), Thr(2-Naphthyl), Thr(Phenyl), Thr(4-Cl-Phenyl) and Thr(2-Cl-Phenyl), Nle, Leu, Ile, Val and Beta-Ala.

In the compound of structure I, the amine capping group, if provided, may be selected from the group consisting of methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc and 8-Aoc. Alternatively, the amine capping group is polyethylene glycol with a formula molecular weight of between 100 and 10,000.

In any of the foregoing descriptions of the compound of structure I, Q can be

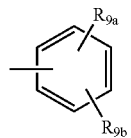

wherein $R_{9a}$ and $R_{9b}$ are optional ring substituents, and when one or both are present, are the same or different and independently hydroxyl, halogen, alkyl, or aryl groups attached directly or through an ether linkage. In one embodiment, at least one of $R_{9a}$ or $R_{9b}$ is an alkyl selected from the group consisting of —$CH_3$ and —$OCH_3$. In another embodiment, at least one of $R_{9a}$ or $R_{9b}$ is a halogen selected from the group consisting of —Cl and —$CF_3$.

In another embodiment of the invention, in the compound of structure I, one of $R_{4a}$, $R_{4b}$, $R_{5a}$, and $R_{5b}$ is a $C_1$ to $C_6$ aliphatic linear or branched chain. In another preferred embodiment, one of $R_{4a}$ or $R_{4b}$ and one of $R_{5a}$ and $R_{5b}$ is a $C_1$ to $C_6$ aliphatic linear or branched chain. In either instance, the $C_1$ to $C_6$ aliphatic linear or branched chain can be selected from the group consisting of methyl and isobutyl.

In another embodiment of the invention, in the compound of structure I the following assignments obtain:
X is $CH_2$;
$L_1$ is a linker unit selected from the group consisting of —$(CH_2)_3$—, —$(CH_2)_2$—, —$CH_2$—, —C(=O)—$CH_2$—, —C(=O)—$(CH_2)_2$— and —C(=O)—$(CH_2)_3$—;
J a ring structure selected from the group consisting of naphthyl, phenyl, substituted phenyl, indole and substituted indole;
$L_2$ is $(CH_2)_3$;
W is —NH—C(=NH)—$NH_2$;
$L_3$ is a linker unit selected from the group consisting of —C(=O)—(C—$NR_{6a}R_{6b}$) —$(CH_2)_y$—, —C(=O)—$(CH_2)_y$— and —$(CH_2)_y$—(C—$NR_{6a}R_{6b}$) —$(CH_2)_y$—;
Q is an aromatic carbocyclic ring selected from the group consisting of phenyl, substituted phenyl and naphthyl;
One of $R_{4a}$, $R_{4b}$, $R_{5a}$, and $R_{5b}$ is methyl or isobutyl, and the remaining of $R_{4a}$, $R_{4b}$, $R_{5a}$, and $R_{5b}$ are hydrogen;
$R_{6a}$ and $R_{6b}$ are each independently selected from the group consisting of hydrogen and $R_7$; and
$R_7$ is selected from the group consisting of acetyl, methyl, dimethyl, ethyl, propyl, isopropyl, butyl, isobutyl, benzyl, benzoyl, hexanoyl, and polyethylene glycol.

Thus in one embodiment the invention includes the following compounds and pharmaceutically acceptable salts thereof:

N-{3-[1-[2(R)-Amino-3-(2,4-dichloro-phenyl)-propionyl]-6(R)-methyl-4-(2-naphthalen-2-yl-ethyl)-piperazin-2(S)-yl]-propyl}-guanidine;

N-{3-[1-[2(R)-Amino-3-(2,4-dichloro-phenyl)-propionyl]-5(R)-methyl-4-(2 naphthalen-2-yl-ethyl)-piperazin-2(S)-yl]-propyl}-guanidine;

N-{3-[1-[2(R)-Amino-3-(2,4-dichloro-phenyl)-propionyl]-5(S)-methyl-4-(2-naphthalen-2-yl-ethyl)-piperazin-2(S)-yl]-propyl}-guanidine;

N-{3-[1-[2(R)-Amino-3-(2,4-dichloro-phenyl)-propionyl]-6(S)-methyl-4-(2-naphthalen-2-yl-ethyl)-piperazin-2(S)-yl]-propyl}-guanidine;

N-{3-[1-[2(R)-Amino-3-(2-chloro-4-methyl-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(4-chloro-2-methyl-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(2,4-dichloro-phenyl)-propionyl]-5(S)-isobutyl-4-(2-naphthalen-2-yl-ethyl)-piperazin-2(S)-yl]-propyl}-guanidine;

N-{3-[1-[2(R)-Amino-3-(2,4-dichloro-phenyl)-propionyl]-5(R)-isobutyl-4-(2-naphthalen-2-yl-ethyl)-piperazin-2(S)-yl]-propyl}-guanidine;

N-{3-[1-[2(R)-Amino-3-(4-chloro-2-fluoro-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(2,4-dim ethyl-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(2-chloro-4-trifluoromethyl-phenyl)-propionyl]-5(R)-methyl-4(2-naphthalen-2-yl-ethyl)-piperazin-2(S)-yl]-propyl}-guanidine;

N-{3-[1-[2(R)-Amino-3-(4-chloro-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(3,4-dichloro-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(2,4-dimethyl-phenyl)-propionyl]-5(R)-methyl-4-(2-naphthalen-2-yl-methyl)-piperazin-2(S)-yl]-propyl}-guanidine;

N-{3-[1-[4-(4-Chloro-phenyl)-pyrrolidine-3-carbonyl]-5(R)-methyl-4-(2-naphthalen-2-yl-ethyl)-piperazin-2(S)-yl]-propyl}-guanidine;

N-{1 (R)-(4-chloro-2-Dimethyl-benzyl)-2-[2(S)-(3-guanidino-propyl)-5(R)-methyl-4-(2-naphthalen-2-yl-acetyl)-piperazin-1-yl]-2-oxo-ethyl}-acetamide;

N-{3-[1-(2(R)-Amino-3-naphthalen-2-yl-propionyl)-5(R)-methyl-4-(2-naphthalen-2-yl-ethyl)-piperazin-2(S)-yl]-propyl}-guanidine;

N-{3-[1-(2(R)-Amino-3-naphthalen-2-yl-propionyl)-5(R)-methyl-4-(3-phenyl-propyl)-piperazin-2(S)-yl]-propyl}-guanidine;

N-{3-[1-(2(R)-Amino-3-naphthalen-2-yl-propionyl)-5(R)-methyl-4-(2-p-tolyl-ethyl)-piperazin-2(S)-yl]-propyl}-guanidine;

N-{3-[1-(2(R)-Amino-3-naphthalen-2-yl-propionyl)-4-(2-1H-indol-3-yl-acetyl)-5(R)-methyl-piperazin-2(S)-yl]-propyl}-guanidine;

N-{3-[1-(2(R)-Amino-3-naphthalen-2-yl-propionyl)-4-(2-1H-indol-3-yl-propionyl)-5(R)-methyl-piperazin-2(S)-yl]-propyl}-guanidine;

N-{3-[1-(2(R)-Amino-3-naphthalen-2-yl-propionyl)-4-(2-1H-indol-3-yl-butyryl)-5(R)-methyl-piperazin-2(S)-yl]-propyl}-guanidine;

N-(3-{1-(2(R)-Amino-3-naphthalen-2-yl-propionyl)-4-[2-(1H-indol-3-yl)-ethyl]-5(R)-methyl-piperazin-2(S)-yl}-propyl)-guanidine; N-(3-{1-(2(R)-Amino-3-naphthalen-2-yl-propionyl)-5(R)-methyl-4-[2-(2-methyl-1H-indol-3-yl)-ethyl]-piperazin-2(S)-yl}-propyl)-guanidine;

N-(3-{1-(2(R)-Amino-3-naphthalen-2-yl-propionyl)-5(R)-methyl-4-[2-(1-methyl-1H-indol-3-yl)-ethyl]-piperazin-2(S)-yl}-propyl)-guanidine;

N-(3-{1-(2(R)-Amino-(4-chloro-phenyl)-propionyl)-5(R)-methyl-4-[2-(1H-indol-3-yl)-ethyl]-piperazin-2(S)-yl}-propyl)-guanidine;

N-(3-{1-(2(R)-Amino-(4-chloro-2-methyl-phenyl)-propionyl)-5(R)-methyl-4-[2-(1H-indol-3-yl)-ethyl]-piperazin-2(S)-yl}-propyl)-guanidine;

N-{3-[1-[2(R)-Amino-3-(phenyl)-propionyl]-5(R)-methyl-4-(2-naphthalen-2-yl-ethyl)-piperazin-2(S)-yl]-propyl}-guanidine;

N-{3-[1-[2(R)-Amino-3-(4-methyl-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(4-methoxy-phenyl)-propionyl]-5(R)-methyl-4-(2-naphthalen-2-yl-ethyl)-piperazin-2(S)-yl]-propyl}-guanidine; N-{3-[1-[3-(4-Chloro-phenyl)-2(R)-dimethylamino-propionyl]-5(R)-methyl-4-(2-naphthalen-2-yl-ethyl)-piperazin-2(b)-yl]-propyl}-guanidine;

N-{3-[1-[3-(4-Chloro-phenyl)-2(R)-methylamino-propionyl]-5(R)-methyl-4-(2-naphthalen-2-yl-ethyl)-piperazin-2(S)-yl]-propyl}-guanidine;

N-{3-[1-[3-(4-Chloro-phenyl)-2(R)-diethylamino-propionyl]-5(R)-methyl-4-(2-naphthalen-2-yl-ethyl)-piperazin-2(S)-yl]-propyl}-guanidine;

N-{3-[1-[3-(4-Chloro-phenyl)-2(R)-isopropylamino-propionyl]-5(R)-methyl-4-(2-naphthalen-2-yl-ethyl)-piperazin-2(S)-yl]-propyl}-guanidine;

N-{3-[1-[2(R)-Amino-3-naphthalen-2-yl-propionyl]-5(R)-isobutyl-4-(2-naphthalen-2-yl-ethyl)-piperazin-2(S)-yl]-propyl}-guanidine;

N-{2-[2(S)-(3-Guanidino-propyl)-5(R)-isobutyl-4-(2-naphthalen-2-yl-ethyl)-piperazin-1-yl]-1 (R)-naphthalen-2-ylmethyl-2-oxo-ethyl}-acetamide;

N-{1(R)-(2,4-Dimethyl-benzyl)-2-[2(S)-(3-guanidino-propyl)-5(R)-methyl-4-(2-naphthalen-2-yl-ethyl)-piperazin-1-yl]-2-oxo-ethyl}-acetamide;

N-{3-[1-(2(R)-Amino-3-naphthalen-2-yl-propionyl)-5(R)-methyl-4-(2-naphthalen-2-yl-acetyl)-piperazin-2(S)-yl]-propyl}-guanidine N-{3-[1-(2(R)-Amino-3-naphthalen-2-yl-propionyl)-4-(3H-imidazol-4-ylmethyl)-5(R)-methyl-piperazin-2(S)-yl]-propyl}-guanidine;

N-{3-[1-(2(R)-Amino-3-naphthalen-2-yl-propionyl)-4-(4-imidazol-1-yl-benzyl)-5(R)-methyl-piperazin-2(S)-yl]-propyl}-guanidine;

N-{2-[2(S)-(3-Guanidino-propyl)-5(R)-methyl-4-(2-naphthalen-2-yl-acetyl)-piperazin-1-yl]-1 (R)-naphthalen-2-ylmethyl-2-oxo-ethyl}-acetamide;

N-{2-[4-(2(R)-Amino-3-naphthalen-2-yl-propionyl)-5(S)-(3-guanidino-propyl)-2(R)-methyl-piperazin-1-yl]-1 (R)-naphthalen-2-ylmethyl-2-oxo-ethyl}-methanesulfonamide;

N-{2-[4-(2(R)-Amino-3-naphthalen-2-yl-propionyl)-5(S)-(3-guanidino-propyl)-2(R)-methyl-piperazin-1-yl]-1(R)-naphthalen-2-ylmethyl-2-oxo-ethyl}-acetamide;

N-{3-[1-[2(R)-Amino-3-(2,4-dimethyl-phenyl)-propionyl]-5(R)-methyl-4-(2-naphthalen-2-yl-acetyl),-piperazin-Z(S)-yl]-propyl}-guanidine;

N-{3-[1-[2(R)-Amino-3-(4-chloro-2-dimethyl-phenyl)-propionyl]-5(R)-methyl-4-(2-naphthalen-2-yl-acetyl)-piperazin-2(S)-yl]-propyl}-guanidine;

N-{1(R)-(2,4-Dimethyl-benzyl)-2-[2(S)-(3-guanidino-propyl)-5(R)-methyl-4-(2-naphthalen-2-yl-acetyl)-piperazin-1-yl]-2-oxo-ethyl}-acetamide;

2(S)-Amino-N-{1 (R)-(2,4-dimethyl-benzyl)-2-[2(S)-(3-guanidino-propyl)-5(R)-methyl-4-(2-naphthalen-2-yl-acetyl)-piperazin-1-yl]-2-oxo-ethyl}-3-(1H-imidazol-4-yl)-propionamide N-{3-[1-[2(R)-Amino-3-(2,4-dimethyl-phenyl)-propionyl]-6(R)-methyl-4-(2-naphthalen-2-yl-acetyl)-piperazin-3(S)-yl]-propyl}-guanidine N-[2-[4-[2(R)-Acetylamino-3-(4-chloro-phenyl)-propionyl]-2(S),5(S)-bis-(3-guanidino-propyl)-piperazin-1-yl]-1 (R)-(4-chloro-benzyl)-2-oxo-ethyl]-acetamide;

N-{3-[1-[2(R)-Amino-3-(4-chloro-phenyl)-propionyl]-5(R)-methyl-4-(2-naphthalen-2-yl-ethyl)-3-oxo-piperazin-2(S)-yl]-propyl}-guanidine;

N-(3-{1-[2(R)-Amino-3-(4-chloro-phenyl)-propionyl]-5(R)-methyl-3-oxo-4-phenethyl-piperazin-2(S)-yl}-propyl)-guanidine;

N-(3-{1-[2(R)-Amino-3-(4-chloro-phenyl)-propionyl]-4-[2-(1H-indol-3-yl)-ethyl]-5(R)-methyl-3-oxo-piperazin-2(S)-yl}-propyl)-guanidine;

N-{3-[1-(2(R)-Amino-3-naphthalen-2-yl-propionyl)-5(R)-methyl-4-(2-naphthalen-2-yl-ethyl)-3-oxo-piperazin-2(S)-yl]-propyl}-guanidine;

2(S)-Amino-N-{1 (R)-(4-chloro-benzyl)-2-[2(S)-(3-guanidino-propyl)-5(R)-methyl-4-(2-naphthalen-2-yl-ethyl)-3-oxo-piperazin-1-yl]-2-oxo-ethyl}-3-(1H-imidazol-4-yl)-propionamide;

2(S)-Amino-N-{1 (R)-(2,4-dimethyl-benzyl)-2-[2(S)-(3-guanidino-propyl)-5(R)-methyl-4-(2-naphthalen-2-yl-ethyl)-piperazin-1-yl]-2-oxo-ethyl}-3-(1H-imidazol-4-yl)-propionamide;

N-{3-[1-[2(R)-(PEG-Amino)-3-(4-chloro-phenyl)-propionyl]-5(R)-methyl-4-(2-naphthalen-2-yl-ethyl)-3-oxo-piperazin-2(S)-yl]-propyl}-guanidine;

N-{3-[1-[2(R)-(PEG-Amino)-3-(4-chloro-phenyl)-propionyl]-5(R)-methyl-4-(2-naphthalen-2-yl-ethyl)-3-piperazin-2(S)-yl]-propyl}-guanidine;

N-{3-[1-[2(R)-Amino-3-(2,4-dichloro-phenyl)-propionyl]-5(R),6(R)-dimethyl-4-(2-naphthalen-2-yl-ethyl)-piperazin-2(S)-yl]-propyl}-guanidine;

N-{3-[1-[2(R)-(PEG-Amino)-3-(4-chloro-phenyl)-propionyl]-5(R)-methyl-4-(2-naphthalen-2-yl-ethyl)-3-piperazin-2(S)-yl]-propyl}-guanidine;

N-{2-[4-(2(R)-Amino-3-(2,4-dimethyl-phenyl)-2-yl-propionyl)-5(S)-(3-guanidino-propyl)-2(R)-methyl-piperazin-1-yl]-1 (R)-benzyl-2-oxo-ethyl}-acetamide;

N-{2-[4-(2(R)-Amino-3-(2,4-dimethyl-phenyl)-2-yl-propionyl)-5(S)-(3-guanidino-propyl)-2(R)-methyl-piperazin-1-yl]-1 (R)-(3-methyl-2,3-dihydro-1H-indol-3-yl-methyl)-2-oxo-ethyl}-acetamide;

N-{1 (R)-Benzyl-2-[4-[3-(2,4-dichloro-phenyl)-propionyl]-5(S)-(3-guanidino-propyl)-2(R)-methyl-piperazin-1-yl]-2-oxo-ethyl}-acetamide;

N-(3-{1-[2(R)-Amino-3-(4-chloro-2-methyl-phenyl)-propionyl]-5(R)-methyl-4-phenylacetyl-piperazin-2(S)-yl}-propyl)-guanidine;

N-(3-{1-[2(R)-Amino-3-(4-chloro-2-methyl-phenyl)-propionyl]-5(R)-methyl-4-(3-phenyl-propionyl)-piperazin-2(S)-yl}-propyl)-guanidine;

N-(3-{1-[2(R)-Amino-3-(4-chloro-2-methyl-phenyl)-propionyl]-5(R)-methyl-4-(4-phenyl-butyryl)-piperazin-2(S)-yl}-propyl)-guanidine;

N-(3-{1-[3-(2,4-Dichloro-phenyl)-propionyl]-5(R)-methyl-4-phenylacetyl-piperazin-2(S)-yl}-propyl)-guanidine;

N-{3-[1-(2(R)-Amino-2-phenyl-acetyl)-5(R)-methyl-4-(3-phenyl-propionyl)-piperazin-2(S)-yl]-propyl}-guanidine; and N-{3-[1-(2(R)-Amino-3-naphthalen-2-yl-propionyl)-5(R)-isobutyl-4-(2-naphthalen-2-yl-acetyl)-piperazin-2(S)-yl]-propyl}-guanidine In yet another embodiment, the invention can be characterized as a compound of the formula of structure II:

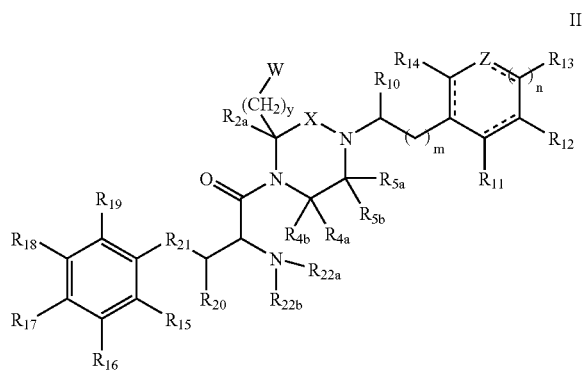

wherein $R_{10}$ is H or =O;

Z is N, NH, CH, $CH_2$ or N—$CH_3$;

$R_{11}$, $R_{12}$, $R_{13}$ and $R_{14}$ are independently hydrogen or a $C_1$ to $C_6$ linear or branched chain on the proviso that either $R_{11}$, and $R_{12}$, or, if n is 1, $R_{12}$ and $R_{13}$, can constitute an aromatic or non-aromatic carbocyclic ring;

$R_{15}$, $R_{16}$, and $R_{19}$ are independently hydrogen or a hydroxyl, halogen, alkyl or aryl groups attached directly or through an ether linkage;

$R_{17}$ and $R_{18}$ are independently hydrogen, a hydroxyl, halogen, alkyl or aryl groups attached directly or through an ether linkage, or together constitute a fused aromatic ring;

$R_{20}$ is hydrogen or a $C_1$ to $C_6$ aliphatic linear or branched chain, optionally containing at least one N;

$R_{21}$ is optionally not present, or if present is a $C_1$ to $C_6$ aliphatic linear or branched chain;

$R_{22a}$ and $R_{22b}$ are independently hydrogen or a $C_1$ to $C_6$ linear or branched chain on the proviso that $R_{20}$ and one of $R_{22a}$ and $R_{22b}$ can form a nonaromatic heterocyclic ring;

m is from 0 to 6;

n is 0 or 1; and the dashed lines are an optional double bond.

Compounds of the invention thus include compounds wherein one of $R_{5a}$ and $R_{5b}$ is an (R)-configuration $C_1$ to $C_6$ aliphatic linear or branched chain, preferably (R)-methyl or (R)-isobutyl, and the remaining of $R_{4a}$, $R_{4b}$, $R_{5a}$, and $R_{5b}$ are hydrogen, and optionally further wherein $L_1$ is —$CH_2$—, —$(CH_2)_2$— or —$(CH_2)_3$—. In one embodiment of the invention, such compounds can be characterized in that they bind to the melanocortin 4 receptor with high affinity and exhibit no intrinsic activity at the melanocortin 4 receptor. The invention further includes a pharmaceutical composition including such compounds or a pharmaceutically acceptable salt thereof and a pharmaceutically acceptable carrier. The invention still further includes a method of treating obesity or feeding-related disorders, comprising administration of a therapeutically effective amount of such a pharmaceutical composition.

Compounds of the invention further include compounds wherein one of $R_{5a}$ and $R_{5b}$ is an (R)-configuration $C_1$ to $C_6$ aliphatic linear or branched chain, preferably (R)-methyl or (R)-isobutyl, and the remaining of $R_{4a}$, $R_{4b}$, $R_{5a}$, and $R_{5b}$ are hydrogen and wherein $L_1$ is selected from the group consisting of —C(=O)—$CH_2$—, —C(=O)—$(CH_2)_2$— and —C(=O)—$(CH_2)_3$—. In one embodiment of the invention, such compounds can be characterized in that they are an agonist or partial agonist at the melanocortin 4 receptor.

In one embodiment of the invention there is provided a method of treating obesity or feeding-related disorders, the method including administration of a therapeutically effective amount of a compound of the invention wherein the compound binds to the melanocortin 4 receptor with high affinity and exhibits no intrinsic activity at the melanocortin 4 receptor.

In another embodiment the present invention provides a compound that is an agonist of a melanocortin receptor, including MC1-R, MC3-R, MC4-R, or MC5-R.

In another embodiment, the present invention provides a compound that is an antagonist of a melanocortin receptor, including MC1-R, MC3-R, MC4-R, or MC5-R.

In another embodiment, the present invention provides a compound that is an inverse agonist of a melanocortin receptor, including MCI-R, MC3-R, MC4-R, or MC5-R.

In another embodiment, the present invention provides a compound that is an antagonist of an inverse agonist, such as agouti-related protein (AgRP), of a melanocortin receptor, including MC4-R.

In yet another embodiment, the present invention provides a compound that binds with high affinity to a melanocortin receptor, including MCI-R, MC3-R, MC4-R, or MC5-R, but which is functionally inactive at physiologically relevant concentrations, is a weak agonist or antagonist ($EC_{50}$ of 100 nM or higher), is an inverse agonist or is an antagonist of an inverse agonist.

In yet another embodiment, the present invention provides a compound that binds with high affinity and specificity to MC4-R but which has no intrinsic activity at MC4-R, and which may be employed for attenuating food intake and body weight gain, including but not limited to treatment of a disorder or condition such as obesity and associated impairment of energy homeostasis.

The invention further includes a method for altering a disorder or condition associated with the activity of a melanocortin receptor, comprising administering to a patient a therapeutically effective amount a compound of this invention. In one embodiment the disorder or condition is an eating disorder such as cachexia. In another embodiment the disorder or condition is obesity and associated impairment of energy homeostasis.

A primary object of the present invention is to provide conformationally constrained isomers of tetra- or penta-substituted piperazines or derivatives thereof, wherein the pendant group substituents are amino acid moieties, amino acid side chain moieties or derivatives thereof, such that the resulting ring compound biologically mimics a relevant reverse turn peptide structure that is characteristic of melanocortin peptides.

Another object of the present invention is to provide tetra- or penta-substituted piperazine compounds and derivatives thereof.

Another object of the present invention is to provide piperazine compounds and derivatives of piperazine compounds with at least four pendant groups, such pendant groups consisting of any moiety other than H, O, S, or a halogen.

Another object of the present invention is to provide piperazine core compounds wherein pendant groups are provided, which pendant groups are or include amino acid side chain moieties.

Another object of the present invention is to provide tetra- or penta-substituted piperazine compounds or derivatives thereof wherein such compounds are specific for one or more melanocortin receptors.

Another object of the present invention is to provide a method for synthesis of tetra-substituted piperazine compounds.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 1A and 1B illustrate steric interaction by placement of the $R_5$ group in an (S)- or (R)-configuration, respectively;

FIG. 2 is a chart showing behavior in an animal model following administration of the compound of Example 10 or a control;

DETAILED DESCRIPTION OF THE INVENTION

Figure 3:
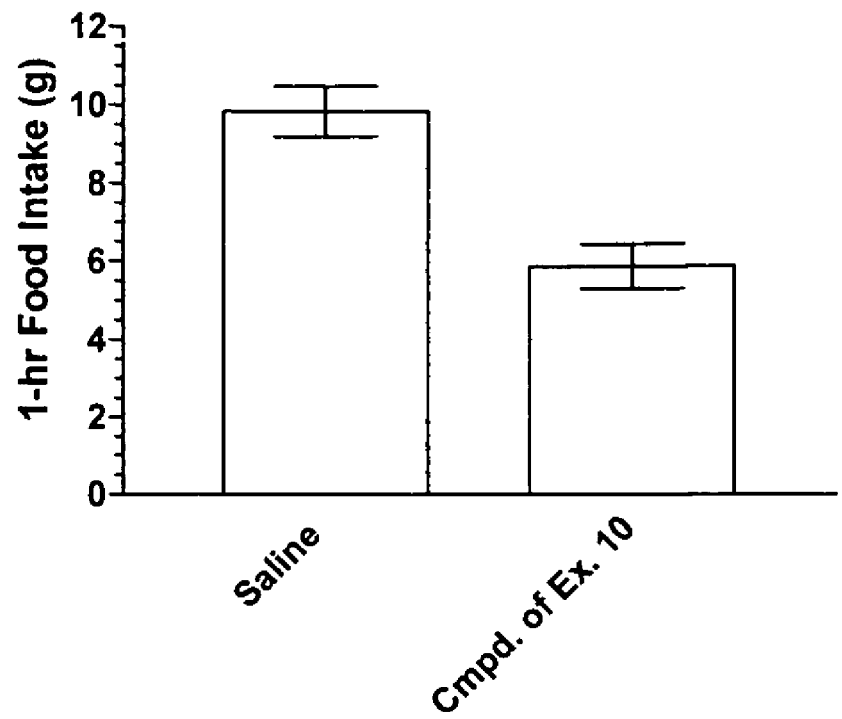
FIG. 3 is a chart of one hour food intake in an animal model following administration of the compound of Example 10 or a control.

In this invention it is disclosed that piperazine rings, including piperazine ring derivatives, may be employed with at least four descriptors, wherein each descriptor is a separate pendant group unique to a given ring atom. By employing four or five descriptors, the inventors have further found that the chirality of the ring, and stereo structure generally, is fixed in a desired structure, thereby more closely mimicking the desired pharmacophores, and with the descriptors positioned in the most relevant chemical space.

This invention thus discloses the use of tetra- or penta-substituted piperazine and related derivative templates for drug design. The invention further also relates to enantiomerically pure tetra-substituted piperazines, preferably made by the synthetic schemes disclosed herein or variants thereof. A classic piperazine ring is a conformationally dynamic six-membered ring structure. It can exist in a variety of conformational states, commonly referred to as chair, boat, twisted chair or twisted boat conformations. Because of this dynamism in structural states, the location of descriptors on the ring plays an important role in stabilizing the ring in a single conformational state; if the appropriate conformational state is selected, this is conducive to making a molecule more selective for its receptor in terms of binding affinity and intrinsic functional activity. For example, a 1,3 axial placement of two bulky descriptors generally causes unfavorable steric interactions between these two groups, and thus make a chair conformation energetically less stable. Consequently, the chair conformation is less preferred, resulting in a twisted chair or boat conformation. The twisted chair or boat conformation results in a specific stereochemical alignment of the descriptors, which is specifically relevant to interaction with the desired receptor. Thus a conformation resulting from 1,3 axial placement of two descriptors may result in a structure more selective for a given receptor sub-type.

In one broad aspect, the invention describes and discloses the use of tetra- or penta-substituted piperazine and related piperazine-derivative ring compounds as biologically active agents. In a related aspect, the invention describes and discloses the use of tetra- or penta-substituted piperazine and related piperazine-derivative ring compounds as mimetics of desired pharmacophores, including but not limited to pharmacophores derived from biologically active metallopeptides, which biologically active metallopeptides may in turn be derived from biologically active peptides, polypeptides or proteins.

In yet another embodiment, the invention describes tetra- or penta-substituted piperazine and related piperazine-derivative ring compounds specific for G-protein coupled receptor systems, such systems including, but not limited to, melanotropin or melanocortin receptors (MC1-R, MC3-R, MC4-R and MC5-R).

In yet another embodiment, the invention provides novel schemes and methods of synthesis of tetra-substituted piperazine and related piperazine-derivative ring compounds.

Definitions. Before proceeding further with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G A Grant, editor, W. H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, including any derivative of an amino acid side chain moiety, as the term "derivative" is defined herein. Therefore, this includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, and saturated or unsaturated alkyl, aryl or aralkyl moieties.

The following abbreviations for amino acids, amino acid side chain moieties and derivatives and constituents thereof have the meanings giving, it being understood that any amino acid may be in either the L- or D-configuration:

| | |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| Aib | alpha-aminoisobutyric acid |
| 1-Aic | 2-aminoindane-1-carboxylic acid |
| 2-Aic | 2-aminoindane-2-carboxylic acid |
| 6-Ahx | 6-amino hexanoic acid |
| Beta-Ala | Bate-alanine |
| Amb | 4-(aminomethyl)-benzoic acid |
| Amc | 4-(aminomethyl)-cyclohexane carboxylic acid |
| 7'-amino-heptanoyl | $NH_2-(CH_2)_6CO-$ |
| 8-Aoc | 8-amino octanoic acid |
| Arg(Tos) | $N^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| Atc | 2-aminotetralin-2-carboxylic acid |
| 11-Aun | 11-amino undecanoic acid |
| AVA | 5-amino valeric acid |
| Beta-hHyp(Bzl) | Beta-(O-benzyl)-homohydroxyproline |
| Beta-hSer(Bzl) | Beta-(O-benzyl)-homoserine |
| Bip | biphenylalanine |
| Bzl | benzyl |
| Bz | benzoyl |
| Cha | cyclohexylalanine |
| Chg | cyclohexylglycine |
| Cmpi | 4-caboxymethyl-piperazine |
| Cys(Bzl) | S-benzyl-cysteine |
| Dip | 3,3-diphenylalanine |
| Disc | 1,3-dihydro-2H-isoindolecarboxylic acid |
| Dpr(beta-Ala) | $N^{beta}$-(3-aminopropionyl)-alpha,beta-diaminopropionic acid |
| Et | ethyl |
| GAA | epsilon-guanidino acetic acid |
| GBzA | 4-guanidino benzoic acid |
| B-Gpa | 3-guanidino propionic acid |

| | |
|---|---|
| GVA(Cl) | beta-chloro-epsilon-guanidino valeric acid |
| Heptanoyl | $CH_3-(CH_2)_5CO-$ |
| hPhe | homophenylalanine |
| hSer | homoserine |
| Hyp | hydroxy proline |
| hHyp | homo hydroxy proline |
| Hyp(Bzl) | O-benzyl-hydroxyproline |
| Hyp(2-naphthly) | O-2' naphthyl-hydroxyproline |
| Hyp(Phenyl) | O-phenyl-hydroxyproline |
| Idc | indoline-2-carboxylic acid |
| Igl | indanylglycine |
| Inp | isonipecotic acid |
| Lys(Z) | N-epsilon-benzyloxycarbonyl-lysine |
| Me | methyl |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| 2-Naphthylacetyl | 2-naphthyl-$CH_2CO-$ |
| (Nlys)Gly | N-(4-aminobutyl)-glycine |
| (N-PhEt)Nal 2 | N(2-phenylethyl)-3-(2-naphthyl) alanine |
| OcHx | cyclohexyl ester |
| Phg | phenylglycine |
| Phe(4-F) | para-fluoro-phenylalanine |
| Phe(4-Br) | 4-bromo-phenylalanine |
| Phe(4-$CF_3$) | 4-trifluoromethyl-phenylalanine |
| Phe(4-Cl) | 4-chloro-phenylalanine |
| Phe(3-Cl) | 3-chloro-phenylalanine |
| Phe(2-Cl) | 2-chloro-phenylalanine |
| Phe(2,4-diCl) | 2,4,-dichloro-phenylalanine |
| Phe(2,4-diF) | 2,4-difluoro-phenylalanine |
| Phe(3,4-diCl) | 3,4,-dichloro-phenylalanine |
| Phe(5-Cl) | 5-chloro-phenylalanine |
| Phe(2-Cl,4-Me) | 2-chloro-4-methyl-phenylalanine |
| Phe(2-Me,4-Cl) | 4-chloro-2-methyl-phenylalanine |
| Phe(2-F,4-Cl) | 4-chloro-2-fluoro-phenylalanine |
| Phe(2,4-diMe) | 2,4-dimethyl-phenylalanine |
| Phe(2-Cl,4-$CF_3$) | 2-chloro-4-trifluoromethyl-phenylalanine |
| Phe(3,4-diF) | 3,4,-difluoro-phenylalanine |
| Phe(4-l) | 4-iodo-phenylalanine |
| Phe(3,4-di-OMe) | 3,4,-dimethoxy-phenylalanine |
| Phe(4-Me) | 4-methyl-phenylalanine |
| Phe(4-OMe) | 4-methoxy-phenylalanine |
| Phe(4-NC) | 4-cyano-phenylalanine |
| Phe(4-$NO_2$) | 4-nitro-phenylalanine |
| Pip | pipecolic acid |
| Pr | propyl |
| Pr-i | isopropyl |
| 4-phenylPro | 4-phenyl-pyrrolidin-2-carboxylic acid |
| 5-phenylPro | 5-phenyl-pyrrolidin-2-carboxylic acid |
| 3-Pya | 3-pyridylalanine |
| Pyr | pyroglutamic acid |
| Qal(2') | beta-(2-quinolyl)-alanine |
| Sal | 3-styrylalanine |
| Sar | sarcosine |
| Ser(Bzl) | O-benzyl-serine |
| Ser(2-Naphthyl) | O-2-Naphthyl-serine |
| Ser(Phenyl) | O-2-Phenyl-serine |
| Ser(4-Cl-Phenyl) | O-4-Cl-Phenyl-serine |
| Ser(2-Cl-Phenyl) | O-2-Cl-Phenyl-serine |
| Ser(p-Cl-Bzl) | O-4-Cl-Benzyl-serine |
| Thr(Bzl) | O-Benzyl-threonine |
| Thr(2-Naphthyl) | O-(2-naphthyl)-threonine |
| Thr(Phenyl) | O-phenyl-threonine |
| Thr(4-Cl-Phenyl) | O-(4-Cl-phenyl)-threonine |
| Thr(2-Cl-Phenyl) | O-(2-Cl-phenyl)-threonine |
| Beta-homoThr(Bzl) | O-Benzyl-bate-homothreonine |
| Tic | 1,2,3,4-tetrahydroisoquinoline-3-carboxylic acid |
| Tiq | 1,2,3,4-tetrahydroisoquinoline-1-carboxylic acid |
| Tle | tert-butylalanine |
| Tpi | 1,2,3,4-tetrahydronorharman-3-carboxylic acid |
| Tyr(Bzl) | O-benzyl-tyrosine |
| Tyr(2,6-DiCl-Bzl) | O-(2,6 dichloro)benzyl-tyrosine |

Conventional amino acid residues have their conventional meaning as given in Chapter 2400 of the *Manual of Patent Examining Procedure, 7th* Ed. Thus, "Nle" is norleucine, "Asp" is aspartic acid, "His" is histidine, "D-Phe" is D-phenylalanine, "Arg" is arginine, "Trp" is tryptophan, "Lys" is lysine, "Gly" is glycine, "Pro" is praline, "Tyr" is tyrosine, "Ser" is serine and so on.

The following amino acids, or side chains thereof, may be employed, in either the L- or D-configuration as appropriate, in certain embodiments of this invention:

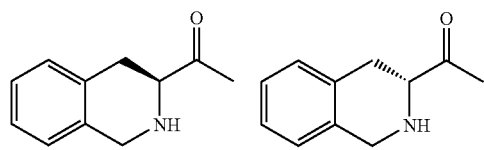
L-Tic     D-Tic

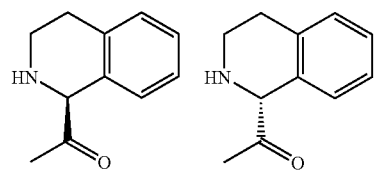
L-Tiq     D-Tiq

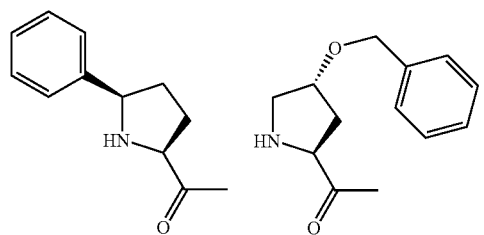
(2S,5R)-5-Phenyl-pyrrolidine-2-carbonyl     trans-Hyp(Bzl)

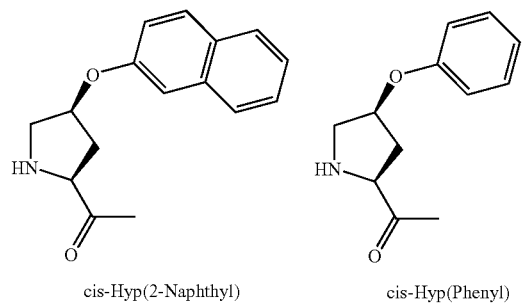
cis-Hyp(2-Naphthyl)     cis-Hyp(Phenyl)

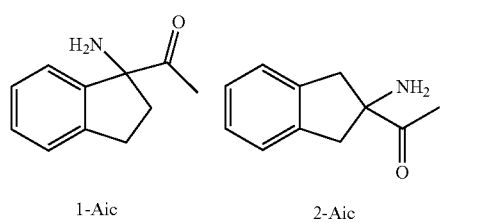
1-Aic     2-Aic

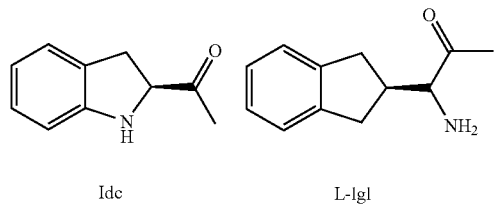
Idc     L-Igl

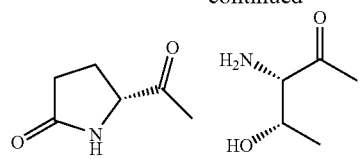
D-Pry     Allo-Thr

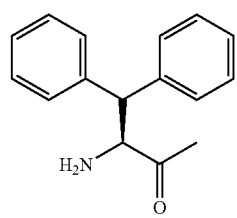
L-Dip

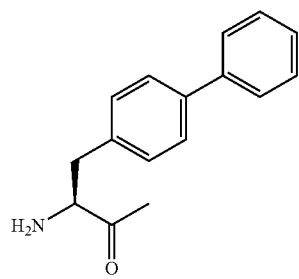
L-Bip

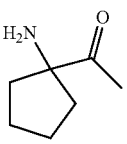
1-Acp

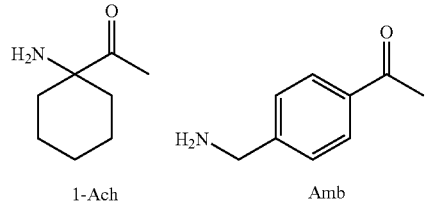
1-Ach     Amb

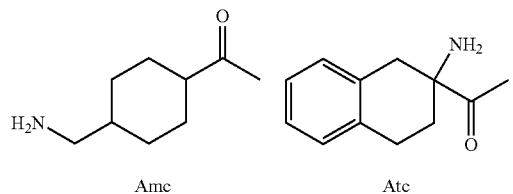
Amc     Atc

The term "homolog" includes, without limitation, (a) a D-amino acid residue or side chain substituted for an L-amino acid residue side chain, (b) a post-transiationally modified residue or side chain substituted for the residue or side chain, (c) a non-protein or other modified amino acid residue or side chain based on another such residue or side chain, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical—$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl [—(C=O)—] groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

An "amine capping group" includes any terminal group attached through a terminal amine, including but not limited to any omega amino derivative, acyl group or terminal aryl or aralkyl including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, as well as terminal groups such polyethylene glycol (PEG) with an average or formula molecular weight of between 100 and 10,000, optionally a PEG carboxylic acid derivative capable of forming a covalent bond with a terminal amine.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more pharmaceutically active ingredients and agents.

A variety of chemicals and compounds are employed in this invention, and the following abbreviations have the meanings given:

| | |
|---|---|
| AcOH | acetic acid |
| Boc | tertiary butyloxycarbonyl |
| Cbz | benzyloxycarbonyl |
| DCM | dichloromethane |
| DEAD | diethyl azodicarboxylate |
| DIAD | diisopropyl azodicarboxylate |
| DIC | 1,3-diisopropylcarbodiimide |
| DMF | N,N-dimethylformamide |
| DMSO | dimethyl sulfoxide |
| EtOAc | ethyl acetate |
| Fmoc | 9-fluorenylmethoxycarbonyl |
| HBTU | 2-(1H-benzotriazole-1-yl)-1,1,3,3-tetramethyluronium hexafluorophosphate |
| HEPES | 4-(2-hydroxyethyl)1-piperazineethanesulfonic acid |
| HOAt | 1-hydroxy-7-azabenzotriazole |
| IBCF | isobutyl chloroformate |
| LAH | lithium aluminum hydride |
| NMM | N-methyl-morpholine |
| NMP | 1-methyl-2-pyrrolidinone |
| Prt | A protecting group, such as Boc, Cbz or Fmoc |
| TBTU | 2-(1H-Benzotriazole-1-yl)-1,1,3,3-tetramethyluronium tetrafluoroborate |
| TEA | triethylamine |
| TFA | trifluoroacetic acid |
| THF | tetrahydrofuran |
| TPP | triphenylphosphine |

A "tetra-substituted piperazine" or "penta-substituted piperazine", as used herein, is a piperazine compound or derivative thereof wherein a group other than solely H, and preferably including an amino acid residue or an amino acid side chain moiety, is attached to each ring N member, and further wherein a group other than solely H, O, S or a halogen, preferably including an amino acid side chain moiety, is attached to two ring C members for a tetra-substituted piperazine and to three ring C members for a penta-substituted piperazine.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction includes an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be related to boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound of this invention that can interact with a melanocortin receptor and initiate a pharmacological response, including but not limited to adenyl cyclase expression, characteristic of the melanocortin receptor. By a melanocortin receptor "antagonist" is meant a drug or a compound, including a compound of this invention, that opposes the melanocortin receptor-associated responses normally induced by a melanocortin receptor agonist agent, but without itself initiating a pharmacological response characteristic of the melanocortin receptor, such as increasing or decreasing adenyl cyclase expression. By a melanocortin receptor "inverse agonist" is meant a drug or a compound, including a compound of this invention, that is an antagonist with respect to an agonist, and which by itself induces or initiates a pharmacological response characteristic of the melanocortin receptor, such as reducing basal or constitutive adenyl cyclase expression.

By "binding affinity" is meant the ability of a compound or drug to bind to its biological target.

By "intrinsic activity" is meant the maximal stimulation of adenyl cyclase achievable by a compound in a melanocortin receptor cell system. The maximal stimulation achieved by A-MSH or NDP-α-MSH is designated as an intrinsic activity of 1.0 (or 100%) and a compound capable of stimulating half the maximal activity that of α-MSH or NDP-α-MSH is designated as having an intrinsic activity of 0.5 (or 50%). A compound of this invention that under assay conditions described herein has an intrinsic activity of 0.7 (70%) or higher is classified as an agonist, a compound with intrinsic activity between 0.1 (10%) and 0.7 (70%) is classified as a partial agonist, and a compound with intrinsic activity below 0.1 (10%) is classified as inactive or having no intrinsic activity. Compounds with intrinsic activity below 0.1 (10%) were further evaluated, as indicated herein, for antagonist effect.

Clinical Applications. The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist peptidomimetic compound of this invention can accordingly be used as a therapeutic chemoprevention agent for combating harmful sun or UV exposure that induces neoplastic activity in skin melanocytes.

In another embodiment, compounds of this invention that are MC4-R agonists can be used as a therapeutic agent to modify energy metabolism and feeding behavior, including treatment of pathologic obesity and related conditions. Compounds of this invention that are MC4-R antagonists can be used as a therapeutic agent in eating disorders, such as treatment of anorexia and cachexia, which is malnutrition and wasting due to illness. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with a maturity-onset obesity syndrome associated with hyperphagia, hyperinsulinemia and hyperglycemia.

This invention include compounds that are MC4-R agonists or partial agonists with demonstrated efficacy, in animal models, in modifying energy metabolism and feeding behavior, and further includes compounds that are inactive or have no intrinsic activity with respect to MC4-R, but bind MC4-R with high affinity and, in some instances, selectivity, and further have demonstrated efficacy, in animal models, in modifying energy metabolism and feeding behavior. It is hypothesized, without desiring to be bound by theory, that at least some compounds of this invention that bind MC4-R with high affinity are neutral antagonists of the inverse agonist AgRP, but independently are inactive or have no intrinsic activity with respect to MC4-R, and that such compounds may be used as a therapeutic agent to modify energy metabolism and feeding behavior, including treatment of pathologic obesity and related conditions.

In yet another embodiment, compounds of this invention can be used as therapeutic agents for treatment of sexual dysfunction, including treatment of both male erectile dysfunction and female sexual dysfunction.

In yet another embodiment, compounds of this invention may be used as therapeutic agents for treatment of inflammation, including specifically MC1-R, MC3-R and MC5-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

The compounds may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The compounds may be administered by any systemic or partially systemic means known in the art, including but not limited to intravenous injection, subcutaneous injection, administration through mucous membranes, oral administration, dermal administration, skin patches, aerosols and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, such that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic acids. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

Therapeutically Effective Amount. In general, the actual quantity of compound of this invention administered to a patient will vary between fairly wide ranges depending upon the mode of administration, the formulation used, and the response desired. This may readily be determined by one of ordinary skill in the art through means such as pharmacokinetic studies, plasma half-life studies, dose escalation studies, and the like. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to induce the desired therapeutic effect.

The compounds of this invention are highly active. For example, the compound can be administered at 0.01, 0.05, 0.1, 0.5, 1, 5, 10, 50, 100, or 500 µg/kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Combination Therapy and Sexual Dysfunction. It is also possible and contemplated to use the compounds of this invention in combination with other drugs or agents for treatment of sexual dysfunction. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, compounds of the invention are used in combination with a therapeutically effective amount of a cyclic-GMP-specific phosphodiesterase inhibitor or an alpha-adrenergic receptor antagonist. Similarly, the compounds of this invention may be used in combination with any known mechanical aids or devices.

The present invention thus provides methods of treating sexual dysfunction, the methods comprising the step of administering to the patient having or at risk of having sexual dysfunction a therapeutically effective amount of a compound of this invention in combination with a therapeutically effective amount of a second sexual dysfunction pharmaceutical agent. The compound of this invention may be administered simultaneously with, prior to or subsequent to administration with a therapeutically effective amount of a second sexual dysfunction pharmaceutical agent. Preferably the compound of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the compound of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the compound of this invention when desired or needed by the patient.

The present invention thus provides methods of treating sexual dysfunction, the methods comprising the step of administering to a patient having or at risk of having sexual dysfunction a therapeutically effective amount of a compound of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a compound of this invention in combination with a compound that is a melanocortin receptor agonist and in combination with another compound that is useful in the treatment of sexual dysfunction.

In a preferred embodiment of combination therapy the sexual dysfunction is female sexual dysfunction. In an especially preferred embodiment of combination therapy the sexual dysfunction is erectile dysfunction. In a preferred embodiment of the foregoing methods, the melanocortin receptor agonist is an agonist of MC3-R or MC4-R, and preferably MC4-R. The agonist may be a non-selective MC3-R and MC4-R agonist.

The present invention also provides pharmaceutical compositions that comprise 1) a compound of this invention and 2) a compound that is a melanocortin receptor agonist. The present invention further provides pharmaceutical compositions that comprise 1) a compound of this invention; 2) a compound that is a melanocortin receptor agonist; and 3) a third compound useful for the treatment of sexual dysfunction. The present invention further provides pharmaceutical compositions that comprise 1) a compound of this invention and 2) a second compound useful for the treatment of sexual dysfunction.

Representative agonists of the melanocortin receptor which are a second compound useful in combination therapy are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borschart et al., Plenum Press, New York (1998); R. T. Dorr et al., Evaluation of Melanotan-II, A Superpotent Cyclic Melanotropic Peptide in a Pilot Phase-I Clinical Study. *Life Sci.* 58:1777-1784 (1996); and R. A. H. Adan, Identification of Antagonists for Melanocortin MC3, MC4, and MC5 Receptors. *Eur. J. Pharmacol.*, 269: 331-337 (1994).

In one embodiment of the composition above, the agonists are MSH including α-, β-, and γ-MSH and/or ACTH.

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)-OH, as disclosed in U.S. Pat. No. 6,579,968. Alternatively, the agonist may be any agonist disclosed in any of the following patents or patent applications: U.S. Pat. Nos. 6,534,503, 6,472,398, 6,458,790, 6,410,548, 6,376,509, or 6,350,760; U.S. Published Application Nos. 2002/01.37664, 2002/0004512, 2002/0143141, or US 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; dopanergic ligands; androgens; selective androgen receptor modulators (SARMs); buproprion; vasoactive intestinal peptide (VIP); neutral endopeptidase inhibitors (NEP); neuropeptide Y receptor antagonists (NPY); and bombesin receptor-3 antagonists.

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, Levitra®, Cialis®, or may be 1-[[3-(6,7-dihydro-1-methyl-7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolid in-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a compound of this invention may be used in combination with any known mechanical aids or devices.

The present invention also provides kits for the treatment of sexual dysfunction (including erectile dysfunction), the kits comprising: a first pharmaceutical composition including a compound of this invention; a second pharmaceutical composition comprising a second compound useful for the treatment of sexual dysfunction; and, a container for the first and second compositions.

Female Sexual Dysfunction. The compounds of this invention may be used to treat female Sexual dysfunction as well as male sexual dysfunction. In general, the dosing schedules and closes for females are comparable to those for males.

Combination Therapy and Weight Regulation. It is also possible and contemplated to use compounds of this invention in combination with other drugs or agents for treatment of various weight and feeding-related disorders. Where the compound is an agonist or partial agonist, the compound may be employed for decreasing food intake and/or body weight in combination with any other agent or drug heretofore employed as a diet aid, or for decreasing food intake and/or body weight. Where the compound binds with high affinity and specificity to MC4-R but has no intrinsic activity at MC4-R, the compound may be employed for decreasing food intake and/or body weight in combination with any other agent or drug heretofore employed as a diet aid, or for decreasing food intake and/or body weight. Where the compound is an antagonist, the compound may be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-duhydro-1H-imidazol-2-yl)ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable non-limiting serotonergic agents include sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonists and selective serotonin reuptake inhibitors including fluoxetine, fluvoxamine, paroxtine, sertraline and other useful compounds as disclosed by U.S. Pat. No. 6,162,805 which is incorporated herein by reference. Other potential inhibitors that may be employed include 5HT2c inhibitors.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference; certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; and certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting examples of monoamine oxidase inhibitors include befloxatone, moclobemide, brofaromine, phenoxathine, esuprone, befol, toloxatone, pirlindol, amiflamine, sercloremine, bazinaprine, lazabemide, millacemide, caroxazone and other certain compounds as disclosed by WO 01/12176 which is incorporated herein by reference.

Certain compounds that increase lipid metabolism are also useful with the practice of the present invention. Such compounds include, but are not limited to, useful evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™ capsules ((S)-2-formylamino-4-methyl-pentanoic acid (S)-1-[[(2S, 3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists for example certain compounds in U.S. Pat. No. 4,626,549 which is incorporated by reference herein, and α-2-adrenergic and growth hormones compounds as described in U.S. Pat. Nos. 4,937,267 and 5,120,713 which are incorporated by reference herein.

Generally, a total dosage of the above-described obesity control agents or medications, when used in combination with a compound of this invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megastrol acetate, adrenocorticoids such as precinisoine and dexamethanasone cyproheptidine, serotonergic drugs such as fenfluramine, neuropeptide Y, and androgen antagonists such as flutamide, nilutamide, and zanoterone.

Compounds of the Invention. As discussed hereafter in the synthetic schemes, one preferred method of making the compounds of the invention includes synthesis of a linear intermediate composed of chiral building blocks such as amino acid residues or derivatives, which intermediate includes the $R_1$ group and an $R_2$ group, and one of or, if provided, both an $R_4$ and $R_5$ group, as shown below. The linear intermediate is then cyclicized, and other groups, such as $R_3$, are then added. Thus in this embodiment $R_1$ and $R_4$ can be considered to be amino acid side chain moieties, as defined above. In other of the synthetic schemes, the linear intermediate includes the $R_2$ group, and one of $R_4$ or $R_5$, with the $R_1$ group synthetically added post-cyclization. In the synthetic methods the $R_3$ group is an amino acid residue or derivative, optionally with an amine capping group, second amino acid residue or derivative, or second amino acid residue or derivative and amine capping group. It may thus be seen that the compounds of the invention may be considered as a 6-membered ring compound of the formula:

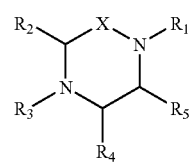

wherein:

X is $CH_2$, C=O or C=S;

$R_1$ is an amino acid side chain moiety including at least one carbocyclic aromatic or non-aromatic ring or heterocyclic aromatic ring, and in a preferred embodiment includes a substituted or unsubstituted phenyl, naphthyl or indole group;

$R_2$ is an amino acid side chain moiety with at least one heteroatom cationic center, hydrogen bond donor or hydrogen bond acceptor, wherein the least one heteroatom is nitrogen or oxygen;

$R_3$ includes at least one amino acid residue with at least one carbocyclic aromatic ring and in a preferred embodiment, includes a substituted or unsubstituted phenyl or naphthyl group; and At least one of $R_4$ and $R_5$ is $R_2$ or a $C_1$ to $C_6$ aliphatic linear or branched chain.

It may readily be seen that the foregoing description is simplified, in that at each of $R_2$, $R_4$ and $R_5$ there is assumed to further be a hydrogen, atom bound to the respective ring carbon.

Thus, by way of example, $R_1$ can be an amino acid side chain moiety, including but not limited to one of the following:

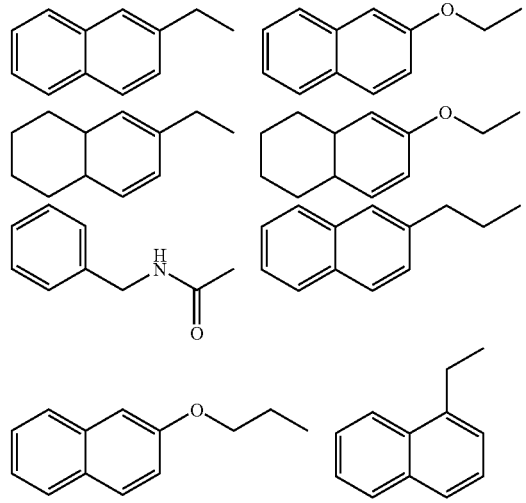

-continued

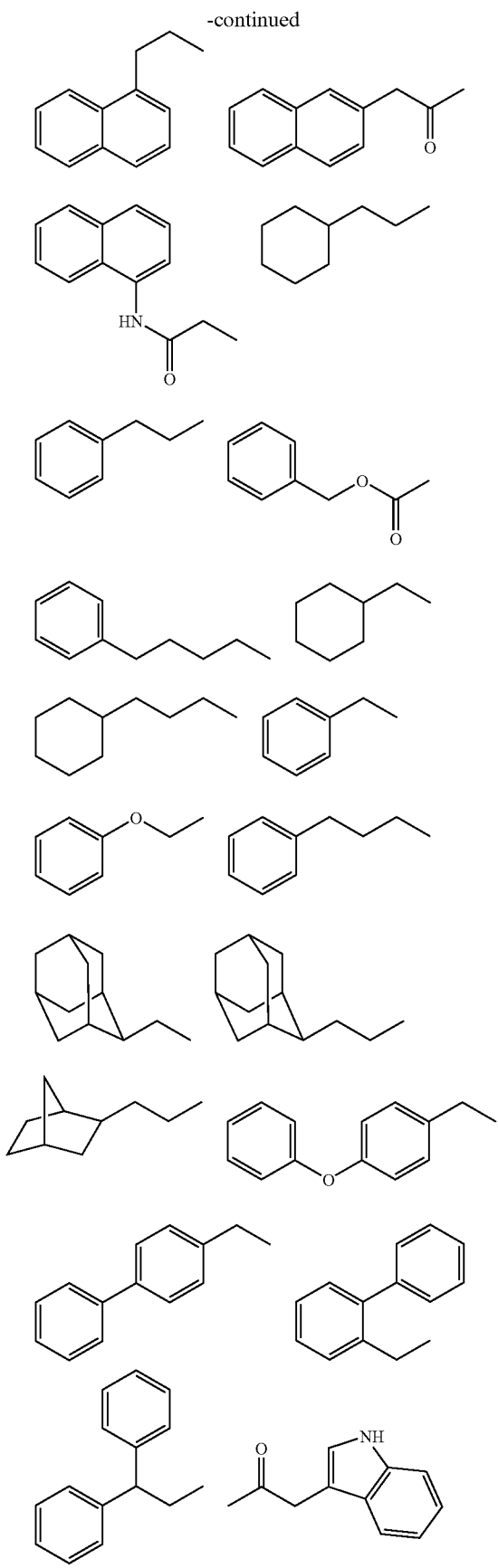

-continued

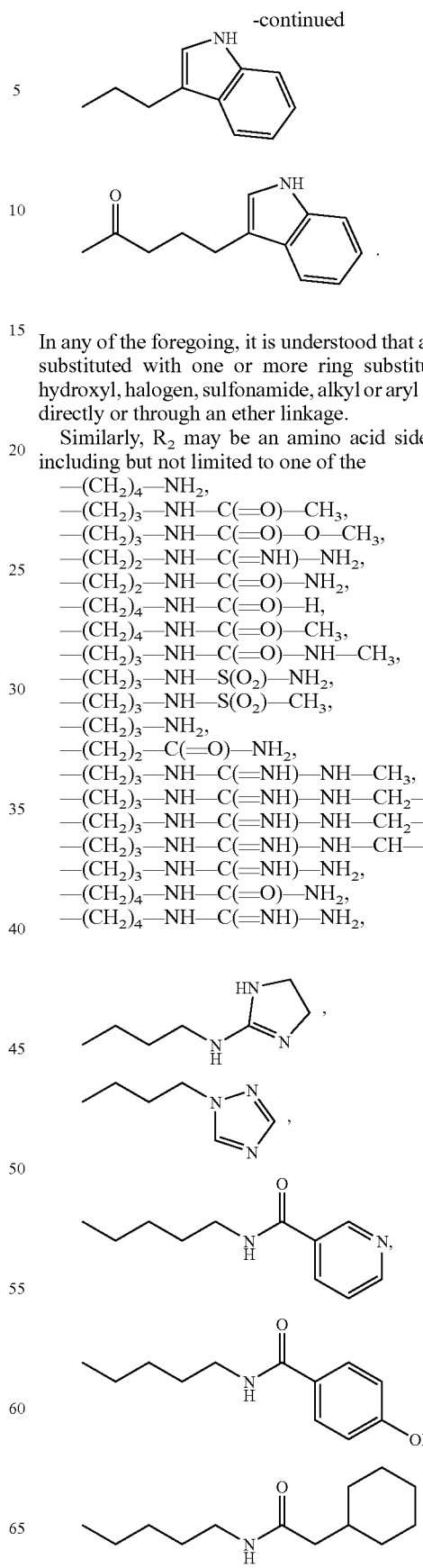

In any of the foregoing, it is understood that any ring may be substituted with one or more ring substitutents, such as hydroxyl, halogen, sulfonamide, alkyl or aryl groups attached directly or through an ether linkage.

Similarly, $R_2$ may be an amino acid side chain moiety, including but not limited to one of the
—$(CH_2)_4$—$NH_2$,
—$(CH_2)_3$—NH—C(=O)—$CH_3$,
—$(CH_2)_3$—NH—C(=O)—O—$CH_3$,
—$(CH_2)_2$—NH—C(=NH)—$NH_2$,
—$(CH_2)_2$—NH—C(=O)—$NH_2$,
—$(CH_2)_4$—NH—C(=O)—H,
—$(CH_2)_4$—NH—C(=O)—$CH_3$,
—$(CH_2)_3$—NH—C(=O)—NH—$CH_3$,
—$(CH_2)_3$—NH—$S(O_2)$—$NH_2$,
—$(CH_2)_3$—NH—$S(O_2)$—$CH_3$,
—$(CH_2)_3$—$NH_2$,
—$(CH_2)_2$—C(=O)—$NH_2$,
—$(CH_2)_3$—NH—C(=NH)—NH—$CH_3$,
—$(CH_2)_3$—NH—C(=NH)—NH—$CH_2$—$CH_3$,
—$(CH_2)_3$—NH—C(=NH)—NH—$CH_2$—$CH_2$—$CH_3$,
—$(CH_2)_3$—NH—C(=NH)—NH—CH—$(CH_3)_2$,
—$(CH_2)_3$—NH—C(=NH)—$NH_2$,
—$(CH_2)_4$—NH—C(=O)—$NH_2$,
—$(CH_2)_4$—NH—C(=NH)—$NH_2$, -continued

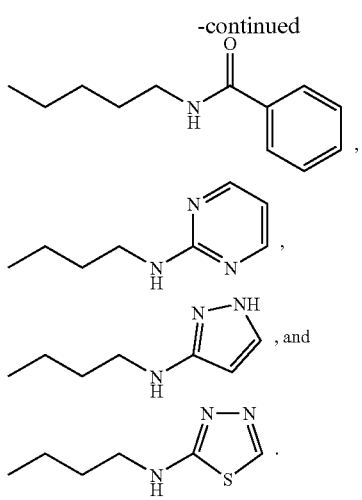

Particularly preferred are side chains of arginine, lysine and ornithine, including derivatives of arginine, lysine and ornithine.

R$_3$, which includes least one amino acid residue with at least one carbocyclic aromatic ring, may be of any of the formulas -A$_1$, -A$_1$-cGp, -A$_1$-A$_2$ or-A$_1$-A$_2$-cGp, where A$_1$ is an amino acid with an aromatic carbocyclic ring, A$_2$ is an L-amino acid, and cGp is an amine capping group. Thus for example it can be seen that the following compounds are contemplated and included within the invention:

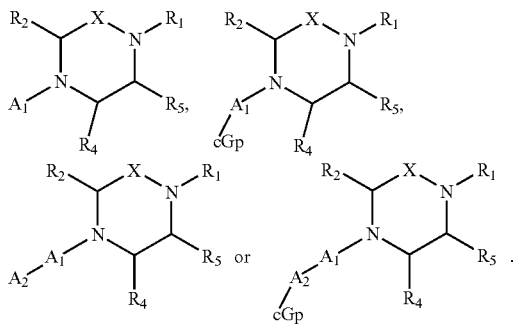

In a preferred embodiment, A$_1$ is a D-amino acid with an aromatic carbocyclic ring. Thus A$_1$ may be a D-isomer of Phe, Phe(2-Cl), Phe(4-Cl), Phe(2,4-diCl), Phe(2,4-diF), Phe(3,4-diCl), Phe(4-NO$_2$), Phe(4-Me), Phe(4-Phenyl), HPhe, Phe(4-F), Phe(4-Br), Phe(4-CF$_3$), Phe(3,4-diF), Phe(4-I), Phe(2-Cl, 4-Me), Phe(2-Me, 4-Cl), Phe(2-F, 4-Cl), Phe(2,4-diMe), Phe (2-Cl, 4-CF$_3$), or Phe(3,4-di-OMe). Alternatively, A$_1$ may be a D-isomer of Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Lys(Z), Lys(Z-2'Br), Lys(Bz), Thr(Bzl), Tic, Tiq, Cys(Bzl), Tyr(2,6-DiCl-Bzl) or Tyr(Bzl). A$_2$, where provided, can be an L-isomer of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp (Bzl), Cha, Chg, Cmpi, Disc, Dpr(beta-Ala), GAA, GBzA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser (2-Naphthyl), Ser(Phenyl), Ser(4-Cl-Phenyl), Ser(2-Cl-Phe-nyl), Thr(Bzl), Tic, Beta-homoThr(Bzl), Thr(2-Naphthyl), Thr(Phenyl), Thr(4-Cl-Phenyl), Thr(2-Cl-Phenyl), Nle, Leu, Ile, Val or Beta-Ala. The amine capping group cGp, where provided, can be methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc, 8-Aoc or polyethylene glycol.

Modulation of functional activity of the compounds of this invention. The efficacy and functional activity of compounds of this invention can be modulated by selection of the linker units and other substituents, such as R$_4$ and/or R$_5$ groups, which influence the conformational biasness of R$_1$ and R$_3$ groups. Efficacy and functional activity may be determined by any number of means, such as assaying the stimulation of adenyl cyclase in a cAMP assay as hereafter described.

For example, the chemical nature of either or both the L$_1$ or L$_3$ linker units, and the incorporation of a substituent at one or more specific R$_{4a}$, R$_{4b}$, R$_{5a}$ or R$_{5b}$ positions, can change otherwise identical compounds from a partial agonist to a full agonist as determined by adenyl cyclase assays in an hMCR-4 transfected HEK cell system. The nature and character of these changes is described, in part, in the following discussion.

A commercially available computer based molecular modeling software system, such as Alchemy (Tripos), can be used to study the conformational dynamics within the compounds of this invention. Studies using such a molecular modeling software system can explain, in part, the effect of changes such as the chemical nature of either or both the L$_1$ or L$_3$ linker units or the incorporation of a substituent at one or more specific R$_{4a}$, R$_{4b}$, R$_{5a}$ or R$_{5b}$ positions on biological activity.

A piperazine ring can exhibit conformational dynamics between chair and boat conformations, with twisted chair and twisted boat conformations being special cases. In the following discussion, chair and boat conformations are used for purposes of illustration. Assume a piperazine, where X is CH$_2$, and a conventional ring atom numbering system as follows:

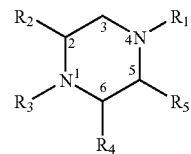

As may readily be seen, both the 1 and 4 position nitrogens are substituted with an R group. As a direct result thereof, the conformation of the ring is biased toward a chair conformation, because this conformation offers a very low likelihood of steric interactions involving aromatic R$_1$ and R$_3$ groups. This may be seen in the following illustration, wherein the equatorial placement of R$_1$ and R$_3$ in the Chair Form results in a conformationally preferred structure, while the close proximity of the ring nitrogens with R$_1$ and R$_3$ groups in the Boat Form (indicated by the double arrow) make the Boat Form conformationally disfavored.

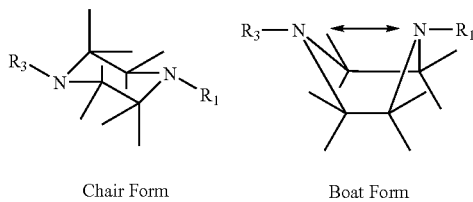

Chair Form                  Boat Form

Furthermore, the nature of the 1, 4 ring nitrogens, and resulting bond angles, is determined by the nature of the $L_1$ and $L_3$ linkers. For example, both nitrogens are in the sp$^3$ configuration if $L_1$ and $L_3$ are of the $(CH_2)_y$ type. In this case, the $R_1$ and $R_3$ groups orient as equatorial groups on the chair configuration and have a high degree of conformational freedom in space due to rotational freedom of C-C single bonds in these groups as shown:

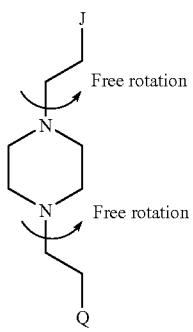

On the other hand both nitrogens exist in the sp$^2$ configuration if $L_1$ and $L_3$ have, for example, an initial carbonyl group, such as a linker unit of the —C(=O)—$(CH_2)_y$— type. In this instance, the carbonyl groups of the ring nitrogen amide functions necessarily exist in one of two rigid forms, similar to cis or trans amide forms. This specific orientation of the carbonyl groups in turn restricts the orientation of the J and Q groups. Therefore, where $L_1$ and $L_3$ include an initial carbonyl group, the $R_1$ and $R_3$ groups have conformational orientations that are different from those in compounds without ring nitrogen amide functions, as shown below:

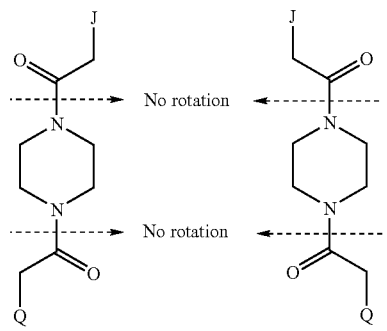

The inventors have surprisingly and unexpectedly found that selective orientation of the $R_1$ group in compounds of this invention, by the means discussed above, causes a shift or change in efficacy, such as determined by functional activity in an adenyl cyclase cell assay, but without significantly influencing receptor binding affinity. For example, compounds described herein where $L_1$, is attached to the ring nitrogen through an amide bond are full agonists with intrinsic activity at MC4-R ranging from 80 to 100% (see the compounds of Examples 38, 42, 43, 44 and 45). However, compounds described herein where $L_1$ is attached through an ethylene group are antagonists or partial agonists with significantly lower intrinsic activity, or have no intrinsic activity, either with or without loss of affinity for MC4-R (see the compounds of Examples 1, 2, 3, 4, 7 and 8).

The substituents at position 5 and 6 of the piperazine ring also have a significant influence on the orientation of the $R_1$ and $R_3$ groups. For example an $R_4$ group in the general structure of this invention influences the spatial preference of the $R_3$ group, and likewise an $R_5$ group influences the spatial preference of the $R_1$ group. The major influence of these groups on biological activity is seen in a stereo-specific manner. For example, the presence of an $R_5$ substituent, such as methyl or isobutyl, in an (S)-configuration cause severe steric constraint on the J group in compounds where $L_1$ is a —$(CH_2)_y$— linker unit. This is because both J as well as the (S)-configuration of the $R_5$ group are positioned in a close chemical space. Steric hindrance between these two groups causes perturbations in the overall orientation of the $R_1$ group, resulting in a structure that is less conducive to receptor affinity and functional efficacy of the compounds. Typically, a 5-15 fold loss of MC4-R affinity has been observed. Similarly, in compounds where $L_1$ is a —C(=O)—$(CH_2)_y$— linker, the incorporation of an (S)-configuration of the $R_5$ group causes the amide carbonyl to position away from the $R_5$ group, again with a similar potential of steric interaction with J group. However, positioning of the $L_1$ carbonyl towards an (S)-configuration of the $R_5$ group is not possible due to severe steric interactions between these groups. These three situations can be shown as:

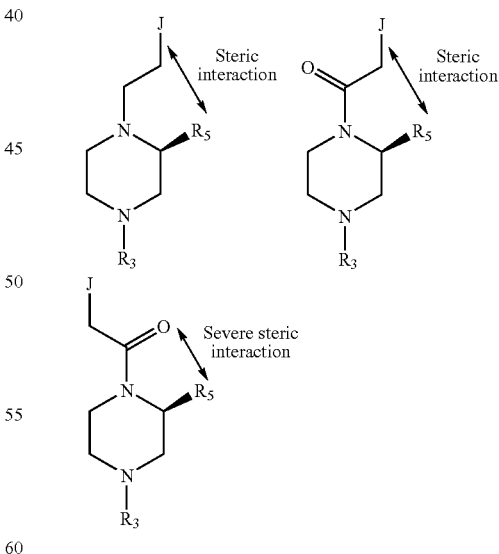

By contrast, incorporation of an $R_5$ substituent, such as methyl or isobutyl, in an (R)-configuration positions the $R_5$ group away from the $R_1$ group. Since there is no perturbation in the positioning of $R_1$ group, this causes no change in MC4-R receptor affinity and selectivity. These structures are shown as follows:

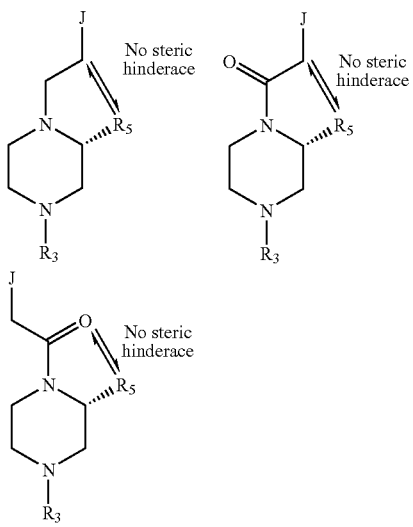

Incorporation of an $R_4$ substituent, such as methyl or isobutyl in either the (R)- or (S)-configuration at the position 6 of the piperazine ring cause severe steric constraint on the Q group in compounds where $L_3$ includes a carbonyl, such as a —C(═O)—$(CH_2)_y$— linker. This is because the spatial orientation of Q is already influenced by the presence of an $R_2$ group at the position 2 of the piperazine ring. Furthermore, the (S)-configuration $R_2$ and (R)-configuration $R_4$ groups are axially located. These groups have 1,3-diaxial steric interactions that distort the chair conformer of the piperazine ring. The $R_4$ group in its equatorial (S)-configuration form causes severe steric interaction with the carbonyl of the $L_3$ linker, as well as the Q group when $L_3$ is a linker unit such as —$(CH_2)_y$—. Therefore, incorporation of an $R_4$ group in either sterochemical orientation leads to compounds that have somewhat weaker receptor affinity (typically a 5-7 fold decrease has been observed). These three situations can be shown as:

It is evident from the foregoing that the incorporation of $R_4$ and/or $R_5$ groups can be employed to modify the functional efficacy of these high-affinity melanocortin compounds. These findings may be used, as described herein, to develop compounds that are agonists, weak partial agonists, mixed agonist-antagonists, antagonists or have no intrinsic activity, and which have utility as agents for modulation of energy homeostasis and feeding responses in mammals.

Steric interaction may be shown by reference to FIG. 1, showing the structure of a hypothetical compound wherein $R_1$ and $R_3$ are each phenylacetyl, $R_2$ is (S)-3-aminopropyl, and $R_5$ is (S)-isobutyl (FIG. 1A) or (R)-isobutyl (FIG. 1B). As may be seen from FIG. 1, there is significant steric interaction with (S)-isobutyl (FIG. 1A) where $L_1$ includes a carbonyl, but not with (R)-isobutyl.

Compounds which bind with high affinity, but which have low or no instrinsic activity, are illustrated by compounds of the following general structure which are disclosed herein.

| Ex. | $R_5$ | $R_4$ | MC1-R | MC3-R | MC4-R | MC5-R | Ratio (MC1-R/ MC4-R) | Intrinsic efficacy MC4-R |
|---|---|---|---|---|---|---|---|---|
| | | | | | Ki (nM) | | | |
| — | H | H | 1198 | 97 | 3 | 259 | 399 | 37% |
| 1 | H | (R)-$CH_3$ | 1309 | 366 | 15 | 727 | 87 | 3% |
| 4 | H | (S)-$CH_3$ | 3185 | 551 | 21 | 602 | 152 | 11% |
| 2 | (R)-$CH_3$ | H | 1134 | 95 | 2 | 362 | 567 | 3% |
| 3 | (S)-$CH_3$ | H | 673 | 362 | 14 | 723 | 48 | 6% |
| 8 | (R)-iso-Butyl | H | 1364 | 87 | 4 | 160 | 341 | 0% |
| 7 | (S)-iso-Butyl | H | 5895 | 495 | 48 | 695 | 123 | 4% |

The initial compound, wherein $R_5$ and $R_4$ are H, is disclosed as Example 129 in PCT/US02/25574, entitled Peptidomimetics of Biologically Active Molecules, filed on Aug. 12, 2002, and incorporated herein by reference. In the foregoing table, intrinsic efficacy or activity less than about 10% is not distinguishable from no intrinsic activity. Thus, for example, the compound of Example 8 binds with high affinity (4 nM) at MC4-R, but has no intrinsic activity. The compound of Example 8 is accordingly inactive as to MC4-R in terms of agonist/antagonist status with respect to NDP-α-MSH.

Synthetic Schemes. Distinct and separate methods for synthesis of piperazines and ketopiperazines are required. In many synthetic schemes, piperazine molecules as described herein cannot be obtained from ketopiperazine molecules or synthetic schemes as described herein. One obvious limitation to employing ketopiperazine synthetic schemes to synthesize piperazine molecules is that the presence of other reactive groups, such as amide, halogen and aromatic functional groups, can interfere with the process of reducing a ketopiperazine to a piperazine. Thus separate and different methods for the synthesis of piperazines were developed and are disclosed herein. Similarly, separate methods for the synthesis of ketopiperazines were also developed and are disclosed here.

One general strategy for either class of compounds includes developing a linear intermediate using chiral building blocks such as amino acid derivatives. The linear intermediate can be cyclized using a Mitsunobo reaction strategy (Mitsunobo, O. The use of diethyl azodicarboxylate and triphenylphosphine in synthesis and transformation of natural products. *Synthesis* 1:1-28 (1981)), or by spontaneous cyclization through reactive groups such as a reaction between an amine and an aldehyde functional group or an amine and an ester functional group. In these cyclizations, the driving force for intramolecular reaction versus intermolecular reaction is the thermodynamically favored reaction forming a six-membered ring structure.

Scheme 4 presented hereafter is an example of a Mitsunobo reaction mediated cyclization. This methodology incorporates conditions that do not involve inversion or racemization of chiral centers, other than inversion of the chiral center on the carbon to which an —OH group is attached.

The methods disclosed herein thus allow for the synthesis of piperazine as well as ketopiperazine molecules with the diverse functionalities disclosed herein. Certain of the schemes further provide a facile approach to obtain compounds that differ at $R_3$ since this group is introduced after the cyclic intermediate has been synthesized.

The piperazine compounds of the invention have three stereocenters, such that at each of three distinct carbon atoms the molecule can assume any permissible sterochemical configuration, such that eight distinct stereo configurations ($2^n$ where n is 3) are both possible and contemplated in this invention. Thus the invention includes compounds with stereo configurations as set forth below (where X is $CH_2$ or C=O). It is further understood that for the $R_2$, $R_4$ and $R_5$ positions, as heretofore defined, where a group other than hydrogen is provided for such position, that the position includes such group in one of $R_{xa}$ or $R_{xb}$, and hydrogen in the remaining of $R_{xa}$ or $R_{xb}$. Thus, for example, $R_2$ may be in either the $R_{2a}$ or $R_{2b}$ position, with the remaining position being hydrogen. In one embodiment, $R_{2a}$ is —$(CH_2)_y$—NH—C(=NH)—$NH_2$ and $R_{2b}$ is hydrogen, or vice versa, and so on. It may thus be seen that all possible stereochemical configurations are included within the disclosure of this invention.

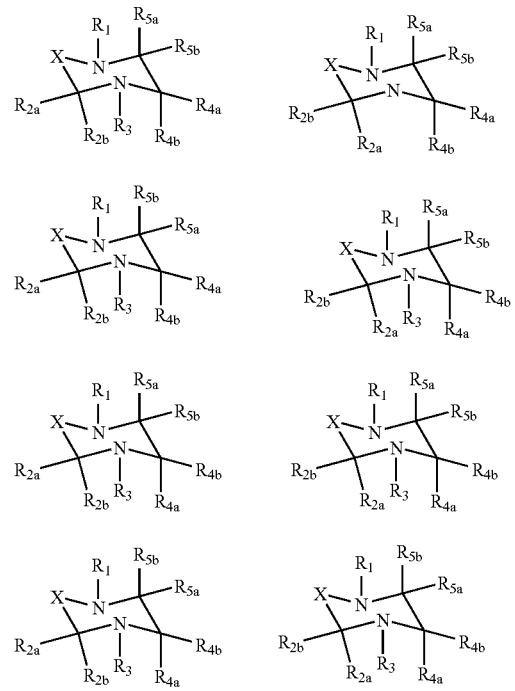

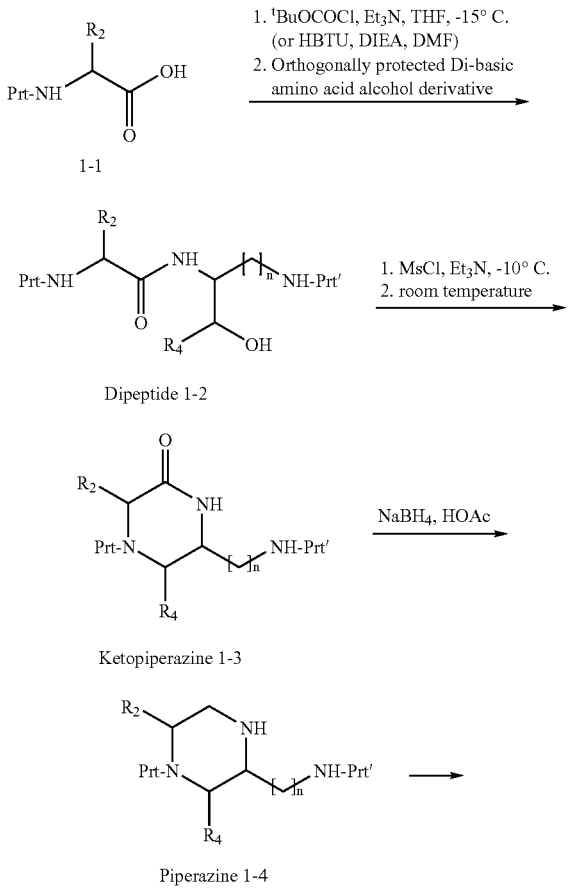

Scheme 1:
Synthesis Of Tetra- And Penta-Substituted Piperazines

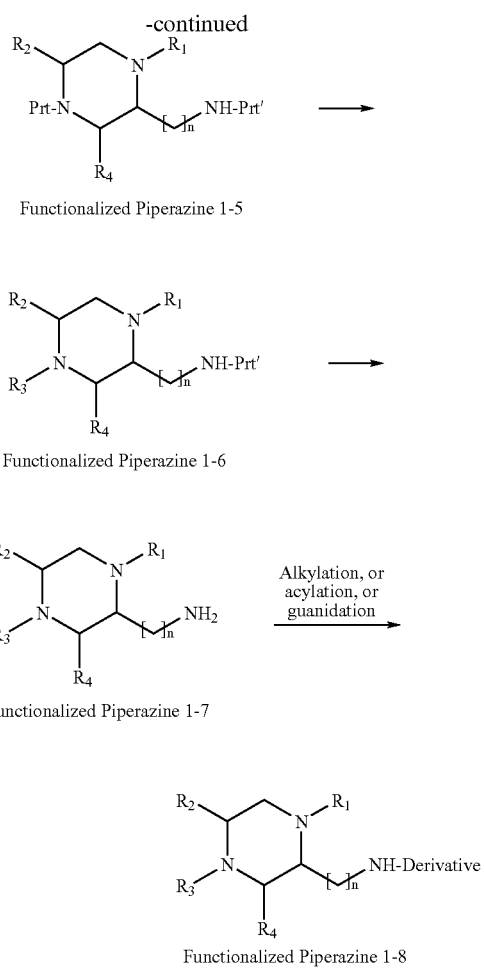

Functionalized Piperazine 1-5

Functionalized Piperazine 1-6

Functionalized Piperazine 1-7

Functionalized Piperazine 1-8

Synthesis of Dipeptide (1-2): The dipeptide (1-2) synthesized in Scheme 1 employs an amino alcohol derivative of a suitable omega-protected alpha omega amino acid. This omega protecting group is orthogonal to the N-Prt group, such that one protecting group can be removed in the presence of the other. 7.8 mL (56 mmol, 1.35 equiv) of TEA was added to a solution of 40 mmol of protected amino acid (1.1) in 200 mL dry THF, kept at −20° C. under $N_2$, followed by the slow addition of 7.2 mL (55 mmol, 1.35 equiv) of IBCF. The reaction mixture was stirred for 5 minutes. 9.4 g (60 mmol, 1.5 equiv) of serine methyl ester hydrochloride or an amino alcohol derivative was added, followed by 8.4 mL (60 mmol, 1 equiv) of TEA, keeping the temperature below −20° C. The reaction mixture was stirred for 30 minutes at −10° C., and then allowed to warm to room temperature. 50 mL of 1 N hydrochloric acid was added, and the layers separated. The organic layer was concentrated, redissolved in 150 mL of EtOAc, and washed with 2×50 mL of 1 N hydrochloric acid, and 1×50 mL saturated sodium bicarbonate solution. The organic layer was dried over magnesium sulfate and concentrated. The dipeptide (1-2) was purified by silica gel chromatography as necessary.

Alternate Synthesis of Dipeptide (1-2): The dipeptide can also be prepared by any common peptide synthesis protocol, such as for example using HBTU as the coupling reagent. To a solution of 14.3 mmol of protected amino acid (1-1) in 30 mL of dry dimethylformamide (DMF), kept at room temperature under $N_2$, was added 5.44 g (14.3 mmol, 1 equiv) of HBTU, followed by 7.5 mL (43.1 mmol, 3 equiv) of diisopropylethyl amine (DIEA). The solution was stirred for 5 minutes, and then 2.5 g (16.1 mmol, 1.1 equiv) of serine methyl ester hydrochloride was added in one portion. The solution was stirred at room temperature for 1 hour, diluted with 100 mL of diethyl ether, and washed with 2×50 mL of 1 N hydrochloric acid. The organic layer was dried over magnesium sulfate, and the dipeptide (1-2) purified by silica gel chromatography as necessary.

Synthesis of ketopiperazine (1-3): To a solution of 5.75 mmol of dipeptide (1-2) in 40 mL of dry DCM, kept at −20° C. under $N_2$, was added 1.0 mL (7.5 mmol, 1.3 equiv) of TEA, followed by the slow addition of 530 µL (6.9 mmol, 1.2 equiv) of methanesulfonyl chloride, keeping the temperature below −10° C. The mixture was stirred at −10° C. for 15 minutes, and then allowed to warm to room temperature. It was stirred at room temperature until HPLC showed the reaction was completed. The reaction mixture was then concentrated and partitioned between 25 mL of ether and 25 mL of water. The organic layer was washed with 1×25 mL of water, dried over magnesium sulfate, and concentrated. The product (1-3) was purified by silica gel chromatography as necessary.

Synthesis of piperazine (14): To a solution of 2.9 mmol of ketopiperazine (1-3) in 7 mL of dioxane, kept at room temperature under $N_2$, was added 550 mg (14.5 mmol, 5 equiv) of sodium borohydride, followed by the slow addition of a solution of 820 mL (14.3 mmol, 5 equiv) of acetic acid in 2 mL of dioxane, and the suspension was then refluxed under $N_2$ for 4 hours. The reaction mixture was cooled to room temperature, and then quenched by the slow addition of 1 N hydrochloric acid. The reaction mixture was diluted with 25 mL of EtOAc and 15 mL of water. The layers were separated, and the organic layer was dried over magnesium sulfate. The product (14) was purified by silica gel chromatography as necessary.

Synthesis of functionalized piperazine (1-5): The secondary amine functionality of piperazine (14) was reacted with a carboxylic acid derivative of a desired $R_1$ group (J-COOH) to establish an amide bond. Well-established standard methods of peptide synthesis can be employed. Alternatively, N-functionalization can also be achieved by treating a bromo or iodo derivative of an $R_1$ group (J-Br) with functionalized piperazine.

Synthesis of functionalized piperazine (1-6): The ring N-Prt group from compound (1-5) is removed and the free amine treated with Q-COOH or a corresponding Q-bromide to obtain 1-6.

Synthesis of fully functionalized piperazine (1-7, and 1-8): The NH-Prt' group from the functionalized piperazine (1-6) is removed to give 1-7. The amine function of 1-7 can further be alkylated, guanidinated or acetylated using standard procedures to give compounds of the general structure 1-8. Alkylation can be accomplished by a reductive amination reaction with an aldehyde (for example, formaldehyde) under the conditions described in synthesis of 34, using alkyl bromide (for example, $CH_3$—Br), or acylation using a carboxylic acid ($CH_3$—COOH), with guanidation using triphenylphorphine, DIAD, and 1,3-Bis(tert-butoxycarbonyl)guanidine as reagents followed by removal of Boc groups as described in Scheme 5. A guanidation reaction can also be performed using 1,3-bis(tert-butoxycarbonyl)-2-methyl-2-thiopseudourea (1.1 equiv) and silver nitrate (1.1 equiv) and NMM (2.2 equiv) as reagents in acetonitrile as discussed in Scheme 4.

Scheme 2:
Synthesis Of Tetra- And Penta-Substituted Ketopiperazines

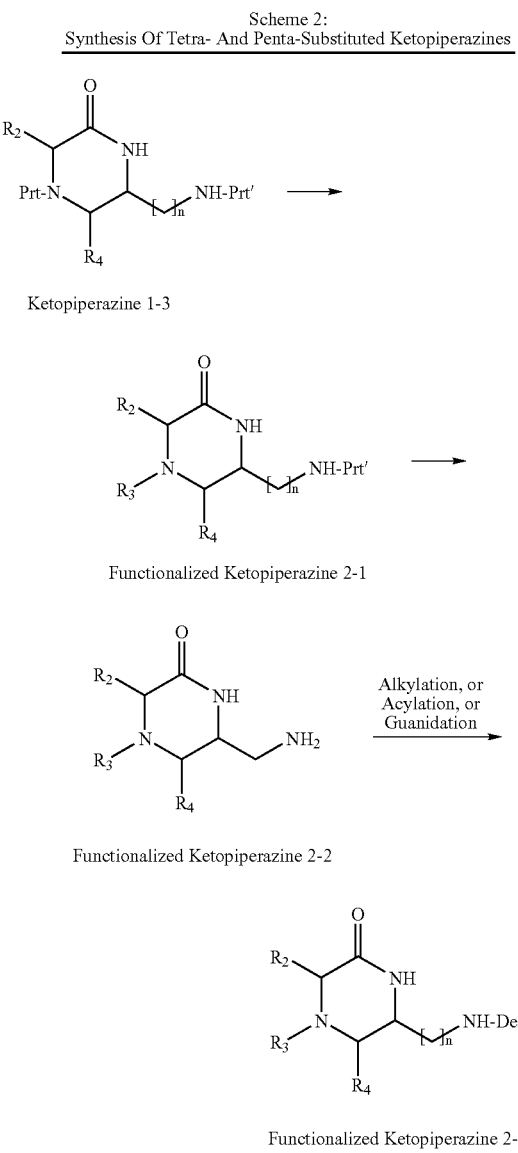

Synthesis of functionalized ketopiperazines (2-2 and 2-3): The NH-Prt' group in ketopiperazine (1-3) is removed and the resulting amine is processed further to introduce an $R_3$ group as generally described for the synthesis of substituted piperazine (1-6) in Scheme 1. The amine function of 2-2 can be introduced to produce compound 2-3 using a similar approach as described for the conversion of 1-7 to 1-8 in Scheme 1.

Scheme 3:
Alternate Synthesis Of Tetra- And Penta-Substituted Piperazines

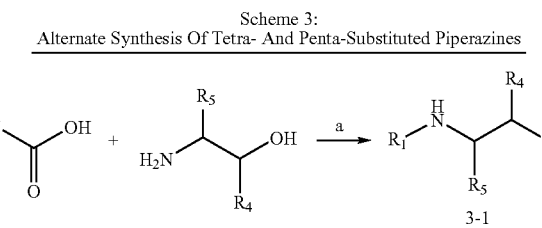

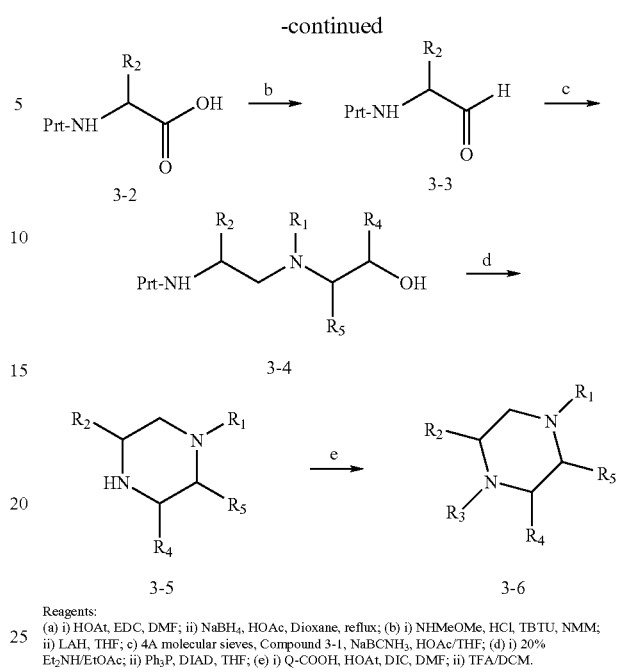

Reagents:
(a) i) HOAt, EDC, DMF; ii) NaBH$_4$, HOAc, Dioxane, reflux; (b) i) NHMeOMe, HCl, TBTU, NMM; ii) LAH, THF; c) 4A molecular sieves, Compound 3-1, NaBCNH$_3$, HOAc/THF; (d) i) 20% Et$_2$NH/EtOAc; ii) Ph$_3$P, DIAD, THF; (e) i) Q-COOH, HOAt, DIC, DMF; ii) TFA/DCM.

To a solution of J-COOH (e.g., naphthylacetic acid) and HOAt (1 equiv) in dry N,N-dimethylformamide was added 1-(3-dimethylaminopropyl)-3-ethylcarbodiimide hydrochloride (1 equiv). After the mixture was stirred at room temperature for one-half hour, a chiral amino alcohol (e.g., (R)- or (S)-1-amino-2-propanol or (R)- or (S)-2-amino-1-propanol, affording a methyl group at $R_5$ or $R_4$, respectively) (1 equiv) was added. The reaction was continued for 16 hours. The reaction mixture was poured into water and extracted by EtOAc twice. The organic layer was washed by 1 N hydrochloric acid twice, 1 N sodium hydroxide twice, brine and dried over sodium sulfate. After evaporation, the product was purified on silica gel column with 10% methanol in methylene chloride.

To this product (1 equiv) and sodium borohydride (5 equiv) in dioxane was added acetic acid (5 equiv) in dioxane slowly. After completion, the mixture was refluxed for 2 hours. The reaction was quenched by water. The product was extracted from ether by 1 N hydrochloric acid. The pH value of the resulting aqueous solution was adjusted with potassium hydroxide to around 11, and the product extracted by ether three times. The organic layer was dried over sodium sulfate and the solvent was evaporated. The obtained compound 3-1 was used for next step reaction without further purification.

To an N-protected amino acid (3-2) (1 equiv), and N-methyl morpholine (1 equiv) in dry DCM was added TBTU (1 equiv). The mixture was stirred at room temperature for 30 minutes. A mixture of N,O-dimethylhydroxyamine hydrochloride (1.5 equiv) and NMM (1.5 equiv) in DCM was stirred for 30 minutes. These two mixtures were combined and stirred at room temperature for 18 hours. The organic solvent was evaporated and the residue loaded on a flash chromatograph column and eluted with EtOAc/hexane (2/1) to yield an N,O-dimethylhydroxyamide product. This product was dissolved in dry THF at 0° C. and LAH (1 M in THF, 1.2 equiv) was added slowly. After 30 minutes the reaction was quenched by aqueous potassium hydrogen sulfate (1.2 equiv). THF was removed and ether was added. The solution was washed by 1 N HCl (2 times), aqueous sodium hydrogen carbonate and brine, and dried over sodium sulfate. The solvent was removed under vacuum to give compound 3-3. Compound 3-3 was used for next step reaction without further purification.

A mixture of compound 3-3 and compound 3-1 was stirred in the presence of activated 4A molecular sieves (1 g) in dry THF (10% acetic acid) for 1 hour. Sodium cyanoborohydride (1 equiv, 1 M solution in THF) was added to this mixture. After 2 hours, solvent was evaporated and the desired product (34) was purified on silica gel column.

Compound 34 was treated with 20% diethylamine in EtOAc for 12 hours, with the solvent evaporated to dryness. The residue and TPP (3 equiv) was dissolved in dry THF. To this solution was added DIAD (3 equiv) in THF slowly at 0° C. The reaction was continued for 16 hours at room temperature. The product 3-5 was purified by silica gel column after evaporation of solvent.

The $R_3$ group was introduced in compound 3-5 by coupling it with an appropriate amino acid (2 equiv), such as D-Phe or a ring-substituted derivative or homolog thereof, by use of HOAt (2 equiv) and DIC (2 equiv) in N,N-dimethylformamide solution overnight at room temperature. Flash chromatograph (EtOAc/hexane=2) gave the product with protecting groups. The Fmoc group was removed by treatment with 20% diethyl amine in EtOAc, and the Boc group was removed by treatment with 30% TFA in methylene chloride for 1 hour, as applicable to the compounds. The final pure compounds (3-6) were obtained by purification on HPLC.

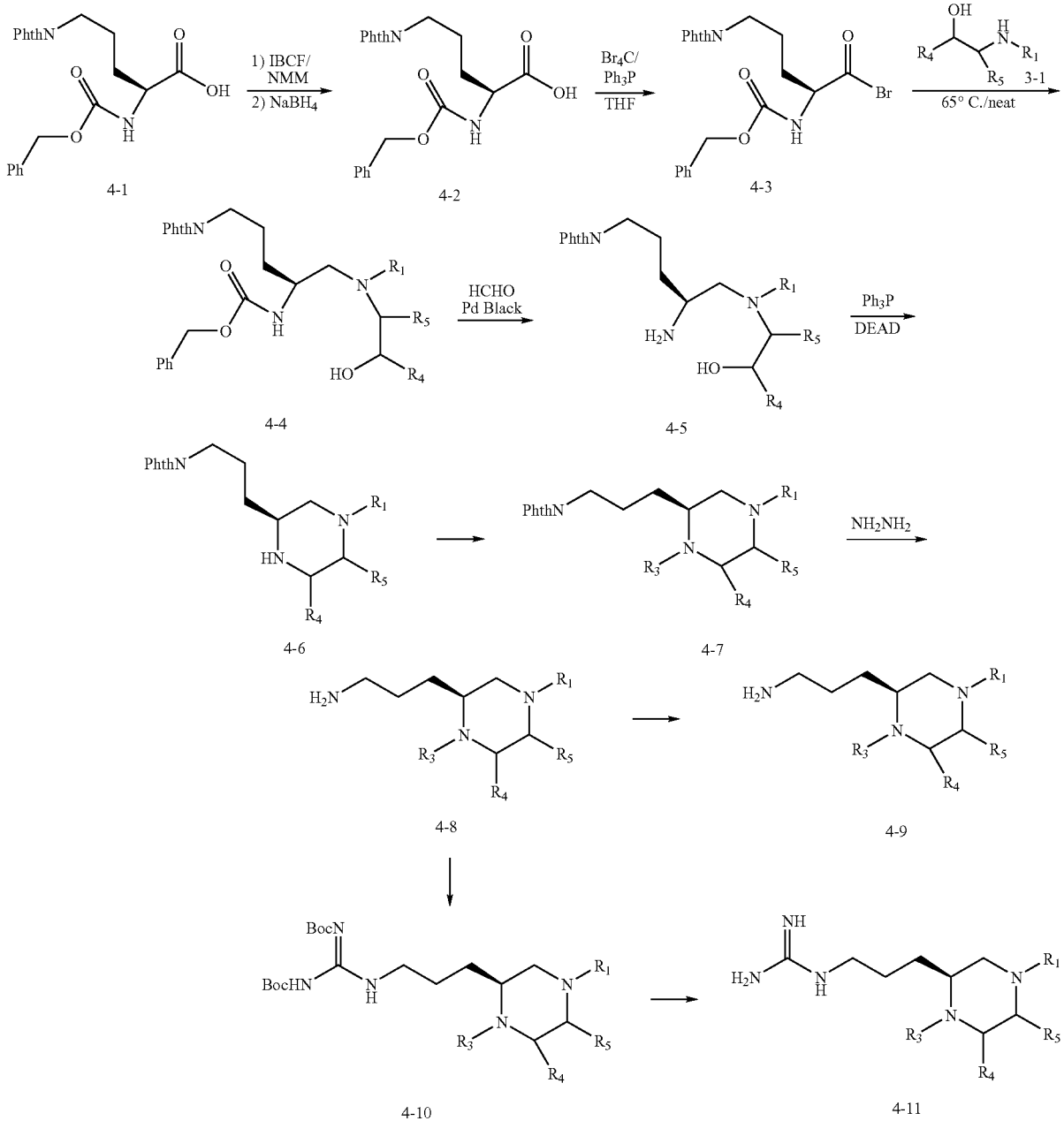

Scheme 4: Alternative Synthesis Of Piperazines

2-Benzyloxycarbonylamino-5-phthalimido-pentanoic acid (4-1) was synthesized from a mixture of Z-ornithine (1 equiv). N-carethoxy-phthalimide (1 equiv), and TEA (1.2 equiv) in dry THF and refluxed overnight. The solvent was evaporated in vacuo, the residue dissolved in EtOAc, and washed successively with 1 N HCl, water, brine, dried (MgSO$_4$) and evaporated in vacuo to afford the crude product, which was used for the next reaction without further purification.

The crude product (4-1) was dissolved in 5 mL of THF and to the solution was added NMM (1 equiv). The solution was cooled to −15° C. with a salt-ice bath, and IBCF (1 equiv) added. After 10 minutes, the reaction mixture was filtered to remove formed solid salt. The solid was washed twice with adequate amounts of THF. The filtrate was cooled to −10° C. and to it was added NaBH$_4$ (1.5 equiv) in water. The reaction mixture was stirred for another 15 minutes, and then concentrated in vacuo. The residue was dissolved in EtOAc and washed successively with 10% citric acid, saturated NaHCO$_3$, H$_2$O and saturated NaCl, and then dried (MgSO$_4$) and concentrated in vacuo. The crude product was purified with column chromatography eluted with 1:1 EtOAc:hexanes. The purified product, [4-Phthalimido-1-hydroxymethyl-butyl]-carbamic acid benzyl ester (4-2), is obtained as a white solid.

At −20° C. under N$_2$ to the suspension of 4-2 and TPP (1.5 equiv) in toluene was added tetrabromocarbon (1.1 equiv) and the reaction mixture stirred at room temperature overnight. The reaction mixture was concentrated in vacuo and the crude product purified by column chromatography eluted with hexanes and EtOAc (2:1). The purified product, [1-Bromomethyl-4-phthalimido-butyl]-carbamic acid benzyl ester (4-3), was obtained as a white solid.

A mixture of 4-3 and an aminoalcohol (3-1) synthesized according to Scheme 3 (2 equiv) in DCM was stirred at 65° C. The solvent was evaporated and the dried reaction mixture heated at 65° C. for 2 hours. The formed crude product was purified by column chromatography and eluted with hexanes (EtOAc 1:2) to give 44.

At room temperature under nitrogen a mixture of 4-4 (0.41 mmol) and palladium black (80 mg) in 21 mL of 4% HCHO in methanol is stirred vigorously for 1 hour. The reaction mixture is filtered and the filtrate neutralized with saturated NaHCO$_3$. The methanol is evaporated and the residue dissolved in EtOAc and washed successively with saturated NaHCO$_3$, water and saturated NaCl, then dried (MgSO$_4$) and evaporated. The product 4-5 is collected as a white solid.

At 0° C. under nitrogen to the mixture of 4-5 and TPP (1.5 equiv) in anhydrous THF was added diethyl azodicarbonate (1.1 equiv) in anhydrous THF. After stirring at room temperature for 4 hours, the reaction mixture was evaporated in vacuo and the crude product purified by column chromatography. The product 4-6 was obtained.

To a mixture of 4-6 (1 equiv), a desired carboxylic acid or appropriate protected amino acid residue, including without limitation ring-substituted D-Phe analogs and homologs (2 equiv), and HOAt (2 equiv) in DMF was added diisopropyl-carboimide (2 equiv). The reaction mixture was stirred at room temperature overnight. The solvent was evaporated in vacuo and the crude product purified by column chromatography (eluted with hexanes, EtOAc 1:2). The purified product 4-7 was obtained as a white solid.

A solution of 4-7 in 10 mL of 0.2 M hydrazine in methanol was stirred at room temperature for 19 hours. Mass spectroscopy showed no starting material left in the reaction mixture. The reaction mixture was evaporated and co-evaporated three times with methanol and once with EtOAc, then dried under high vacuum for 2 days. The crude product 4-8 was used for the next reaction without further purification. 10 mg of the crude product 4-8 was treated with 3 mL of 33% TFA in DCM at room temperature for 2.5 hours. The solvent was removed by evaporation and the crude product purified by HPLC (10-90-60, in an acetonitrile-water gradient flow). After lyophilization of the collected fractions, the product 4-9 was obtained as white solid.

Alternatively, the crude product 4-8 was reacted with 1,3-bis(tert-butoxycarbonyl)-2-methyl-2-thiopseudourea (1.1 equiv) and silver nitrate (1.1 equiv) and NMM (2.2 equiv) in 5 mL of acetonitrile at room temperature for 24 hours, followed by evaporation to remove the solvent and column chromatography purification to produce the 4-10. Product 4-10 was treated with 33% TFA in DCM at room temperature for 2 hours and the reaction mixture concentrated and purified with HPLC to give the final compound 4-11.

Scheme 5:
Alternative Synthesis Of Tetra-Substituted Piperazines

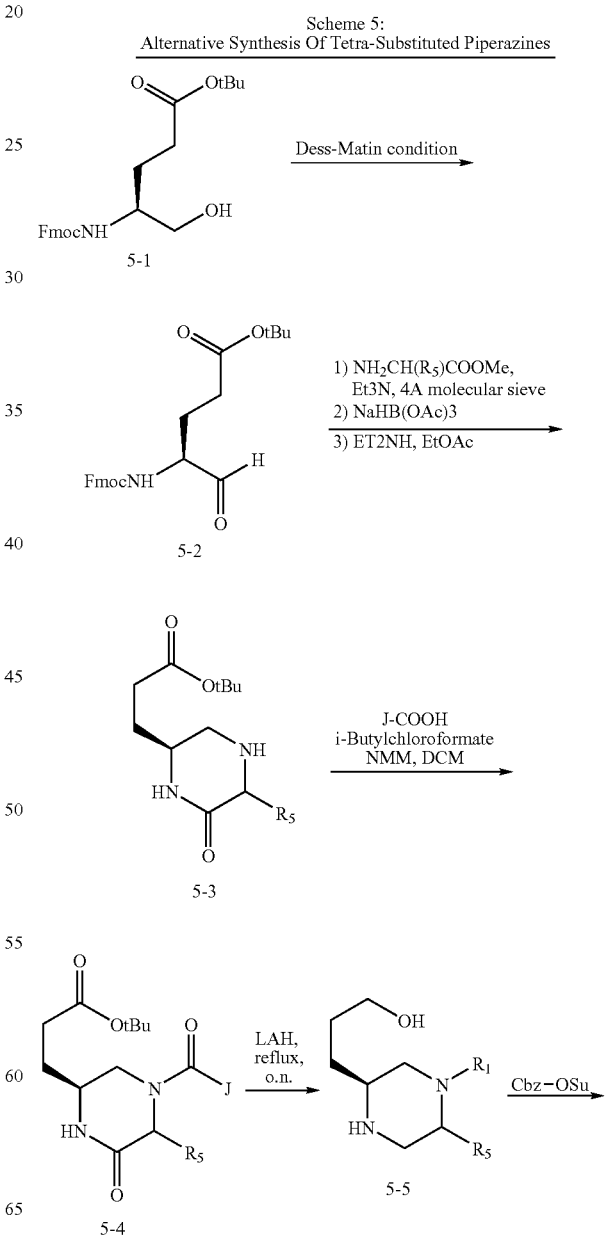

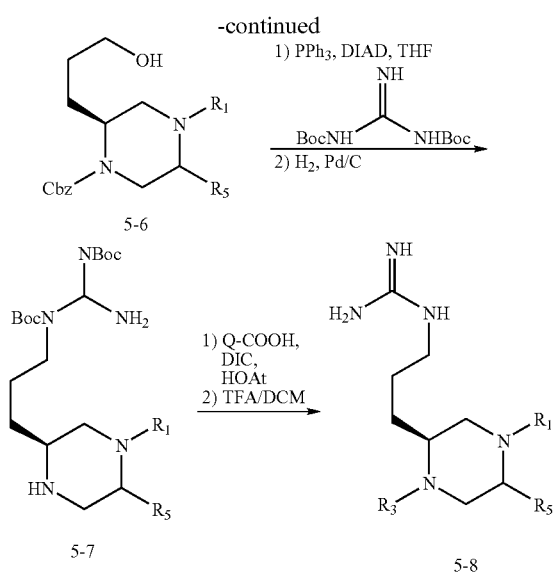

To a solution of compound Fmoc-Glutamol(OBut) (5-1) in DCM was added 1,1,1-triacetoxy-1,1-dihydro-1,2-benziodoxol-3(1H)-one (1.1 equiv) in portions. After stirring for 30 minutes at room temperature, the solution was diluted by ether, followed by addition of 25% sodium thiosulphate in an aqueous solution saturated with sodium bicarbonate. The mixture was stirred for an additional 5 minutes and the desired compound was extracted by EtOAc. The organic layer was washed by saturated bicarbonate solution, water and subsequently dried over magnesium sulfate. After evaporation of solvent, compound 5-2 was obtained for the next step reaction without further A mixture of compound 5-2, (R)- or (S)-amino acid methyl ester (1 equiv), or another selected amino acid methyl ester, such as an alpha amino acid with its side chain appearing as $R_5$ in the final compound 5-8, and TEA (1 equiv) in the presence of a 4 Å molecular sieve in dry THF was stirred for two hours. After addition of sodium triacetoxyborohydride (1.5 equiv) the mixture was stirred for an additional 16 hours. The solid was removed by filtration and the product extracted by EtOAc from water. The organic layer was dried over sodium sulfate. After evaporation of solvent the residue was dissolved in EtOAc containing 20% diethylamine. The reaction was carried out for 16 hours and solvent removed under vacuum. The product 5-3 was obtained after purification by chromatography.

To a solution of a desired carboxylic acid (1 equiv), or a related acid constituting itself as $R_1$ in the final compound 5-8, and N-methylmorpholine (1 equiv) in DCM at –15° C. was added isopropyl chloroformate (1 equiv) slowly. The reaction mixture was stirred for 30 minutes and compound 5-3 was subsequently added. After 30 minutes the reaction temperature was raised to room temperature and the mixture was stirred for 16 hours. The solvent was evaporated and the residue was purified on column to yield compound 54.

To the solution of compound 54 in THF was added LAH (in THF, 4.5 equiv) slowly. The reaction was conducted at room temperature for 2 hours and refluxing temperature for 16 hours. After cooling, the reaction mixture was treated with water, 15% sodium hydroxide and subsequently water. The white solids were removed by filtration and solvent was evaporated. The residue contained compound 5-5, which was used for the next step reaction without further purification.

Compound 5-5 and N-(benzyloxylcarbonyloxy)succinimide (1.5 equiv) was dissolved in acetonitrile. The mixture was stirred for 16 hours. The solvent was evaporated and residue was re-dissolved in methanol. To this solution was added 1 N sodium hydroxide (1.5 equiv). The mixture was stirred for additional 16 hours. After evaporation of solvent the residue was purified on column to yield compound 5-6.

To a mixture of compound 5-6, triphenylphorphine (3 equiv) and 1,3-Bis(tert-butoxycarbonyl)guanidine (3 equiv) in toluene was added DIAD (3 equiv) slowly at 0° C. The reaction mixture was stirred for 16 hours at room temperature. After evaporation of solvent the residue was purified on a column to give the desired compound. This compound was subject to treatment with hydrogen in the presence of a catalytic amount of palladium on carbon (10%) in methanol. After 16 hours the solvent was evaporated and the residue was purified on a column to give compound 5-7.

Compound 5-7 was coupled with desired amino acids (2 equiv) by use of HOAt (2 equiv) and DIC (2 equiv) in N,N-dimethylformamide solution overnight at room temperature to introduce the desired $R_3$ moiety in the molecule. Flash chromatograph gave the product with protecting groups. The Fmoc group was removed by treatment with 20% diethyl amine in EtOAc and the Boc group was removed by treatment with 30% TFA in methylene chloride for 1 hour, as applicable to the specific compounds. The final pure compound (5-8) was obtained by purification on HPLC.

The alkyl groups on the amino group of D-4-Cl-phenylalanine moiety in Examples 31, 32, 33 and 34 were introduced by reductive amination as described for the synthesis of compound 3-4.

Scheme 6:
Alternative Synthesis Of Tetra-Substituted Piperazines

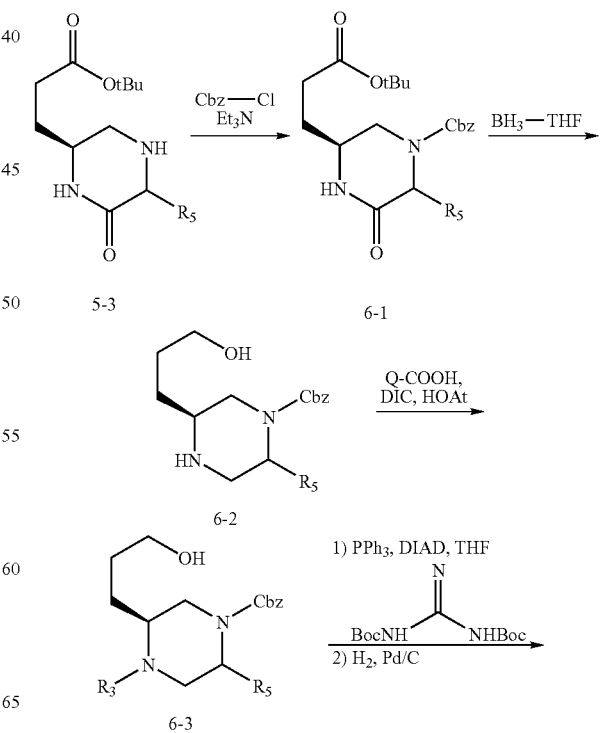

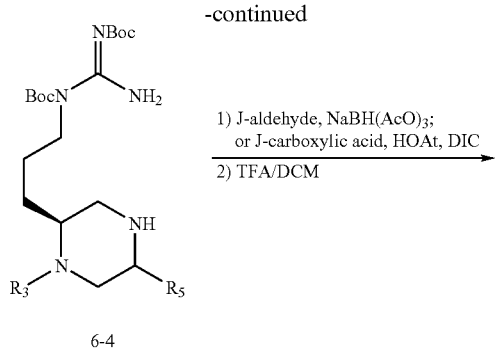

6-4

To a solution of compound 5-3 and TEA (1 equiv) in DCM at 0° C. benzyl chloroformate (1 equiv) was added slowly. The reaction was carried out overnight. After evaporation of solvent the product was purified on column to give 6-1.

Compound 6-1 was dissolved in dry THF, to which borane in THF (1 M solution, 5 equiv total) was added. This solution was stirred for 16 hours. The reaction was quenched with 1 N HCl and the solution was subsequently neutralized by 1 N NaOH. The product was extracted by EtOAc and the organic layer was washed by water, brine and dried over sodium sulfate. The solvent was evaporated and the dried product 6-2 was used for next step reaction.

Compound 6-2 was coupled with desired amino acids (1.5 equiv) by use of HOAt (1.5 equiv) and DIC (1.5 equiv) in N,N-dimethylformamide solution overnight at room temperature. Flash chromatograph gave the product with protecting groups (6-3).

To a mixture of compound 6-3, triphenylphorphine (3 equiv) and 1,3-Bis(tert-butoxycarbonyl)guanidine (3 equiv) in toluene was added DIAD (3 equiv) slowly at 0° C. The reaction mixture was stirred for 16 hours at room temperature. After evaporation of solvent the residue was purified on a column to give the desired compound. This compound was subject to treatment with hydrogen in the presence of a catalytic amount of palladium on carbon (10%) in methanol. After 16 hours the solvent was evaporated and the residue was purified on a column to give compound 6-4. This was reacted in one of the two following different ways to give the final compound:

(a) Reaction of compound 6-4 with J-aldehydes: A mixture of compound 6-4 and J-aldehyde (1 equiv) in the presence of a 4A molecular sieve in dry THF was stirred for two hours. After addition of sodium triacetoxyborohydride (1.5 equiv) the mixture was stirred for an additional 16 hours. The solid was removed by filtration and the solvent was evaporated. The residue was purified on column to give the desired compound with Boc protecting groups.

(b) Reaction of compound 6-4 with J-carboxylic acids: Compound 6-4 was coupled with J-carboxylic acid (1.5 equiv) by use of HOAt (1.5 equiv) and DIC (1.5 equiv) in N,N-dimethylformamide solution overnight at room temperature. Flash chromatograph gave the product with Boc protecting groups.

In either of the foregoing cases, the compounds with Boc groups were subjected to treatment with TFA/DCM (50/50) for one hour. After evaporation of solvent the final compound 6-5 was purified on HPLC.

Scheme 7
Alternative Synthesis Of Tetra-Subsituted Piperazines

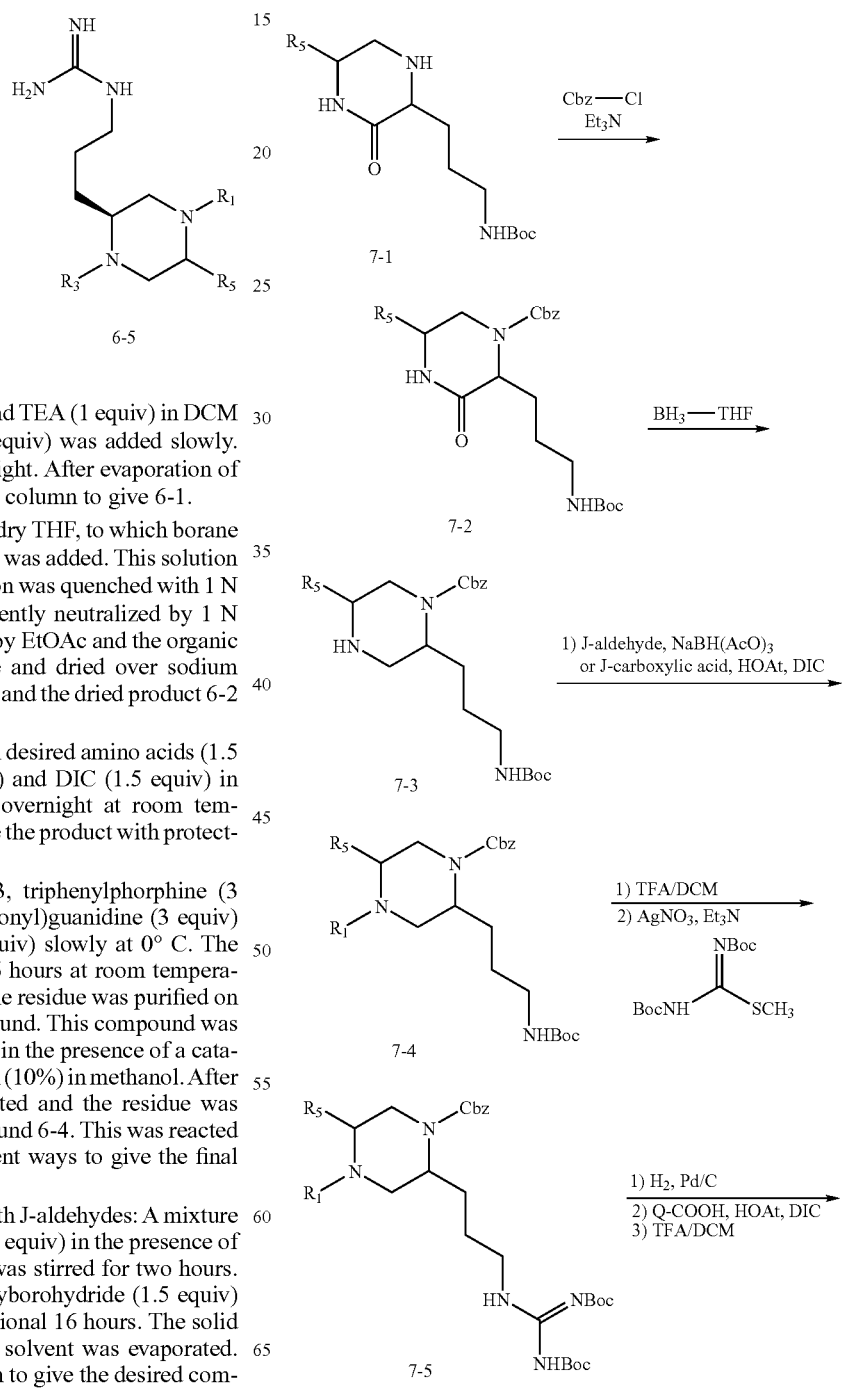

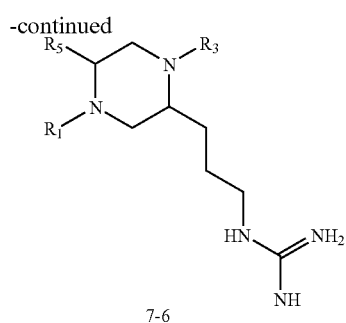

7-6

Compound 7-1 is synthesized by the methods described for compound 5-3. The starting material is an (R)- or (S)-isomer of Fmoc-alaninol. The aldehyde thus obtained is subsequently reacted with Orn(Boc)-OMe under reductive amination conditions, and with cyclization gives compound 7-1 after removal of the Fmoc group. Thereafter compound 7-2 is synthesized by a method similar to that described for compound 6-1; compound 7-3 is synthesized by a method similar to that described for compound 6-2; compound 7-4 is synthesized by a method similar to that described for compound 6-5; and compound 7-5 is synthesized by a method similar to that described for compound 4-10.

Compound 7-5 is treated with hydrogen in the presence of catalytic amounts of palladium on carbon in a suitable solvent at room temperature for 16 hours. After filtration the solvent is evaporated and the resulting compound is processed to give compound 7-6 in a manner similar to that described for synthesis of compound 5-8.

The resulting compound 7-6 illustrates an alternative route for making an enantomeric form of the compounds. However, depending on selection of the chiral starting materials, similar results and other stereoisomers can be obtained by any of the synthetic schemes disclosed.

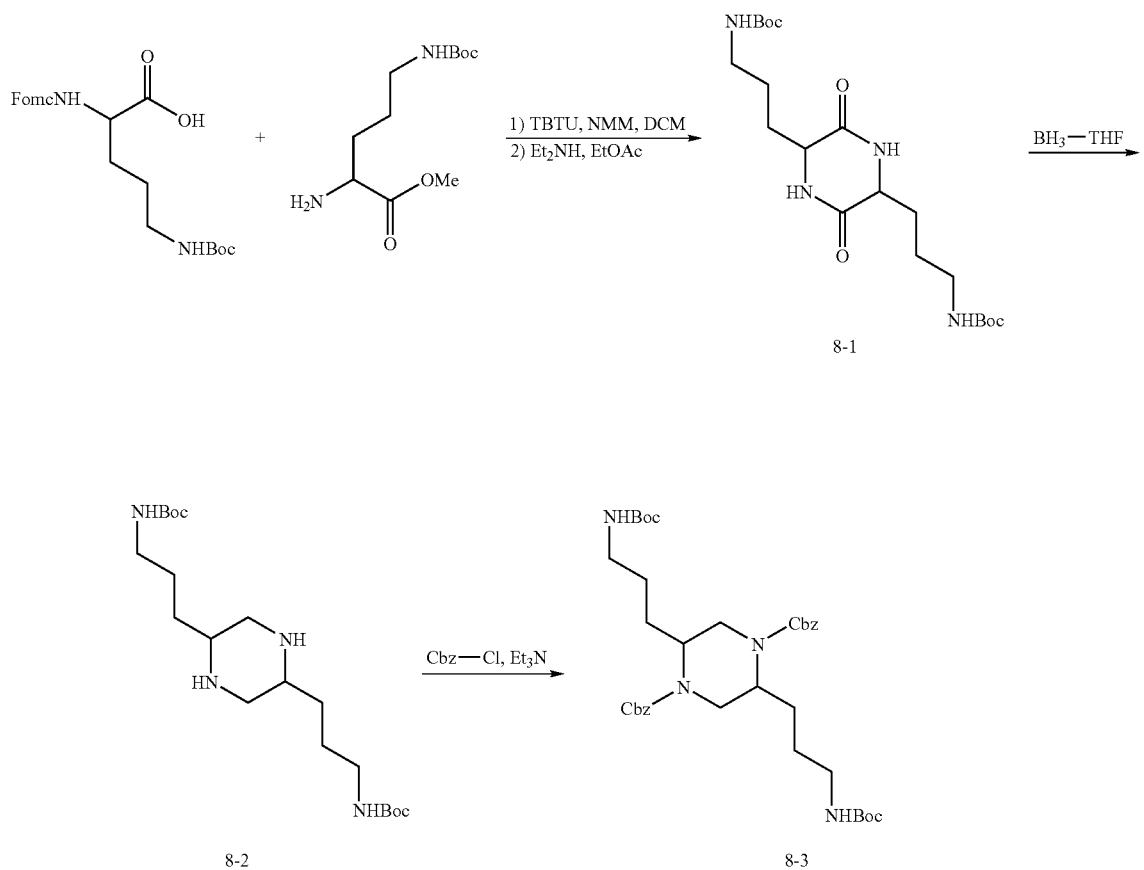

Scheme 8:
Alternative Synthesis Of Tetra-Substituted Piperazines

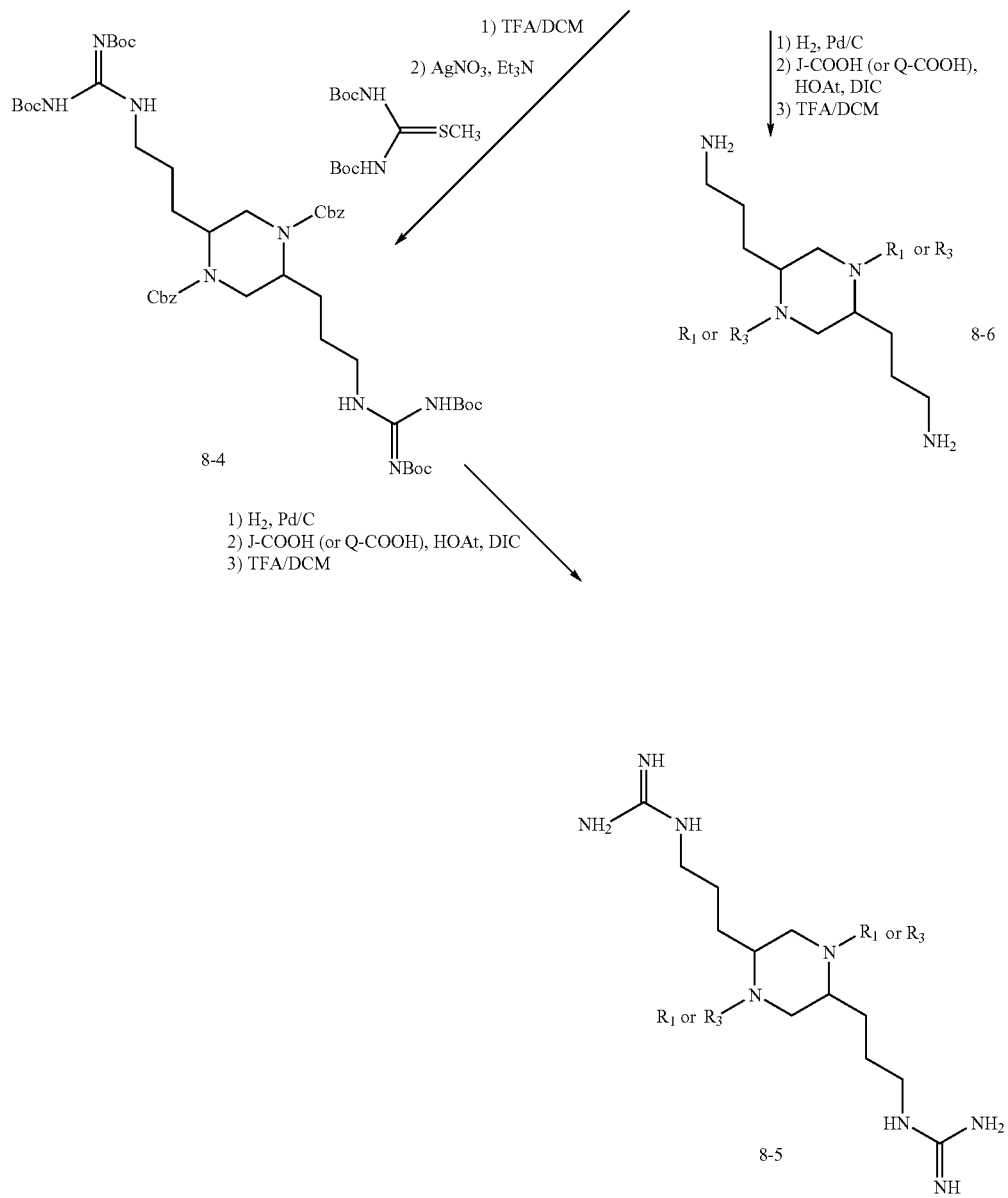

To Fmoc-Orn(Boc)-OH and NMM (1 equiv) in dry DCM is added TBTU (1 equiv). The mixture is stirred at room temperature for 30 minutes. Separately, a mixture of Orn(Boc)-OMe hydrochloride (1 equiv) and NMM (1 equiv) in DCM is stirred for 30 minutes. These two mixtures are combined and stirred at room temperature for 16 hours. The organic solvent is evaporated and the residue is extracted by EtOAc. The organic layer is washed by 1 N NaOH, water, 1 N HCl, water, and brine and then dried over sodium sulfate. After removal of the solvent the compound is treated with 20% diethyl amine in EtOAc for 16 hours. The solvent is evaporated and the residue is purified on column to give compound 8-1. Thereafter, compound 8-2 is synthesized by a method similar to that described for compound 6-2; compound 8-3 is synthesized by a method similar to that described for compound 6-1; compound 8-4 is synthesized by a method similar to that described for compound 4-10; and compound 8-5 is synthesized by a method similar to that described for compound 7-6. Alternatively, 8-3 can be processed directly to 8-6 as shown to get compounds that have amino groups instead of guanidines.

Compound 8-5 and 8-6 thus has two identical $R_1$ groups, or alternatively has two identical $R_3$ groups, and further has two identical $R_2$ groups. Compounds of Scheme 8 are thus special cases of the general formula, in which the group corresponding to $R_5$ is identical to the group corresponding to $R_2$.

Scheme 9:
Alternative Synthesis Of Tetra-Substituted Piperazines
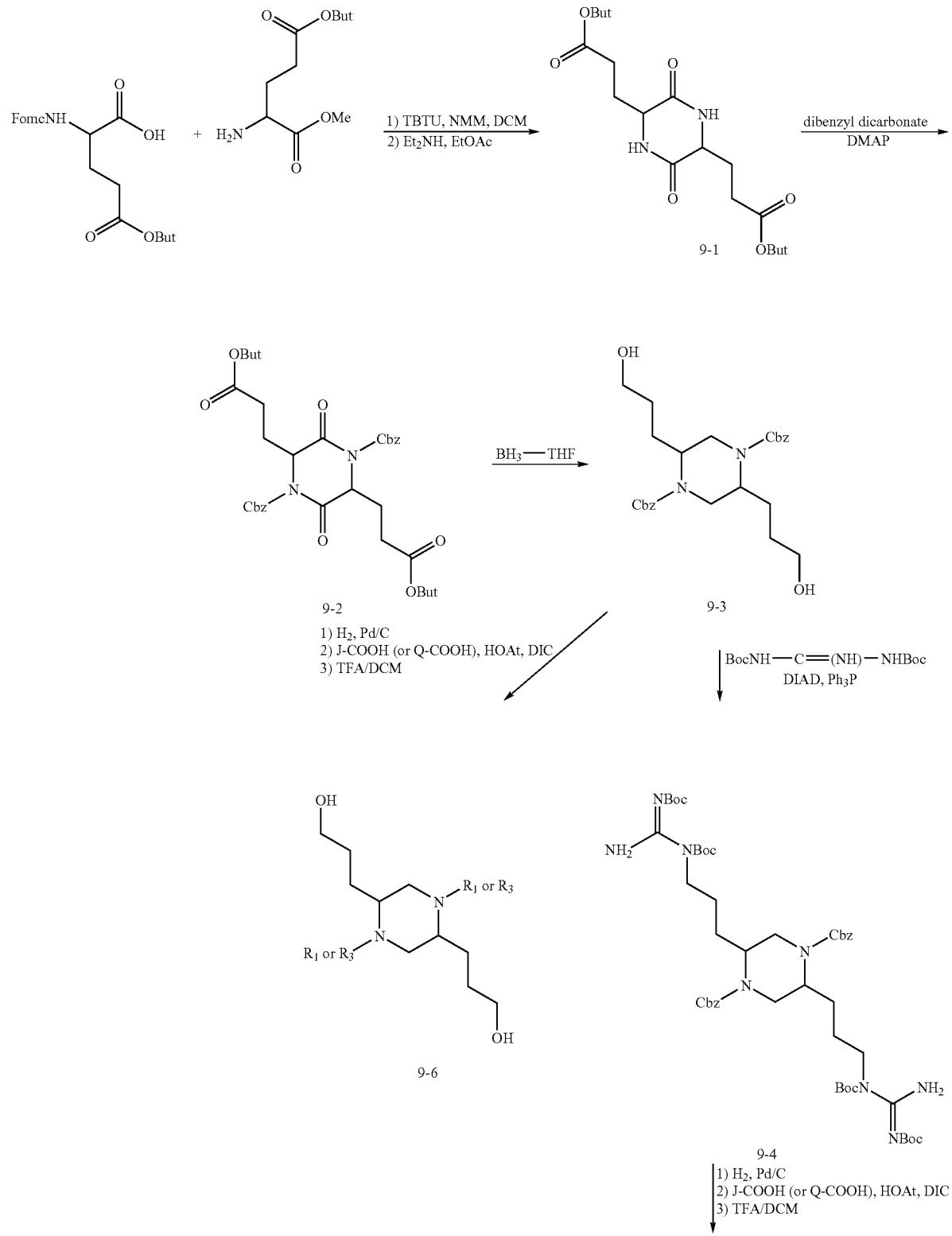

-continued

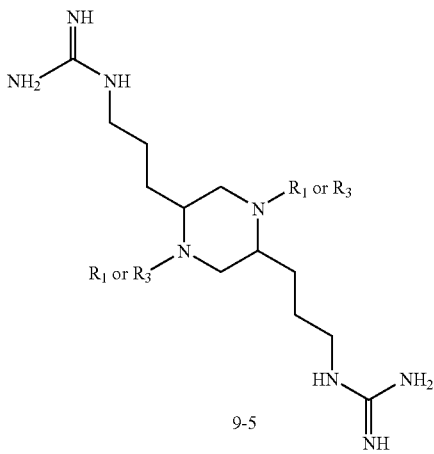

9-5

To Fmoc-Glu(Boc)-OH and NMM (1 equiv) in dry DCM is added TBTU (1 equiv). The mixture is stirred at room temperature for 30 minutes. Separately, a mixture of Glu(Boc)-OMe hydrochloride (1 equiv) and NMM (1 equiv) in DCM is stirred for 30 minutes. These two mixtures are combined and stirred at room temperature for 16 hours. The organic solvent is evaporated and the residue is extracted by EtOAc. The organic layer is washed by aqueous sodium bicarbonate, water, 1 N HCl, water, and brine and then dried over sodium sulfate. After removal of the solvent the compound is treated with 30% diethyl amine in EtOAc for 5 hours. The solvent is evaporated and the residue is dissolved in DMF and the solution is heated at 60° C. for 16 hours. The solvent is evaporated and the solid is washed by EtOAc. The collected solid 9-1 is dried under vacuum and used for the next step reaction.

To the solution of 9-1 in DMF was added 4-dimethylaminopyridine (2 equiv) and dibenzyl dicarbonate (2 equiv). The reaction is carried out for 16 hour at room temperature. After removal of solvent the residue is purified on silica gel column to give product 9-2.

Compound 9-3 is synthesized by a method similar to that described for compound 6-2.

Compound 94 is synthesized by a method similar to that described for compound 64.

Compound 9-5 is synthesized by a method similar to that described for compound 7-6.

Alternatively 9-3 can be processed in a manner similar to synthesis of compound 9-5 from 94 to give 9-6.

Compounds 9-5 and 9-6 thus has two identical $R_1$ groups, or alternatively has two identical $R_3$ groups, at the $R_1$ and $R_3$ positions, and further has two identical $R_2$ groups, at the $R_2$ and $R_5$ positions. Compounds of Scheme 9 are thus special cases of the general formula, in which the group corresponding to $R_5$ is identical to the group corresponding to $R_2$.

Scheme 10:
Alternative Synthesis Of Ketopiperazines

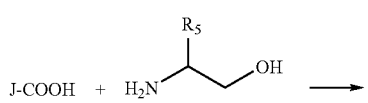

-continued 10-1

10-2

10-3

10-4

10-5

To a solution of carboxylic acid and HOAt (1 equiv) in dry N,N-dimethylformamide is added 1-(3-dimethylaminopropyl)-3-ethylcarbodimide hydrochloride (1 equiv). After the mixture is stirred at room temperature for half an hour, 1 or 2-substituted ethanolamine (1.5 equiv) is added. The reaction is continued for 16 hours. The reaction mixture is poured into water and extracted by EtOAc twice. The organic layer is washed by 1 N hydrochloric acid twice, 1 N sodium hydroxide twice, brine and dried over sodium sulfate. After evaporated the solvent the product (10-1) is purified on silica gel column with 10% methanol on methylene chloride.

To compound 10-1 (1 equiv) and sodium borohydride (5 equiv) in dioxane is added acetic acid (5 equiv) in dioxane slowly. After completion the mixture is refluxed for 2 hours. The reaction is quenched by water. The product is extracted from ether by 1 N hydrochloric acid. The pH value of aqueous solution is adjusted with potassium hydroxide to around 11 and the product is extracted by ether three times. The organic layer is dried over sodium sulfate and solvent is evaporated. The obtained compound 10-2 is used for next step reaction without further purification.

An N-protected amino acid (1 equiv), HOAt (1 equiv) and DIC (1 equiv) in N,N-dimethylformamide solution is stirred for half an hour. To this solution is added compound 10-2 and the mixture is stirred overnight. After evaporating solvent, compound 10-3 is obtained by silica gel column purification.

The protecting group Prt (Fmoc or Cbz) is removed by either 20% diethyl amine in EtOAc or by hydrogen catalyzed with 10% palladium on carbon. The resulting compound is dissolved in dry THF with triphenylphosphine (3 equiv). To this solution is added DEAD (3 equiv) in THF slowly. The reaction is stirred for an additional 12 hours. After the solvent is evaporated the product (10-4) is purified on silica gel column.

Compound 10-4 is coupled with desired amino acids (2 equiv) by use of HOAt (2 equiv) and DIC (2 equiv) in N,N-dimethylformamide solution overnight at room temperature. Flash chromatograph gives the product with protecting groups. The Fmoc group is removed by treatment with 20% diethyl amine in EtOAc and the Boc group is removed by treatment with 30% TFA in methylene chloride for 1 hour, as applicable to the compounds. The final pure compound (10-5) is obtained by purification on HPLC.

Assays and Animal Models

Selected compounds were tested in assays to determine binding and functional status, and were tested in animal models of penile erection, feeding behavior and conditioned taste avoidance, as discussed below. The following assays and animal models were employed, with modifications as discussed in the examples.

Competitive inhibition assay. A competitive inhibition binding assay was conducted using membranes prepared from hMC3-R, hMC4-R, hMC5-R, and B-16 mouse melanoma cells (containing MC1-R) using 0.4 nM $^{125}$I-NDP-α-MSH (New England Nuclear, Boston, Mass., USA) in 50 mM HEPES buffer containing 1 mM MgCl$_2$, 2 mM CaCl$_2$, and 5 mM KCl, at pH 7.2. The assay tube also contained a chosen concentration of the test compound of this invention, typically a 1 µM concentration, for determining its efficacy in inhibiting the binding of $^{125}$I-NDP-α-MSH to its receptor. Non-specific binding was measured by complete inhibition of binding or $^{125}$I-NDP-α-MbH in the assay with the presence of 1 µM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 µM α-MSH. The cpm obtained in presence of test compounds were normalized with respect to 100% specific binding to determine the percent inhibition of $^{125}$-NDP-α-MSH binding. Each assay was conducted in triplicate and the actual mean values are described, with results less than 0% reported as 0%.

EC$_{50}$ determination in functional activity assay. The Ki (nM) of certain compounds of the invention were determined. Functional evaluation of compounds at melanocortin receptors was performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM MgCl$_2$, 1 mM glutamine, 0.1% albumin and 0.6 mM 3-isobutyl-1-methyl-xanthine, a phosphodiesterase inhibitor, were plated in 96 well plates at a density of $0.5 \times 10^5$ cells per well. Cells were incubated with the test compounds in the presence or absence of α-MSH for 1 hour at 37° C. cAMP levels were measured by EIA (Amersham) in the cell lysates. Data analysis and EC$_{50}$ values were determined using nonlinear regression analysis with Prism Graph-Pad software.

Functional status. The agonist/antagonist status with respect to MC$_{1-4}$, MC4-R, and MC5-R of certain compounds of the invention was determined. Antagonistic activity was determined by measuring the inhibition of α-MSH-induced or NDP-α-MSH-induced cAMP levels following exposure to the compounds as in the preceding descriptions.

Penile erection induction. The ability of compounds to induce penile erection (PE) in male rats were evaluated with selected compounds. Male Sprague-Dawley rats weighing 200-250 g were kept on a 12 hour on/off light cycle with food and water ad libitum. All behavioral studies were performed between 10 a.m. and 5 p.m. Groups of 4-8 rats were treated with compounds at a variety of doses via intravenous (IV) or intracerebroventricuiar (ICV) routes. Immediately after treatment, rats were placed into individual polystyrene cages (27 cm long, 16 cm wide, and 25 cm high) for behavioral observation. Rats were observed for 30 minutes IV or 90 minutes ICV, and the number of yawns, grooming bouts and PEs were recorded in 10-minute bins.

ICV food intake and body weight change. Change in food intake and body weight was evaluated for selected compounds. Rats with indwelling intracerebroventricular cannulas (ICV rats) were obtained from Hilltop Lab Animals, Inc. (Scottdale, Pa.). Animals were individually housed in conventional plexiglass hanging cages and maintained on a controlled 12 hour on/12 hour off light cycle. Water and powdered (LabDiet, 5P00 Prolab RMH 3000) or pelleted (Harlan Teklad 2018 18% Protein Rodent Diet) food was provided ad libitum. For 1 week before treatment, 24-hour food intake and body weight change was recorded to assess a baseline for the group during vehicle treatment. The rats were dosed ICV with vehicle or selected compounds (1-3 nmol). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

IV food intake and body weight change. Change in food intake and body weight was evaluated for selected compounds. Male Sprague-Dawley rats were obtained from Taconic (Germantown, N.Y.). Animals were individually housed in conventional plexiglass hanging cages and maintained on a controlled 12 hour on/12 hour off light cycle. Water and powdered (LabDiet, 5P00 Prolab RMH 3000) or pelleted (Harlan Teklad 2018 18% Protein Rodent Diet) food was provided ad libitum. For 1 week before treatment, 24-hour food intake and body weight change was recorded to assess a baseline for the group during vehicle treatment. The rats were dosed IV with vehicle or selected compounds (0.5-3 mg/kg). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

Behavioral Satiety Sequence. Male Sprague-Dawley rats were maintained on a restricted 20 g powdered food/day schedule. Food was presented at the same time during the lights on period dosed with either saline or the test compound 2 hours before presentation of food and the start of observation. Pre-weighed bowls (containing 20 g of food) were presented and the behavior of the rats was observed for 1 hour. Behavioral observations were divided into 3 categories: Feeding, Active (includes grooming, drinking and sniffing/exploration), and Resting (decreased activity and sleep). The amount of time spent in each behavior was recorded. The amount of food intake was determined after the observation period.

Conditioned Taste Avoidance. Male Sprague-Dawley rats were adapted to a restricted drinking period of 30 minutes/day during lights on and were provided with pelleted chow ad libitum. In laboratory animals, administration of LiCl conditions an aversion to the novel and favorable taste of saccharin (Seeley R J, Blake K, Rushing P A, Benoit S, Eng J, Woods S C and D'Alessio D: The role of CNS glucagons-like peptide-1 (7-36) amide receptors in mediating the visceral illness effects of lithium chloride. *J. Neurosci.* 20(4):1616-1621, 2000). To condition animals, an injection of LiCl or test compound was administered immediately after the initial presentation of a 0.1% solution of saccharin. Two days later, saccharin solution was again presented and fluid intake was determined. A decrease in drinking the saccharin solution suggests development of a conditioned taste aversion.

Determination of mass and nuclear magnetic resonance analysis. The mass values were determined using a Waters MicroMass ZQ device utilizing a positive mode. Mass determinations were compared with calculated values and expressed in the form of mass weight plus one (M+1 or M+H).

Proton NMR data was obtained using a Bruker 300 MHz spectrometer. The spectra were obtained after dissolving compounds in a deuteriated solvent such as chloroform, DMSO, or methanol as appropriate.

EXAMPLE 1

N-{3-[1-[2(R)-Amino-3-(2,4-dichloro-phenyl)-propionyl]-6(R)-methyl-4-(2-naphthalen-2-ethyl)-piperazin-2(S)-yl]-propyl}-guanidine The following compound was synthesized by the method of Scheme 3 using 2-naphthylacetic acid as J-COOH, (S)-(+)-1-amino-2-propanol as $NH_2$—$CH(R_5)$—$CH(R_4)$—OH, Fmoc-L-Arg(Boc)$_2$-OH as Prt-NH—$C(R_2)$—COOH and Boc-D-2,4-dichloro-Phe-OH as Q-COOH. It was tested as described above with the results shown. The mass was analyzed as 569.4 (M+H).

| MC1-R | MC3-R | MC4-R | MC5-R |
|---|---|---|---|
| Inhibition at 1 µM | | | |
| 14 | 32 | 95 | 36 |
| Ki (nM) | | | |
| 1309 | 366 | 15 | 727 |

In a cAMP assay using MC4-R, at 1 µM concentrations the compound of Example 1 exhibited no intrinsic activity.

EXAMPLE 2

N-{3-[1-[2(R)-Amino-3-(2,4-dichloro-phenyl)-propionyl]-5(R)-methyl-4-(2-naphthalen-2-yl-ethyl)-piperazin-2(S)-yl]-propyl}-guanidine The following compound was synthesized by the methods of both Schemes 3 and 5 using 2-naphthylacetic acid as J-COOH, (R)-(−)-2-amino-1-propanol as $NH_2$—$CH(R_5)$—$CH(R_4)$—OH, Fmoc-L-Arg(Boc)$_2$-OH as Prt-NH—$C(R_2)$—COOH, D-Alanine methyl ester as $NH_2$—$CH(R_5)$—$COOCH_3$ and Boc-D-2,4-dichloro-Phe-OH as Q-COOH. It was tested as described above with the results shown. The mass was analyzed as 569.3 (M+H).

| MC1-R | MC3-R | MC4-R | MC5-R |
|---|---|---|---|
| Inhibition at 1 µM | | | |
| 20 | 72 | 99 | 65 |
| Ki (nM) | | | |
| 1134 | 95 | 2 | 362 |

In a cAMP assay for determination of agonist/antagonist status, it was determined that the compound was an antagonist as to MC4-R.

In ICV feeding studies at 1 nmol dose levels, a 24 hour change in food intake of 2.6 g, and change in weight of −0.3 g, was observed.

EXAMPLE 3

N-{3-[1-[2(R)-Amino-3-(2,4-dichloro-phenyl)-propionyl]-5(S)-methyl-4-(2-naphthalen-2-yl-ethyl)-piperazin-2(S)-yl]-propyl}-guanidine The following compound was synthesized by the method of Scheme 3 using 2-naphthylacetic acid as J-COOH, (S)-(+)-2-amino-1-propanol as $NH_2$—$CH(R_5)$—$CH(R_4)$—OH, Fmoc-L-Arg(Boc)$_2$-OH as Prt-NH—$CH(R_2)$—COOH, and Boc-D-2,4-dichloro-Phe-OH as Q-COOH. It was tested as described above with the results shown. The mass was analyzed as 569.3 (M+H).

| MC1-R | MC3-R | MC4-R | MC5-R |
|---|---|---|---|
| Inhibition at 1 μM | | | |
| 6 | 40 | 95 | 425 |
| Ki (nM) | | | |
| 673 | 362 | 14 | 723 |

In a cAMP assay using MC4-R, at 1 μM concentrations the compound of Example 3 exhibited no intrinsic activity.

EXAMPLE 4

N-{3-[1-[2(R)-Amino-3-(2,4-dichloro-phenyl)-propionyl]-6(S)-methyl-4-(2-naphthalen-2-yl-ethyl)-piperazin-2(S)-yl]-propyl}-guanidine The following compound was synthesized by the method of Scheme 3 using 2-naphthylacetic acid as J-COOH, (R)-(−)-1-amino-2-propanol as $NH_2$—$CH(R_5)$—$CH(R_4)$—OH, Fmoc-L-Arg(Boc)$_2$-OH as Prt-NH—$CH(R_2)$—COOH, and Boc-D-2,4-dichloro-Phe-OH as Q-COOH. It was tested as described above with the results shown. The mass was analyzed as 569.0 (M+H).

| MC1-R | MC3-R | MC4-R | MC5-R |
|---|---|---|---|
| Inhibition at 1 μM | | | |
| 3 | 47 | 97 | 64 |
| Ki (nM) | | | |
| 3185 | 551 | 21 | 602 |

In a cAMP assay using MC1-R, MC4-R and MC5-R, at 1 μM concentrations the compound of Example 4 exhibited no intrinsic activity at MC1-R and MC5-R, and was a partial agonist at MC4-R.

EXAMPLE 5

N-{3-[1-[2(R)-Amino-3-(2-chloro-4-methyl-phenyl)-propionyl]-5(R)-methyl-4-(2-naphthalen-2-yl-ethyl)-piperazin-2(S)-yl]-propyl}-guanidine The following compound was synthesized by the methods of both Schemes 3 and 5 using 2-naphthylacetic acid as J-COOH, (R)-(−)-2-amino-1-propanol as $NH_2$—$CH(R_5)$-$CH(R_4)$—OH, Fmoc-L-Arg(Boc)$_2$-OH as Prt-NH—CH($R_2$)—COOH, D-Alanine methyl ester as $NH_2$—$CH(R_5)$—$COOCH_3$ and Boc-D-2-chloro-4-methyl-Phe-OH as Q-COOH. It was tested as described above with the results shown. The mass was analyzed as 549.0 (M+H).

| MC1-R | MC3-R | MC4-R | MC5-R |
|---|---|---|---|
| Inhibition at 1 μM | | | |
| 14 | 68 | 99 | 63 |
| Ki (nM) | | | |
| 907 | 227 | 5 | 527 |

In a cAMP assay using MC4-R, at 1 μM concentrations the compound of Example 5 exhibited no intrinsic activity.

In ICV feeding studies at 1 nmol dose levels, a 24 hour change in food intake of −1.6 g, and change in weight of −3.9 g, was observed.

EXAMPLE 6

N-{3-[1-[2(R)-Amino-3-(4-chloro-2-methyl-phenyl)-propionyl]-5(R)-methyl-4-(2-naphthalen-2-yl-ethyl)-piperazin-2(S)-yl]-propyl}-guanidine The following compound was synthesized by the methods of both Schemes 3 and 5 using 2-naphthylacetic acid as J-COOH, (R)-(−)-2-amino-1-propanol as $NH_2$—$CH(R_5)$—$CH(R_4)$—OH, Fmoc-L-Arg(Boc)$_2$-OH as Prt-NH—CH$(R_2)$—COOH, D-alanine methyl ester as $NH_2$—$CH(R_5)$—COOCH$_3$ and Boc-D-4-chloro-2-methyl-Phe-OH as Q-COOH. It was tested as described above with the results shown. The mass was analyzed as 549.0 (M+H).

| MC1-R | MC3-R | MC4-R | MC5-R |
|---|---|---|---|
| Inhibition at 1 μM | | | |
| 6 | 74 | 100 | 77 |
| Ki (nM) | | | |
| 1052 | 99 | 1 | 219 |

In a cAMP assay for determination of agonist/antagonist status, it was determined that the compound was a partial agonist as to MC4-R.

In rat model IV and ICV penile erection induction experiments at doses ranging from 0.3 to 30 μg/Kg given IV and at 0.01 to 10 nmole given ICV, no penile erection response was observed.

In ICV feeding studies at 1 nmol dose levels, a 24 hour change in food intake of −5.5 g was observed.

Feeding studies were conducted as described above ICV at a 1 nmole dose level, IV at both 1 and 3 mg/Kg dose levels, and IP (intraperitoneal) at 3 mg/kg. Male Sprague-Dawley (8 to 12 per group) were fed powdered chow and water ad libitum, and dosed ICV, IV or IP with either vehicle or selected compounds with the following results:

| Difference in Food Intake vs. Vehicle, Grams of Food | | | |
|---|---|---|---|
| ICV 1 nmole | IV 1 mg/Kg | IV 3 mg/Kg | IP 3 mg/Kg |
| −5.3 | 0.4 | −3.5 | −0.7 |

Figure 4:
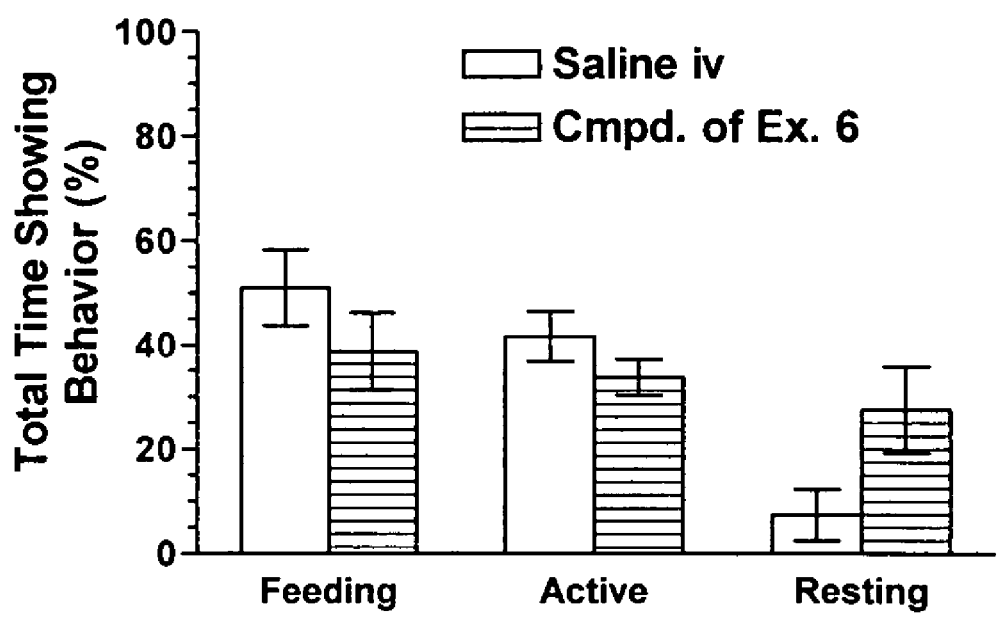
FIG. 4 is a chart showing behavior in an animal model following administration of the compound of Example 6 or a control.
Figure 5:
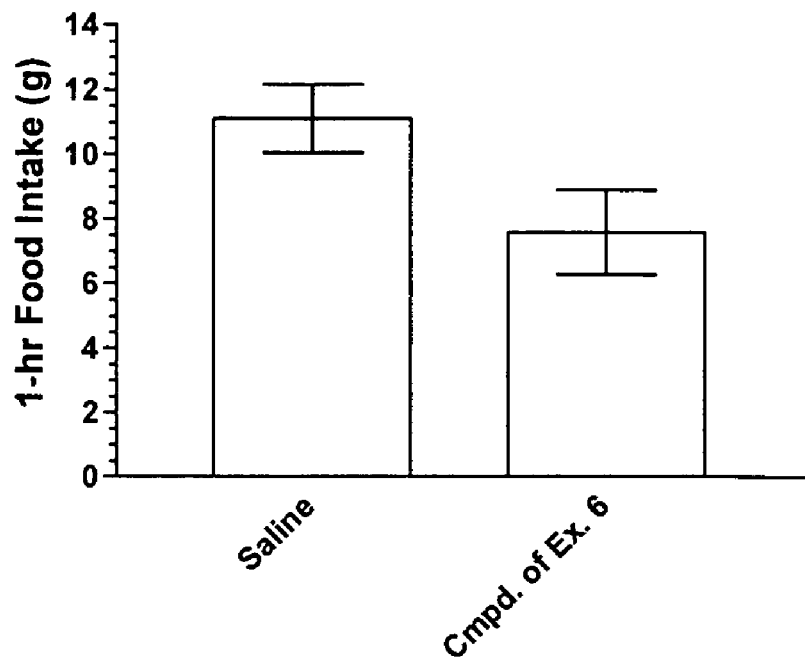
FIG. 5 is a chart of one hour food intake in an animal model following administration of the compound of Example 6 or a control.

In behavioral satiety studies, male Sprague-Dawley rats were maintained on a restricted food schedule. When food was presented, rats showed a sequence of feeding activity followed by increased time spent resting. The compound of Example 6 administered IV 2 hours prior to food presentation caused a decrease in food intake and feeding behavior and an earlier onset in resting behavior consistent with a satiety effect (Halford J C, Wanninayake S C and Blundell J E: Behavioral satiety sequence (BSS) for the diagnosis of drug action on food intake. *Pharmacol. Biochem. Behav.* 61(2): 159-168, 1998), as shown FIG. 4, showing behavior compared to saline, and FIG. 5, showing total one-hour food intake in grams. No abnormal behavior was seen.

Figure 7:
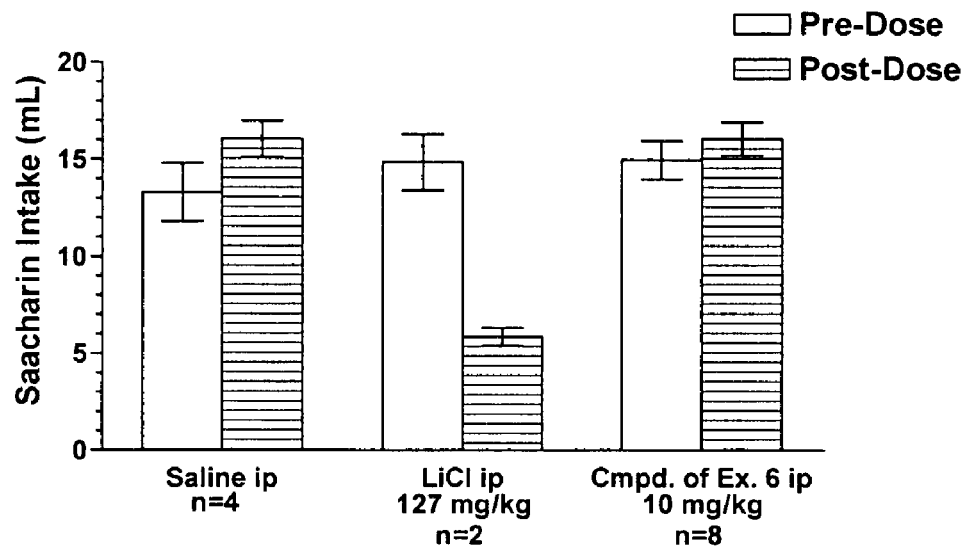
FIG. 7 is a chart of saccharin intake in a conditioned taste aversion response test of the compound of Example 6 compared to positive and negative controls.

In conditioned taste avoidance studies, rats were conditioned to associate a 0.1% saccharin solution with a dose of either lithium chloride or the compound of Example 6. Two days later, a 0.1% saccharin solution was presented again. A decrease in fluid intake suggests development of a conditioned taste aversion. As shown in FIG. 7, there was no conditioned taste avoidance associated with the compound of Example 6.

Figure 8:
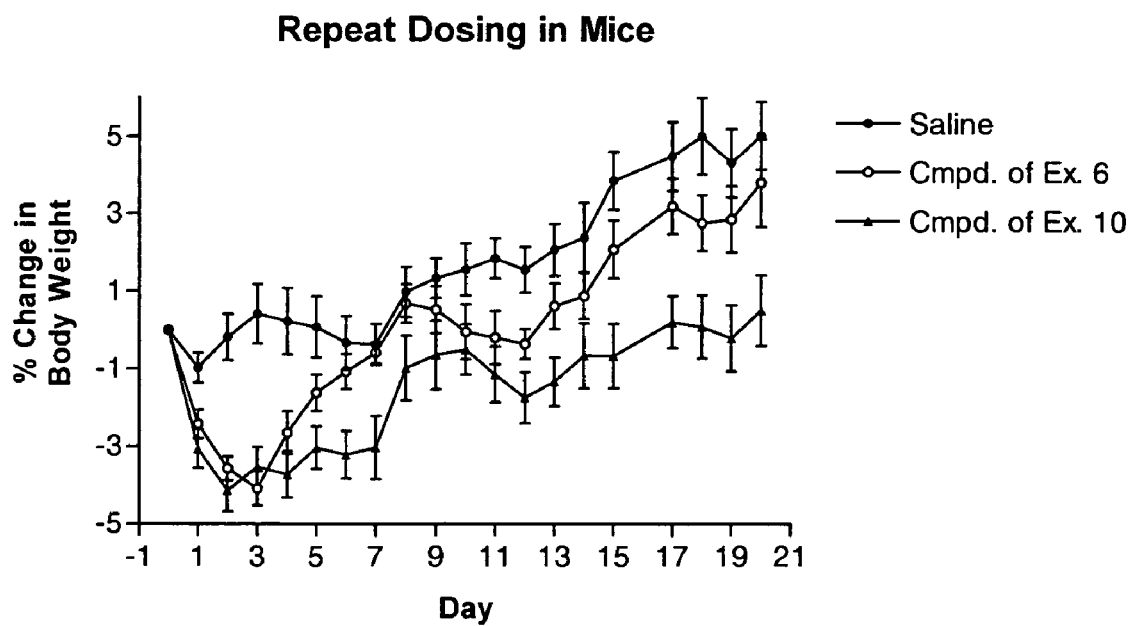
FIG. 8 is a graph of percent change in body weight in an animal model of animals in growth phase for a 21 day period where negative control and the compounds of Examples 6 and 10 were administered for 7 days.

Repeat dosing studies were conducted in C57BL6 mice (n=10 per group), housed in a reverse light cycle (on at 12 am off at 12 pm), and weighed daily at 11:00. The compound of Example 6 was diluted in sterile saline, 0.6 mg/mL and dosed IP at 5 mL/kg at 11:00 am. For BID dosing, drugs were administered at 11:00 am and 4:30 pm. Mice were dosed with the compound of Example 6 (3 mg/kg) twice a day for the first 3 days and once per day for the next 4 days. As shown in FIG. 8, which also includes data on the compound of Example 10, mice in growth phase administered the compound of Example 6 initiated net wet gain after cessation of treatment (after day 7), but consistently maintained average weights less than control animals receiving saline.

EXAMPLE 7

N-{3-[1-[2(R)-Amino-3-(2,4-dichloro-phenyl)-propionyl]-5(S)-isobutyl-4-(2-naphthalen-2-yl-ethyl)-piperazin-2(S)-yl]-propyl}-guanidine The following compound was synthesized by the method of Scheme 3 using 2-naphthylacetic acid as J-COOH, L-leucinol as $NH_2$—$CH(R_5)$—$CH(R_4)$—OH, Fmoc-L-Arg(Boc)$_2$-OH as Prt-NH—$CH(R_2)$—COOH, and Boc-D-2,4-dichloro-Phe-OH as Q-COOH. It was tested as described above with the results shown. The mass was analyzed as 611.1 (M+H).

| MC1-R | MC3-R | MC4-R | MC5-R |
|---|---|---|---|
| Inhibition at 1 μM | | | |
| 4 | 16 | 95 | 28 |
| Ki (nM) | | | |
| 5895 | 495 | 48 | 695 |

In a cAMP assay using MC1-R, MC4-R and MC5-R, at 1 μM concentrations the compound of Example 7 exhibited no intrinsic activity at MC4-R, and was a partial agonist at MC1-R and MC5-R.

EXAMPLE 8

N-{3-[1-[2(R)-Amino-3-(2,4-dichloro-phenyl)-propionyl]-5(R)-isobutyl-4-(2naphthalen-2-yl-ethyl)-piperazin-2(S)-yl]-propyl}-guanidine The following compound was synthesized by the methods of both Schemes 3 and 5 using 2-naphthylacetic acid as J-COOH, D-Leucinol as $NH_2$—$CH(R_5)$—$CH(R_4)$—OH, D-leucine methyl ester as $NH_2$—$CH(R_5)$—$COOCH_3$, Fmoc-L-Arg(Boc)$_2$-OH as Prt-NH—$CH(R_2)$—COOH, and Boc-D-2,4-dichloro-Phe-OH as Q-COOH. It was tested as described above with the results shown. The mass was analyzed as 611.1 (M+H).

| MC1-R | MC3-R | MC4-R | MC5-R |
|---|---|---|---|
| Inhibition at 1 μM | | | |
| 21 | 64 | 99 | 75 |

| MC1-R | MC3-R | MC4-R | MC5-R |
|---|---|---|---|
| Ki (nM) | | | |
| 1364 | 87 | 4 | 160 |

In a cAMP assay using MC1-R, MC4-R and MC5-R, at 1 μM concentrations the compound of Example 8 exhibited no intrinsic activity at MC1-R and MC4-R, and was a partial agonist at MC5-R.

EXAMPLE 9

N-{3-[1-[2(R)-Amino-3-(4-chloro-2-fluoro-phenyl)-propionyl]-5(R)-methyl-4-(2-naphthalen-2-yl-ethyl)-piperazin-2(S)-yl]-propyl}-guanidine The following compound was synthesized by the method of Scheme 3 using 2-naphthylacetic acid as J-COOH, D-alaninol as $NH_2$—$CH(R_5)$—$CH(R_4)$—OH, Fmoc-L-Arg (Boc)$_2$-OH as Prt-NH—$CH(R_2)$—COOH, and Boc-D-4-chloro-2-fluoro-Phe-OH as Q-COOH. It was tested as described above with the results shown. The mass was analyzed as 552.9 (M+H).

| MC1-R | MC3-R | MC4-R | MC5-R |
|---|---|---|---|
| Inhibition at 1 μM | | | |
| 57 | 82 | 99 | 59 |
| Ki (nM) | | | |
| 109 | 186 | 6 | 204 |

In a cAMP assay using MC1-R, MC4-R and MC5-R, at 1 μM concentrations the compound of Example 9 was a partial agonist at MC1-R and MC4-R and an agonist at MC5-R.

EXAMPLE 10

N-{3-[1-[2(R)-Amino-3-(2,4-dimethyl-phenyl)-propionyl]-5(R)-methyl-4-(2-naphthalen-2-yl-ethyl)-piperazin-2(S)-yl]-propyl}-guanidine The following compound was synthesized by the methods of both Schemes 3 and 5 using 2-naphthylacetic acid as J-COOH, D-alaninol as $NH_2$—$CH(R_5)$—$CH(R_4)$—OH, D-alanine methyl ester as $NH_2$—$CH(R_5)$—$COOCH_3$, Fmoc-L-Arg(Boc)$_2$-OH as Prt-NH—$CH(R_2)$—COOH, and Boc-D-2,4-dimethyl-Phe-OH as Q-COOH. It was tested as described above with the results shown. The mass was analyzed as 529.0 (M+H).

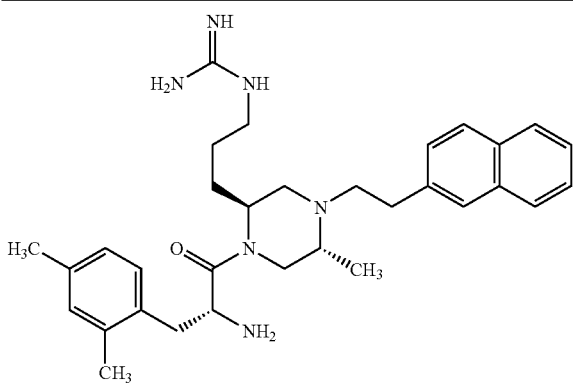

| MC1-R | MC3-R | MC4-R | MC5-R |
|---|---|---|---|
| Inhibition at 1 μM | | | |
| 9 | 62 | 100 | 59 |
| Ki (nM) | | | |
| 1223 | 157 | 11 | 717 |

In a cAMP assay for determination of agonist/antagonist status, it was determined that the compound was a partial agonist as to MC4-R.

In rat model IV and ICV penile erection induction experiments at doses ranging from 0.3 to 30 μg/Kg given IV and at 0.01 to 10 nmole given ICV, no penile erection response was observed.

Feeding studies were conducted as described above ICV at a 1 nmole dose level, IV at both 1 and 3 mg/Kg dose levels, and IP (intraperitoneal) at 3 mg/kg. Male Sprague-Dawley (8 to 12 per group) were fed powdered chow and water ad libitum, and dosed ICV, IV or IP with either vehicle or selected compounds with the following results:

| Difference in Food Intake vs. Vehicle, Grams of Food | | | |
|---|---|---|---|
| ICV 1 nmole | IV 1 mg/Kg | IV 3 mg/Kg | IP 3 mg/Kg |
| −4.9 | 0.9 | −6.0 | −3.7 |

In behavioral satiety studies as in Example 6, the compound of Example 10 administered IV 2 hours prior to food presentation caused a decrease in food intake and feeding behavior and an earlier onset in resting behavior consistent with a satiety effect, as shown FIG. 2, showing behavior compared to saline, and FIG. 3, showing total one-hour food intake in grams. No abnormal behavior was seen.

Figure 6:
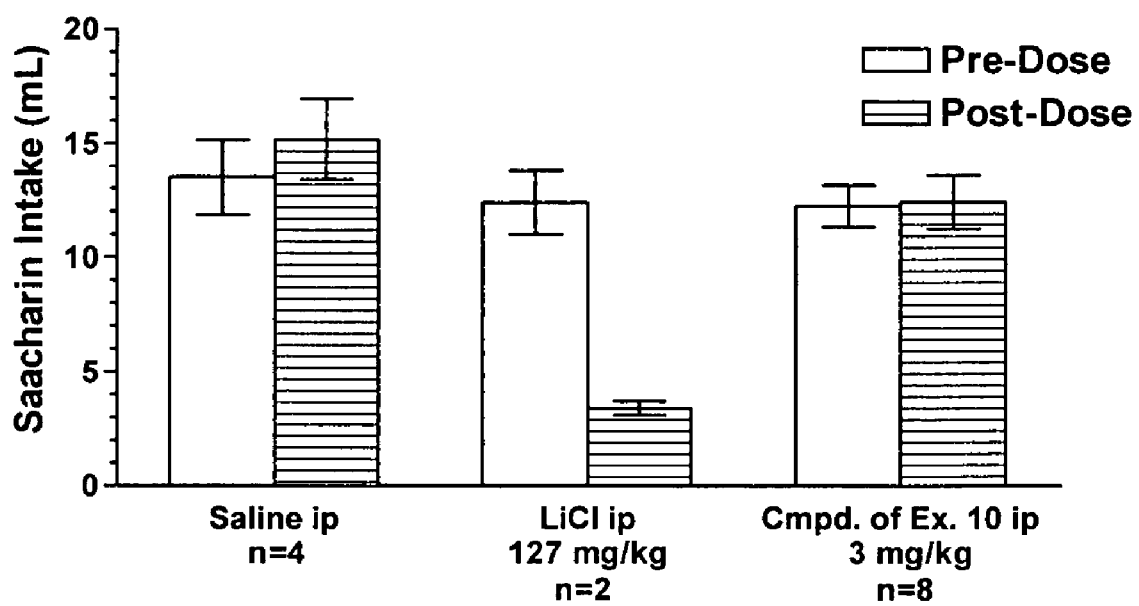
FIG. 6 is a chart of saccharin intake in a conditioned taste aversion response test of the compound of Example 10 compared to positive and negative controls.

In conditioned taste avoidance studies, rats or were conditioned to associate a 0.1% saccharin solution with a dose of either lithium chloride or the compound of Example 10. Two days later, a 0.1% saccharin solution was presented again. A decrease in fluid intake suggests development of a conditioned taste aversion. As shown in FIG. 6, there was no conditioned taste avoidance associated with the compound of Example 10.

Repeat dosing studies were conducted in C57BL/6 mice (n=10 per group), housed in a reverse light cycle (on at 12 am off at 12 pm), and weighed daily at 11:00. The compound of Example 6 was diluted in sterile saline, 0.6 mg/mL and dosed IP at 5 mL/kg at 11:00 am. Mice were dosed with the compound of Example 10 (3 mg/kg) once per day for 7 days. As shown in FIG. 8, which also includes data on the compound of Example 6, mice in growth phase administered the compound of Example 10 had a significant decrease in body weight during the initial 7 days, with a gradual increase in body weight, but consistently below control animals, for the two week period following cessation of administration of the compound of Example 10.

EXAMPLE 11

N{3-[1-[2(R)-Amino-3-(2-chloro-4-trifluoromethyl-phenyl)-propionyl]-5(R)-methyl-4-(2-naphthalen-2-yl-ethyl)-piperazin-2(S)-yl]-propyl}-guanidine The following compound was synthesized by the method of Scheme 3 using 2-naphthylacetic acid as J-COOH, D-alaninol as $NH_2$—$CH(R_5)$—$CH(R_4)$—OH, Fmoc-L-Arg(Boc)$_2$-OH as Prt-NH—$CH(R_2)$—COOH, and Boc-D-2-chloro-4-trifluoromethyl-Phe-OH as Q-COOH. It was tested as described above with the results shown. The mass was analyzed as 549.0 (M+H).

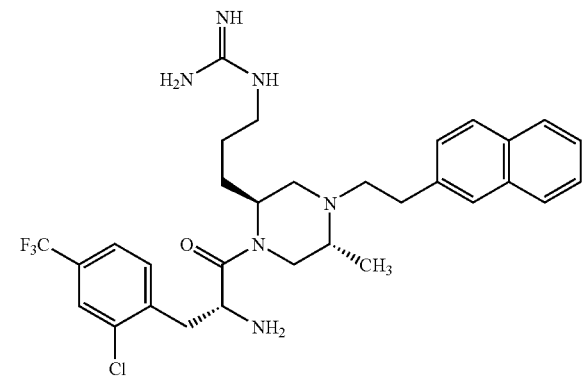

| MC1-R | MC3-R | MC4-R | MC5-R |
|---|---|---|---|
| Inhibition at 1 μM | | | |
| 0 | 48 | 98 | 52 |
| Ki (nM) | | | |
| 6356 | 468 | 13 | 574 |

In a cAMP assay using MC4-R, at 1 µM concentrations the compound of Example 11 exhibited no intrinsic activity.

EXAMPLE 12

N-{3-[1-[2(R)-Amino-3-(4-chloro-phenyl)-propionyl]-5(R)-methyl-4-(2-naphthalene-2-yl-ethyl)-piperazin-2(S)-yl]-propyl}-guanidine The following compound was synthesized by both the methods of both Schemes 3 and 5 using 2-naphthylacetic acid as J-COOH, D-alanine as $NH_2$—$CH(R_5)$—$CH(R_4)$—OH, D-alanine methyl ester as $NH_2$—$CH(R_5)$—$COOCH_3$, Fmoc-L-Arg(Boc)$_2$-OH as Prt-NH—$CH(R_2)$—COOH, and Boc-D-4-chloro-Phe-OH as Q-COOH. It was tested as described above with the results shown. The mass was analyzed as 534.9 (M+H).

| MC1-R | MC3-R | MC4-R | MC5-R |
|---|---|---|---|
| Inhibition at 1 µM | | | |
| 64 | 70 | 97 | 61 |
| Ki (nM) | | | |
| 94 | 160 | 11 | 551 |

In a cAMP assay for determination of agonist/antagonist status, it was determined that the compound was a partial agonist as to MCL-R, MC4-R and MC5-R.

In ICV feeding studies at 1 nmol dose levels, a 24 hour change in food intake of –3.9 g, and change in weight of –3.9 g, was observed. In IV feed studies at a dose level of 3 mg/Kg, a 24 hour change in food intake of –9.6, and change in weight of –6.6 g, was observed.

In rat model IV and ICV penile erection induction experiments at doses ranging from 0.3 to 30 µg/Kg given IV and at 0.01 to 10 nmole given ICV, no penile erection response was observed.

EXAMPLE 13

N-{3-[1-[2(R)-Amino-3-(3,4-dichloro-phenyl)-propionyl]-5(R)-methyl-4-(2-naphthalene-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2$—$CH(R_5)$—$COOCH_3$, and Boc-D-3,4-dichloro-Phe-OH as Q-COOH. It was tested as described above with the results shown. The mass was analyzed as 569.3 (M+H).

| MC1-R | MC3-R | MC4-R | MC5-R |
|---|---|---|---|
| Inhibition at 1 µM | | | |
| 12 | 37 | 96 | 32 |
| Ki (nM) | | | |
| 628 | 345 | 25 | 814 |

In a cAMP assay using MC1-R, MC4-R and MC5-R, at 1 µM concentrations the compound of Example 13 exhibited no intrinsic activity at MC1-R, and was a partial agonist at MC4-R and MC5-R.

EXAMPLE 14

N{3-[1-[2(R)-Amino-3-(2,4-dimethyl-phenyl)-propionyl]-5(R)-methyl-4-(2-naphthalen-2-yl-methyl)-piperazin-2(S)-yl]-propyl}-guanidine The following compound was synthesized by the method of Scheme 5 using 2-naphthoic acid as J-COOH, D-alanine methyl ester as $NH_2$—$CH(R_5)$—$COOCH_3$, and Boc-D-2,4-dimethyl-Phe-OH as Q-COOH. It was tested as described above with the results shown. The mass was analyzed as 515.4 (M+H).

| MC1-R | MC3-R | MC4-R | MC5-R |
|---|---|---|---|
| Inhibition at 1 µM | | | |
| 40 | 19 | 66 | 33 |

EXAMPLE 15

N{3-[1-[4-(4-Chloro-phenyl)-pyrrolidine-3-carbonyl]-5(R)-methyl-4-(2-naphthalen-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2—CH(R_4)—COOCH_3$, and 1-Boc-4-(4-chlorophenyl)pyrrolidine-3-carboxylic acid as Q-COOH. It was tested as described above with the results shown. The mass was analyzed as 561.4 (M+H).

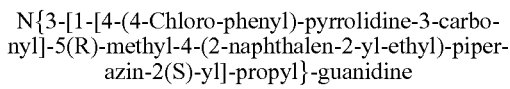

Inhibition at 1 μM

| MC1-R | MC3-R | MC4-R | MC5-R |
|---|---|---|---|
| 0 | 39 | 46 | 73 |

EXAMPLE 16

N-{1 (R)-(4-chloro-2-Dimethyl-benzyl)-2-[2(S)-(3-guanidino-propyl)-S(R)-methyl-4-(2-naphthalen-2-yl-acetyl)-piperazin-1-yl]-2-oxo-ethyl}-acetamide The following compound was synthesized by the method of Scheme 7, in which the compound of Example 45 was treated by the method of Example 36 to introduce an acetyl group at the amino group of the D-4-chloro-2-methyl-Phe residue. It was tested as described above with the results shown. The mass was analyzed as 605.3 (M+H).

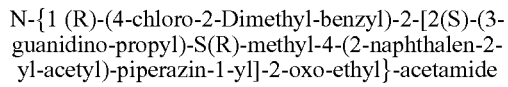

Ki (nM)

| MC1-R | MC3-R | MC4-R | MC5-R |
|---|---|---|---|
| 1388 | 136 | 5 | 234 |

In a cAMP assay using MC1-R, MC3-R and MC5-R, at 1 μM concentrations the compound of Example 16 exhibited no intrinsic activity at MC3-R, and was a partial agonist at MC1-R, MC4-R and MC5-R.

In rat model IV penile erection induction experiments at doses ranging from 0.3 to 30 μg/Kg no penile erection response was observed.

EXAMPLE 17

N-{3-[1-(2(R)-Amino-3-naphthalen-2-yl-propionyl)-5(R)-methyl-4-(2-naphthalen-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2—CH(R_5)—COOCH_3$, and Boc-D-2-Nal-OH as Q-COOH. It was tested as described above with the results shown. The mass was analyzed as 551.7 (M+H).

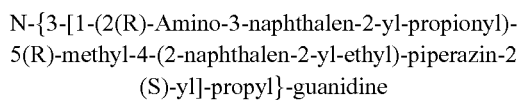

| MC1-R | MC3-R | MC4-R | MC5-R |
|---|---|---|---|
| Inhibition at 1 μM | | | |
| 35 | 83 | 98 | 76 |
| Ki (nM) | | | |
| 207 | 137 | 6 | 258 |

EXAMPLE 18

N-{3-[1-(2(R)-Amino-3-naphthalen-2-yl-propionyl)-5(R)-methyl-4-(3-phenyl-propyl)-piperazin-2(S)-yl]-propyl}-guanidine The following compound was synthesized by the method of Scheme 6 using hydrocinnamaldehyde as J-aldehyde, D-alanine methyl ester as $NH_2—CH(R_5)—COOCH_3$, and Boc-D-2-Nal-OH as Q-COOH. It was tested as described above with the results shown. The mass was analyzed as 515.4 (M+H).

| MC1-R | MC3-R | MC4-R | MC5-R |
|---|---|---|---|
| Inhibition at 1 µM | | | |
| 0 | 24 | 69 | 25 |
| Ki (nM) | | | |
| 670 | 2652 | 489 | 650 |

In rat model IV penile erection induction experiments at doses ranging from 0.3 to 30 µg/Kg no penile erection response was observed.

EXAMPLE 19

N-{3-[1-(2(R)-Amino-3-naphthalen-2-yl-propionyl)-5(R)-methyl-4-(2-p-tolyl-ethyl)-piperazin-2(S)-yl]-propyl}-guanidine The following compound was synthesized by the method of Scheme 6 using 4-methylphenylacetaldhyde as J-aldehyde, D-alanine methyl ester as $NH_2$—$CH(R_5)$—$COOCH_3$, and Boc-D-2-Nal-OH as Q-COOH. It was tested as described above with the results shown. The mass was analyzed as 515.4 (M+H).

| MC1-R | MC3-R | MC4-R | MC5-R |
|---|---|---|---|
| Inhibition at 1 µM | | | |
| 32 | 61 | 95 | 65 |
| Ki (nM) | | | |
| 137 | 164 | 29 | 448 |

In a cAMP assay using MC1-R, MC3-R, MC4-R and MC5-R, at 1 µM concentrations the compound of Example 19 exhibited no intrinsic activity at MC3-R, and was a partial agonist at MC1-R, MC4-R and MC5-R.

In rat model IV penile erection induction experiments at doses ranging from 0.3 to 30 µg/Kg no penile erection response was observed.

EXAMPLE 20

N-{3-[1-(2(R)-Amino-3-naphthalen-2-yl-propionyl)-4-(2-1H-indol-3-yl-acetyl)-5(R)-methyl-piperazin-2(S)-yl]-propyl}-guanidine The following compound was synthesized by the method of Scheme 6 using indole-3-acetic acid as J-COOH, D-alanine methyl ester as $NH_2$—$CH(R_5)$—$COOCH_3$, and Boc-D-2-Nal-OH as Q-COOH. It was tested as described above with the results shown. The mass was analyzed as 554.4 (M+H).

| MC1-R | MC3-R | MC4-R | MC5-R |
|---|---|---|---|
| Inhibition at 1 µM | | | |
| 20 | 35 | 90 | 6 |
| Ki (nM) | | | |
| 315 | 1822 | 35 | 1527 |

In a cAMP assay using MC1-R, MC3-R, MC4-R and MC5-R, at 1 µM concentrations the compound of Example 20 exhibited no intrinsic activity at MC1-R and MC3-R, and was a partial agonist at MC4-R and MC5-R.

In rat model IV penile erection induction experiments at doses ranging from 0.3 to 30 µg/Kg no penile erection response was observed.

EXAMPLE 21

N-{3-[1-(2(R)-Amino-3-naphthalen-2-yl-propionyl)-4-(2-1H-indol-3-yl-propionyl)-5(R)-methyl-piperazin-2(S)-yl]-propyl}-guanidine The following compound was synthesized by the method of Scheme 6 using indole-3-propionic acid as J-COOH, D-alanine methyl ester as $NH_2$—$CH(R_5)$—$COOCH_3$, and Boc-D-2-Nal-OH as Q-COOH. It was tested as described above with the results shown. The mass was analyzed as 568.5 (M+H).

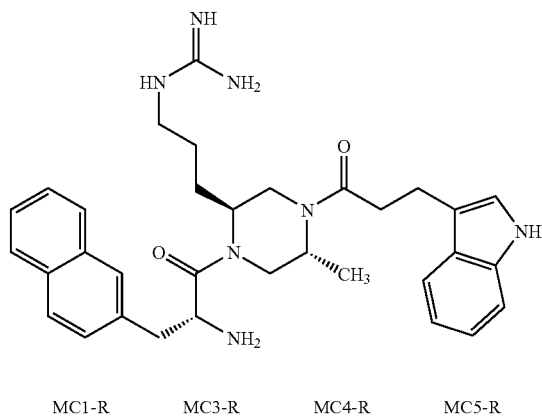

| MC1-R | MC3-R | MC4-R | MC5-R |
|---|---|---|---|
| Inhibition at 1 µM | | | |
| 14 | 34 | 74 | 6 |
| Ki (nM) | | | |
| 123 | 1726 | 323 | 678 |

EXAMPLE 22

N-{3-[1-(2(R)-Amino-3-naphthalen-2-yl-propionyl)-4-(2-1H-indol-3-yl-butyryl)-5(R)-methyl-piperazin-2(S)-yl]-propyl}-guanidine The following compound was synthesized by the method of Scheme 6 using indole-3-butyric acid as J-COOH, D-alanine methyl ester as $NH_2$—$CH(R_5)$—$COOCH_3$, and Boc-D-2-Nal-OH as Q-COOH. It was tested as described above with the results shown. The mass was analyzed as 582.6 (M+H).

| MC1-R | MC3-R | MC4-R | MC5-R |
|---|---|---|---|
| Inhibition at 1 µM | | | |
| 0 | 32 | 88 | 62 |
| Ki (nM) | | | |
| 1203 | 657 | 90 | 277 |

In rat model IV penile erection induction experiments at doses ranging from 0.3 to 30 µg/Kg given IV, the compound of Example 22 induced 0.5 to 0.8 mean penile erections per rat; on ICV administration of doses from 0.01 to 10 nmole, no penile erection response was observed.

EXAMPLE 23

N-(3-{1-(2(R)-Amino-3-naphthalen-2-yl-propionyl)-4-[2-(1H-indol-3-yl)-ethyl]-5(R)-methyl-piperazin-2(S)-yl}-propyl)-guanidine The following compound was synthesized by the method of Scheme 6 using indole-3-acetaldehyde as J-aldehyde, D-alanine methyl ester as $NH_2$—$CH(R_5)$—$COOCH_3$, and Boc-D-2-Nal-OH as Q-COOH. It was tested as described above with the results shown. The mass was analyzed as 540.5 (M+H).

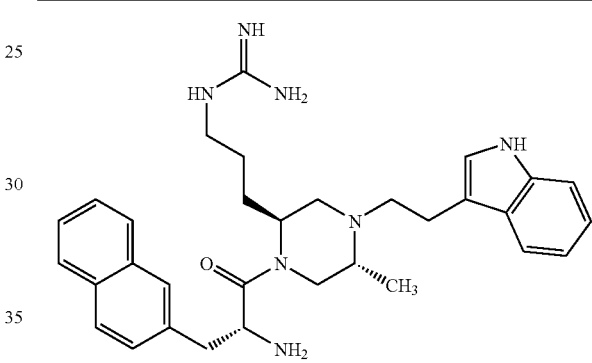

| MC1-R | MC3-R | MC4-R | MC5-R |
|---|---|---|---|
| Inhibition at 1 µM | | | |
| 2 | 27 | 93 | 51 |
| Ki (nM) | | | |
| 257 | 2122 | 37 | 808 |

In a cAMP assay using MC1-R, MC3-R, MC4-R and MC5-R, at 1 µM concentrations the compound of Example 23 exhibited no intrinsic activity at MC1-R, MC3-R and MC5-R, and was a partial agonist at MC4-R.

EXAMPLE 24

N-(3-{1-(2(R)-Amino-3-naphthalen-2-yl-propionyl)-5(R)-methyl-4-[2-(2-methyl-1H-indol-3-yl)-ethyl]-piperazin-2(S)-yl}-propyl)-guanidine The following compound was synthesized by the method of Scheme 6 using 2-methyl-indole-3-acetaldehyde as J-aldehyde, D-alanine methyl ester as $NH_2$—$CH(R_5)$—$COOCH_3$, and Boc-D-2-Nal-OH as Q-COOH. It was tested as described above with the results shown. The mass was analyzed as 544.5 (M+H).

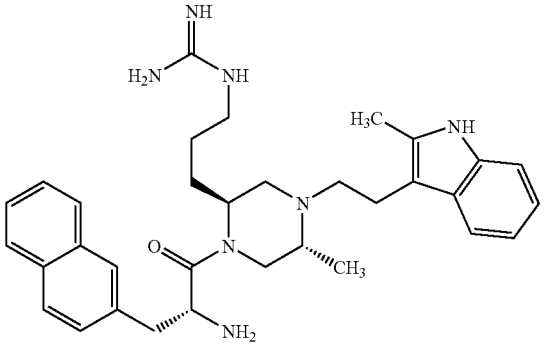

| MC1-R | MC3-R | MC4-R | MC5-R |
|---|---|---|---|
| Inhibition at 1 μM | | | |
| 73 | 57 | 95 | 76 |
| Ki (nM) | | | |
| 148 | 451 | 26 | 293 |

In a cAMP assay using MC1-R, MC3-R, MC4-R and MC5-R, at 1 μM concentrations the compound of Example 24 exhibited no intrinsic activity at MC3-R, was a partial agonist at MC1-R, and was an agonist at MC4-R and MC5-R.

In rat model IV penile erection induction experiments at doses ranging from 0.3 to 30 μg/Kg given IV, the compound of Example 24 induced 0.5 mean penile erections per rat; on ICV administration of doses from 0.01 to 10 nmole, no penile erection response was observed.

EXAMPLE 25

N-(3-{1-(2(R)-Amino-3-naphthalen-2-yl-propionyl)-5(R)-methyl-4-[2-(1-methyl-1H-indol-3-yl)-ethyl]-piperazin-2(S)-yl}-propyl)-guanidine The following compound was synthesized by the method of Scheme 6 using 1-methyl-indole-3-acetaldehyde as J-aldehyde, D-alanine methyl ester as $NH_2$—$CH(R_5)$—$COOCH_3$, and Boc-D-2-Nal-OH as Q-COOH. It was tested as described above with the results shown. The mass was analyzed as 554.7 (M+H).

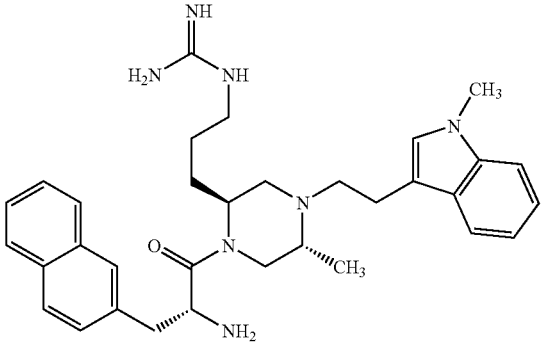

| MC1-R | MC3-R | MC4-R | MC5-R |
|---|---|---|---|
| Inhibition at 1 μM | | | |
| 19 | 20 | 74 | 41 |

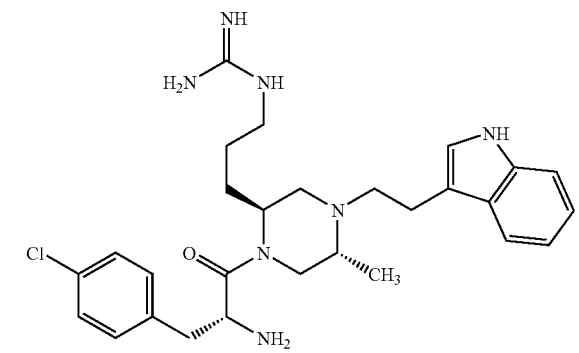

| MC1-R | MC3-R | MC4-R | MC5-R |
|---|---|---|---|
| Ki (nM) | | | |
| 2024 | 769 | 93 | 1205 |

EXAMPLE 26

N-(3-{1-(2(R)-Amino-(4-chloro-phenyl)-propionyl)-5(R)-methyl-4-[2-(1H-indol-3-yl)-ethyl]-piperazin-2(S)-yl}-propyl)-guanidine The following compound was synthesized by the method of Scheme 5 using indole-3-acetic acid as J-COOH, D-alanine methyl ester as $NH_2$—$CH(R_5)$—$COOCH_3$, and Boc-D-4-chloro-Phe-OH as Q-COOH. It was tested as described above with the results shown. The mass was analyzed as 524.5 (M+H).

| MC1-R | MC3-R | MC4-R | MC5-R |
|---|---|---|---|
| Inhibition at 1 μM | | | |
| 80 | 60 | 96 | 65 |
| Ki (nM) | | | |
| 138 | 301 | 8 | 360 |

In a CAMP assay using MC1-R, MC3-R, MC4-R and MC5-R, at 1 μM concentrations the compound of Example 26 exhibited no intrinsic activity at MC3-R, was a partial agonist at MC1-R and MC5-R, and an agonist at MC4-R.

In rat ICV feeding studies at 1 nmol dose levels, a 24 hour change in food intake of −6.0 g, and change in weight of −8.8 g, was observed.

In rat model IV penile erection induction experiments at doses ranging from 0.3 to 30 μg/Kg, no penile erection response was observed.

EXAMPLE 27

N-(3-{1-(2(R)-Amino-(4-chloro-2-methyl-phenyl)-propionyl)-5(R)-methyl-4-[2-(1H-indol-3-yl)-ethyl]-piperazin-2(S)-yl}-propyl)-guanidine The following compound was synthesized by the method of Scheme 5 using indole-3-acetic acid as J-COOH, D-alanine methyl ester as $NH_2$—$CH(R_5)$—$COOCH_3$, and Boc-D-4-chloro-2-methyl-Phe-OH as Q-COOH. It was tested as described above with the results shown. The mass was analyzed as 538.6 (M+H).

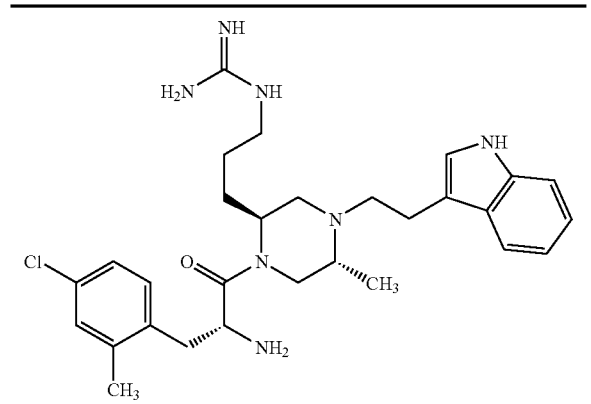

| MC1-R | MC3-R | MC4-R | MC5-R |
|---|---|---|---|
| Inhibition at 1 μM | | | |
| 40 | 74 | 98 | 75 |
| Ki (nM) | | | |
| 1730 | 177 | 5 | 360 |

In a cAMP assay using MC1-R, MC3-R, MC4-R and MC5-R, at 1 μM concentrations the compound of Example 27 exhibited no intrinsic activity at MC1-R and MC3-R, and was a partial agonist at MC4-R and MC5-R.

In ICV feeding studies at 1 nmol dose levels, a 24 hour change in food intake of −3.9 g, and change in weight of −4.8 g, was observed.

In rat model IV and ICV penile erection induction experiments at doses ranging from 0.3 to 30 μg/Kg given IV and at 0.01 to 10 nmole given ICV, no penile erection response was observed.

EXAMPLE 28

N-{3-[1-[2(R)-Amino-3-(phenyl)-propionyl]-5(R)-methyl-4-(2-naphthalen-2-yl-ethyl)-piperazin-2(S)-yl]-propyl}-guanidine The following compound was synthesized by the methods of Scheme 5 using 2-naphthylacetic acid as J-COOH, D-alanine methyl ester as $NH_2$—$CH(R_5)$—$COOCH_3$, and Boc-D-Phe-OH as Q-COOH. It was tested as described above with the results shown. The mass was analyzed as 500.9 (M+H).

| MC1-R | MC3-R | MC4-R | MC5-R |
|---|---|---|---|
| Inhibition at 1 μM | | | |
| 78 | 30 | 86 | 24 |
| Ki (nM) | | | |
| 26 | 915 | 119 | 2141 |

In a cAMP assay for determination of agonist/antagonist status, it was determined that the compound was a partial agonist as to MC4-R and MC5-R.

EXAMPLE 29

N-{3-[1-[2(R)-Amino-3-(4-methyl-phenyl)-propionyl]-5(R)-methyl-4-(2-naphthalen-2-yl-ethyl)-piperazin-2(S)-yl]-propyl}-guanidine The following compound was synthesized by the method of Schemes 5 using 2-naphthylacetic acid as J-COOH, D-alanine methyl ester as $NH_2$—$CH(R_5)$—$COOCH_3$, and Boc-D-4-methyl-Phe-OH as Q-COOH. It was tested as described above with the results shown. The mass was analyzed as 515.5 (M+H).

| MC1-R | MC3-R | MC4-R | MC5-R |
|---|---|---|---|
| Inhibition at 1 μM | | | |
| 50 | 15 | 85 | 33 |
| Ki (nM) | | | |
| 59 | 503 | 108 | 884 |

EXAMPLE 30

N-{3-[1-[2(R)-Amino-3-(4-methoxy-phenyl)-propionyl]-5(R)-methyl-4-(2-naphthalen-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2$—$CH(R_5)$—$COOCH_3$, and Boc-D-4-methoxyl-Phe-OH as Q-COOH. It was tested as described above with the results shown. The mass was analyzed as 534.1 (M+H).

| MC1-R | MC3-R | MC4-R | MC5-R |
|---|---|---|---|
| Inhibition at 1 µM | | | |
| 29 | 0 | 61 | 0 |

EXAMPLE 31

N-{3-[1-[3(4-Chloro-phenyl)-2(R)-dimethylamino-propionyl]-5(R)-methyl-4-(2-naphthalen-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2$—$CH(R_5)$—$COOCH_3$, and Fmoc-D-4-chloro-Phe-OH as Q-COOH. Methyl groups on the amino group of D-4-chloro-Phe-OH were attached by a reductive amination reaction with formaldehyde under the conditions described for synthesis of 5-3. It was tested as described above with the results shown. The mass was analyzed as 563.2 (M+H).

| MC1-R | MC3-R | MC4-R | MC5-R |
|---|---|---|---|
| Inhibition at 1 µM | | | |
| 55 | 67 | 97 | 38 |
| Ki (nM) | | | |
| 161 | 174 | 7 | 1019 |

In a cAMP assay using MC1-R, MC3-R, MC4-R and MC5-R, at 1 µM concentrations the compound of Example 31 exhibited no intrinsic activity at MC3-R, was a partial agonist at MC1-R and MC4-R, and an agonist at MC5-R.

EXAMPLE 32

N-{3-[1-[3-(4-Chloro-phenyl)-2(R)-methylamino-propionyl]-5(R)-methyl-4-(2-naphthalen-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2$—$CH(R_5)$—$COOCH_3$, and Fmoc-D-4-chloro-Phe-OH as Q-COOH. The methyl group on the amino group of D-4-chloro-Phe-OH was attached by a reductive amination reaction with formaldehyde under the conditions described in the synthesis of 3-4. It was tested as described above with the results shown. The mass was analyzed as 549.3 (M+H).

| MC1-R | MC3-R | MC4-R | MC5-R |
|---|---|---|---|
| Inhibition at 1 µM | | | |
| 63 | 59 | 96 | 22 |
| Ki (nM) | | | |
| 78 | 212 | 8 | 863 |

In a cAMP assay for determination of agonist/antagonist status, it was determined that the compound was a partial agonist as to MC3-R and MC4-R, and an agonist as to MC1-R and MC5-R.

EXAMPLE 33

N-{3-[1-[3-(4-Chloro-phenyl)-2(R)-diethylamino-propionyl]-5(R)-methyl-4-(2-naphthalen-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2$—$CH(R_5)$—$COOCH_3$, and Fmoc-D-4-chloro-Phe-OH as Q-COOH. The ethyl groups on the amino group of D-4-chloro-Phe-OH were attached by a reductive amination reaction with acetaldehyde under the condition described in the synthesis of 3-4. It was tested as described above with the results shown. The mass was analyzed as 591.3 (M+H).

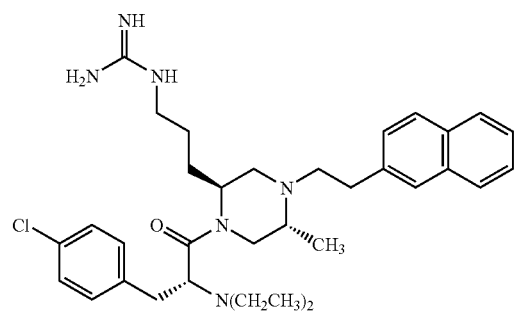

| MC1-R | MC3-R | MC4-R | MC5-R |
|---|---|---|---|
| Inhibition at 1 µM | | | |
| 46 | 29 | 93 | 42 |
| Ki (nM) | | | |
| 350 | 395 | 20 | 460 |

In a cAMP assay for determination of agonist/antagonist status, it was determined that the compound was a partial agonist as to MC1-R, MC3-R and MC4-R, and an agonist as to MC5-R.

EXAMPLE 34

N-{3-[1-[3-(4-Chloro-phenyl)-2(R)-isopropylamino-propionyl]-5(R)-methyl-4-(2-naphthalene-2-yl-ethyl)-piperazin-2(S)-yl]-propyl}-guanidine The following compound was synthesized by the method of Scheme 5 using 2-naphthylacetic acid as J-COOH, D-alanine methyl ester as $NH_2$—$CH(R_5)$—$COOCH_3$, and Fmoc-D-4-chloro-Phe-OH as Q-COOH. The iso-propyl group on the amine group of D-4-chloro-Phe-OH was attached by reductive amination reaction with acetone under the condition described in synthesis of 3-4. It was tested as described above with the results shown. The mass was analyzed as 577.0 (M+H).

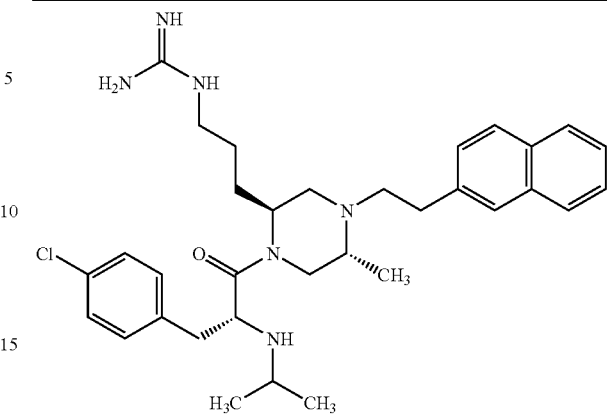

| MC1-R | MC3-R | MC4-R | MC5-R |
|---|---|---|---|
| Inhibition at 1 µM | | | |
| 83 | 71 | 98 | 61 |
| Ki (nM) | | | |
| 12 | 92 | 225 | 47 |

In a cAMP assay for determination of agonist/antagonist status, it was determined that the compound was a partial agonist as to MC3-R, and an agonist as to MC1-R, MC4-R and MC5-R.

EXAMPLE 35

N-{3-[1-[2(R)-Amino-3-naphthalen-2-yl-propionyl]-5(R)-isobutyl-4-(2-naphthalen-2-yl-ethyl)-piperazin-2(S)-yl]-propyl}-guanidine The following compound was synthesized by the method of Scheme 5 using 2-naphthylacetic acid as J-COOH, D-leucinol as $NH_2$—$CH(R_5)$—$CH(R_4)$—OH, D-leucine methyl ester as $NH_2$—$CH(R_5)$—$COOCH_3$, and Boc-D-2-Nal-OH as Q-COOH. It was tested as described above with the results shown. The mass was analyzed as 593.8 (M+H).

| MC1-R | MC3-R | MC4-R | MC5-R |
|---|---|---|---|
| Inhibition at 1 µM | | | |
| 6 | 31 | 89 | 48 |
| Ki (nM) | | | |
| 1005 | 331 | 3 | 306 |

In a cAMP assay using MC1-R, MC3-R, MC4-R and MC5-R, at 1 μM concentrations the compound of Example 35 exhibited no intrinsic activity at MC1-R, MC3-R and MC4-R, and was a partial agonist at MC5-R.

EXAMPLE 36

N-{2-[2(S)-(3-Guanidino-propyl)-5(R)-isobutyl-4-(2-naphthalen-2-yl-ethyl)-piperazin-1-yl]-1 (R)-naphthalen-2-ylmethyl-2-oxo-ethyl}-acetamide The following compound was synthesized by the method of Scheme 5 using 2-naphthylacetic acid as J-COOH, D-leucinol as NH$_2$—CH(R$_5$)—CH(R$_4$)—OH, D-leucine methyl ester as NH$_2$—CH(R$_5$)—COOCH$_3$, and Boc-D-2-Nal-OH as Q-COOH as described in Example 35. An acetyl group was attached to the amino group of D-2-Nal by reaction of the compound of Example 35 with Ac-OSu in DMF. It was tested as described above with the results shown. The mass was analyzed as 635.9 (M+H).

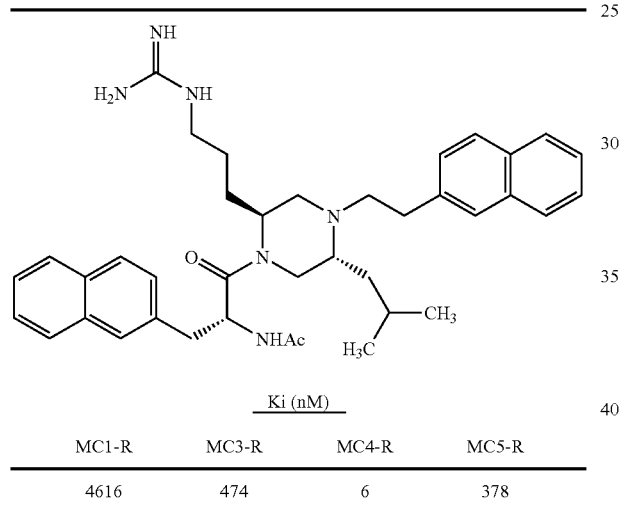

| Ki (nM) | | | |
|---|---|---|---|
| MC1-R | MC3-R | MC4-R | MC5-R |
| 4616 | 474 | 6 | 378 |

In a cAMP assay using MC1-R, MC3-R, MC4-R and MC5-R, at 1 μM concentrations the compound of Example 36 exhibited no intrinsic activity at MC1-R, MC3-R and MC4-R, and was a partial agonist at MC5-R.

EXAMPLE 37

N-{1(R)-(2,4-Dimethyl-benzyl)-2-[2(S)-(3-guanidino-propyl)-5(R)-methyl-4-(2-naphthalen-2-yl-ethyl)-piperazin-1-yl]-2-oxo-ethyl}-acetamide The following compound was synthesized by the method of Scheme 5 using 2-naphthylacetic acid as J-COOH, D-alaninol as NH$_2$—CH(R$_5$)—CH(R$_4$)—OH, D-alanine methyl ester as NH$_2$—CH(R$_5$—COOCH$_3$, and Boc-D-2,4-dimethyl-Phe-OH as Q-COOH. An acetyl group was attached to the amino group of D-2,4-dimethyl-Phe residue by the method described in Example 36. It was and tested as described above with the results shown. The mass was analyzed as 571.9 (M+H).

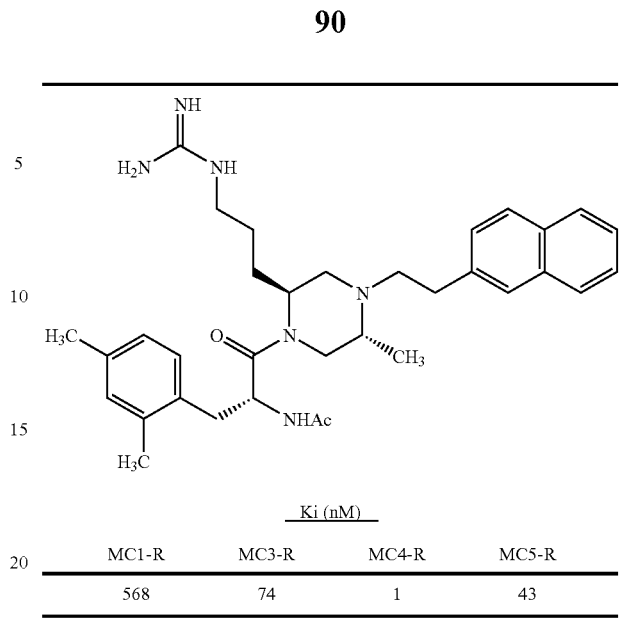

| Ki (nM) | | | |
|---|---|---|---|
| MC1-R | MC3-R | MC4-R | MC5-R |
| 568 | 74 | 1 | 43 |

In a cAMP assay using MC4-R, at 1 μM concentrations the compound of Example 37 exhibited no intrinsic activity.

EXAMPLE 38

N-{3-[1-(2(R)-Amino-3-naphthalen-2-yl-propionyl)-5(R)-methyl-4-(2-naphthalen-2-yl-acetyl)-piperazin-2(S)-yl]-propyl}-guanidine The following compound was synthesized by the method of Scheme 6 using 2-naphthylacetic acid as J-COOH, D-alanine methyl ester as NH$_2$—CH(R$_5$)—COOCH$_3$, and Boc-D-2-Nal-OH as Q-COOH. It was tested as described above with the results shown. The mass was analyzed as 565.4 (M+H).

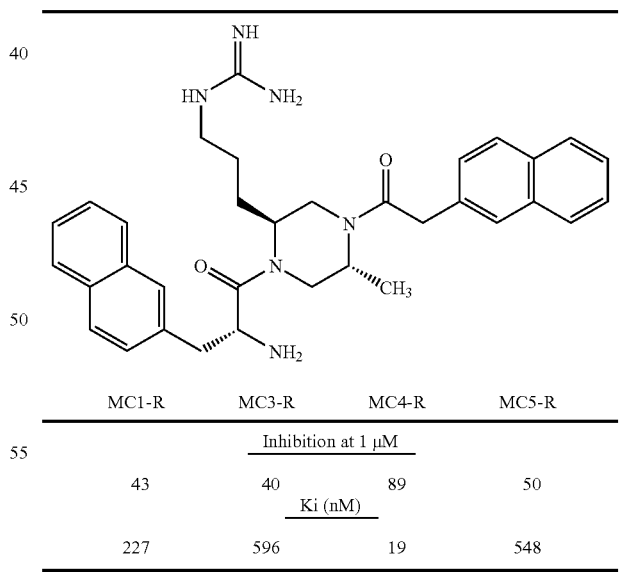

| MC1-R | MC3-R | MC4-R | MC5-R |
|---|---|---|---|
| Inhibition at 1 μM | | | |
| 43 | 40 | 89 | 50 |
| Ki (nM) | | | |
| 227 | 596 | 19 | 548 |

In a cAMP assay for determination of agonist/antagonist status, it was determined that the compound was a partial agonist as to MC3-R, and an agonist as to MC1-R, MC4-R and MC5-R.

In rat model IV penile erection induction experiments at doses ranging from 0.3 to 30 μg/Kg, no penile erection response was observed.

EXAMPLE 39

N-{3-[1-(2(R)-Amino-3-naphthalen-2-yl-propionyl)-4-(3H-imidazol-4-ylmethyl)-5(R)-methyl-piperazin-2(S)-yl]-propyl}-guanidine The following compound was synthesized by the method of Scheme 6 using 4(5)-imidazole carboxyaldehyde as J-aldehyde, D-alanine methyl ester as NH$_2$—CH(R$_5$)—COOCH$_3$, and Boc-D-2-Nal-OH as Q-COOH. It was tested as described above with the results shown. The mass was analyzed as 477.2 (M+H).

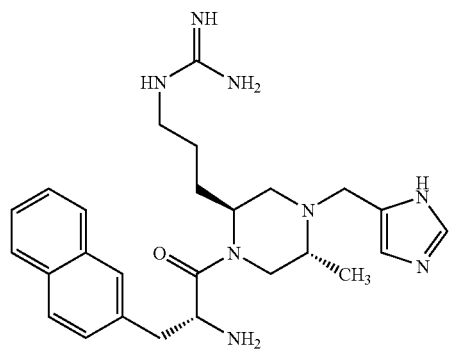

| | Ki (nM) | | |
|---|---|---|---|
| MC1-R | MC3-R | MC4-R | MC5-R |
| >1000 | >1000 | >1000 | >1000 |

In rat model IV penile erection induction experiments at doses ranging from 0.3 to 30 µg/Kg, no penile erection response was observed.

EXAMPLE 40

N-{3-[1-(2(R)-Amino-3-naphthalen-2-yl-propionyl)-4-(4-imidazol-1-yl-benzyl)-5(R)-methyl-piperazin-2(S)-yl]-propyl}-guanidine The following compound was synthesized by the method of Scheme 6 using 4-(1H-imidazole-1-yl)benzaldehyde as J-aldehyde, D-alanine methyl ester as NH$_2$—CH(R$_5$)—COOCH$_3$, and Boc-D-2-Nal-OH as Q-COOH. It was tested as described above with the results shown. The mass was analyzed as 553.2 (M+H).

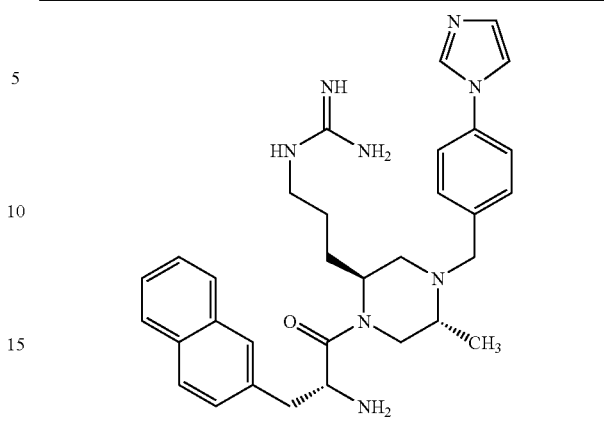

| | Ki (nM) | | |
|---|---|---|---|
| MC1-R | MC3-R | MC4-R | MC5-R |
| >1000 | >1000 | >1000 | >1000 |

EXAMPLE 41

N-{2-[2(S)-(3-Guanidino-propyl)-5(R)-methyl-4-(2-naphthalen-2-yl-acetyl)-piperazin-1-yl]-1 (R)-naphthalen-2-ylmethyl-2-oxo-ethyl}-acetamide The following compound was synthesized by the method of Scheme 6. The compound of Example 38 was treated by the method of Example 36 to introduce an acetyl group at the amino group of the D-2-Nal residue. It was tested as described above with the results shown. The mass was analyzed as 607.7 (M+H).

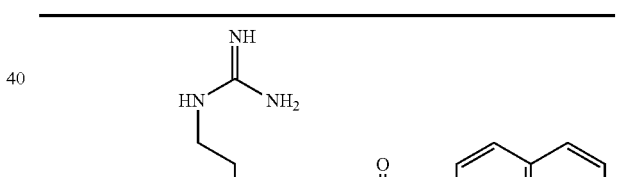

| MC1-R | MC3-R | MC4-R | MC5-R |
|---|---|---|---|
| Inhibition at 1 µM | | | |
| 51 | 38 | 97 | 44 |
| Ki (nM) | | | |
| 625 | 754 | 8 | 891 |

In a cAMP assay for determination of agonist/antagonist status, it was determined that the compound was a partial agonist as to MC4-R.

In rat model IV and ICV penile erection induction experiments at doses ranging from 0.3 to 30 µg/Kg given IV and at 0.01 to 10 nmole given ICV, 1 mean penile erection per rat was observed on IV administration, and no penile erection response was observed on ICV administration.

EXAMPLE 42

N-{2-[4-(2(R)-Amino-3-naphthalen-2-yl-propionyl)-5(S)-(3-guanidino-propyl)-2(R)-methyl-piperazin-1-yl]-1(R)-naphthalen-2-ylmethyl-2-oxo-ethyl}-methanesulfonamide The following compound was synthesized by the method of Scheme 6 using Fmoc-D-2-Nal-OH as J-COOH, D-alanine methyl ester as $NH_2$—$CH(R_5)$—$COOCH_3$, and Boc-D-2-Nal-OH as Q-COOH. The J-COOH moiety was further modified by removal of the Fmoc group and reacting with methanesulfonyl chloride to form a sulfonamide moiety. It was tested as described above with the results shown. The mass was analyzed as 672.4 (M+H).

| MC1-R | MC3-R | MC4-R | MC5-R |
|---|---|---|---|
| Inhibition at 1 µM | | | |
| 55 | 77 | 100 | 66 |
| Ki (nM) | | | |
| 97 | 205 | 7 | 151 |

In a cAMP assay using MC1-R, MC3-R, MC4-R and MC5-R, at 1 µM concentrations the compound of Example 42 exhibited no intrinsic activity at MC3-R, was a partial agonist at MC1-R, and an agonist at MC4-R and MC5-R.

In rat model IV penile erection induction experiments at doses ranging from 0.3 to 30 µg/Kg, no penile erection response was observed.

EXAMPLE 43

N-{2-[4-(2(R)-Amino-3-naphthalen-2-yl-propionyl)-5(S)-(3-guanidino-propyl)-2(R)-methyl-piperazin-1-yl]-1(R)-naphthalen-2-ylmethyl-2-oxo-ethyl}-acetamide The following compound was synthesized by the method of Scheme 6 using Fmoc-D-2-Nal-OH as J-COOH, D-alanine methyl ester as $NH_2$—$CH(R_5)$—$COOCH_3$, and Boc-D-2-Nal-OH as Q-COOH. The J-COOH moiety was further modified by removal of the Fmoc group and reacting with acetic anhydride to form a acetamide moiety. It was tested as described above with the results shown. The mass was analyzed as 636.3 (M+H).

| MC1-R | MC3-R | MC4-R | MC5-R |
|---|---|---|---|
| Inhibition at 1 µM | | | |
| 27 | 69 | 95 | 61 |
| Ki (nM) | | | |
| 430 | 157 | 11 | 291 |

In a cAMP assay using MC1-R, MC3-R, MC4-R and MC5-R, at 1 µM concentrations the compound of Example 43 exhibited no intrinsic activity at MC3-R, was a partial agonist at MC1-R and was an agonist at MC4-R and MC5-R.

In rat model IV penile erection induction experiments at doses ranging from 0.3 to 30 µg/Kg, no penile erection response was observed.

EXAMPLE 44

N-{3-[1-[2(R)-Amino-3-(2,4-dimethyl-phenyl)-propionyl]-5(R)-methyl-4-(2-naphthalen-2-yl-acetyl)-piperazin-2(S)-yl]-propyl}-guanidine The following compound was synthesized by the method of Scheme 7 using 2-naphthyl acetic acid as J-COOH, L-Orn (Boc) methyl ester as $NH_2$—$CH(R_2)$—$COOCH_3$, and Boc-D-2,4-di-methyl-Phe-OH as Q-COOH. It was tested as described above with the results shown. The mass was analyzed as 543.4 (M+H).

| MC1-R | MC3-R | MC4-R | MC5-R |
|---|---|---|---|
| Inhibition at 1 µM | | | |
| 0 | 25 | 86 | 7 |
| Ki (nM) | | | |
| 431 | 526 | 6 | 1536 |

In a cAMP assay for determination of agonist/antagonist status, it was determined that the compound was a partial agonist as to MC1-R, MC3-R and MC5-R, and an agonist as to MC4-R.

In rat model IV penile erection induction experiments at doses ranging from 0.3 to 30 μg/Kg, 0.5 to 0.7 mean penile erections per rat were observed.

EXAMPLE 45

N-{3-[1-[2(R)-Amino-3-(4-chloro-2-dimethyl-phenyl)-propionyl]-5(R)-methyl-4-(2-naphthalen-2-yl-acetyl)-piperazin-2(S)-yl]-propyl}-guanidine The following compound was synthesized by the method of Scheme 7 using 2-naphthyl acetic acid as J-COOH, L-Orn (Boc) methyl ester as $NH_2$—$CH(R_2)$—$COOCH_3$, and Boc-D-4-chloro-2-methyl-Phe-OH as Q-COOH. It was tested as described above with the results shown. The mass was analyzed as 543.4 (M+H).

| MC1-R | MC3-R | MC4-R | MC5-R |
|---|---|---|---|
| Inhibition at 1 μM | | | |
| 3 | 34 | 96 | 36 |
| Ki (nM) | | | |
| 462 | 398 | 3 | 774 |

In a CAMP assay for determination of agonist/antagonist status, it was determined that the compound was a partial agonist as to MC1-R and MC3-R, and an agonist as to MC4-R and MC5-R.

In rat model IV penile erection induction experiments at doses ranging from 0.3 to 30 μg/Kg, 0.5 to 0.7 mean penile erections per rat were observed.

EXAMPLE 46

N-{1(R)-(2,4-Dimethyl-benzyl)-2-[2(S)-(3-guanidino-propyl)-5(R)-methyl-4-(2-naphthalen-2-yl-acetyl)-piperazin-1-yl]-2-oxo-ethyl}-acetamide The following compound was synthesized by the method of Scheme 7. The compound of Example 44 was treated with the method of Example 36 to introduce an acetyl group at the amino group of D-2,4-dimethyl-Phe. It was tested as described above with the results shown. The mass was analyzed as 585.4 (M+H).

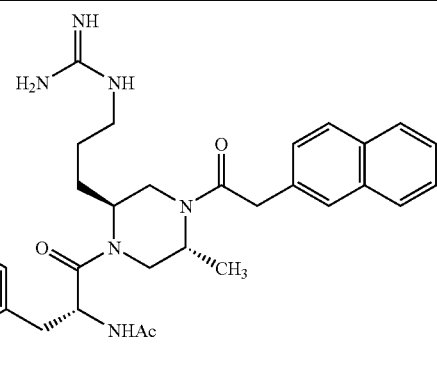

| MC1-R | MC3-R | MC4-R | MC5-R |
|---|---|---|---|
| Ki (nM) | | | |
| 1883 | 232 | 11 | 250 |

In a cAMP assay using MC1-R, MC3-R, MC4-R and MC5-R, at 1 μM concentrations the compound of Example 46 exhibited no intrinsic activity at MC1-R, MC3-R and MC5-R, and was a partial agonist at MC4-R.

In rat model penile erection induction experiments at doses ranging from 0.3 to 30 μg/Kg, no penile erection response was observed.

EXAMPLE 47

2(S)-Amino-N-{1(R)-(2,4-dimethyl-benzyl)-2-[2(S)-(3-guanidino-propyl)-5(R)-methyl-4-(2-naphthalen-2-yl-acetyl)-piperazin-1-yl]-2-oxo-ethyl}-3-(1H-imidazol-4-yl)-propionamide The following compound was synthesized by the method of Scheme 7, where after introduction of the 2,4 dimethyl-Phe derivative to the compound, a His derivative was attached at the N-terminus by methods similar to those described for the conversion of 5-7 to 5-8. It was tested as described above with the results shown. The mass was analyzed as 680.3 (M+H).

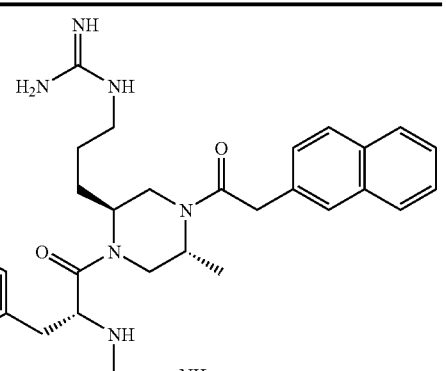

| MC1-R | MC3-R | MC4-R | MC5-R |
|---|---|---|---|
| Inhibition at 1 μM | | | |
| 93 | 72 | 97 | 50 |

EXAMPLE 48

N-{3-[1-[2(R)-Amino-3-(2,4-dimethyl-phenyl)-propionyl]-6(R)-methyl-4-(2-naphthalen-2-yl-acetyl)-piperazin-3(S)-yl]-propyl}-guanidine The following compound was synthesized by the method of Scheme 7 using 2-naphthyl acetic acid as Q-COOH, L-Orn (Boc) methyl ester as $NH_2$—$CH(R_2)$—$COOCH_3$, and Boc-D-2,4-di-methyl-Phe-OH as J-COOH. It was tested as described above with the results shown. The mass was analyzed as 543.2 (M+H).

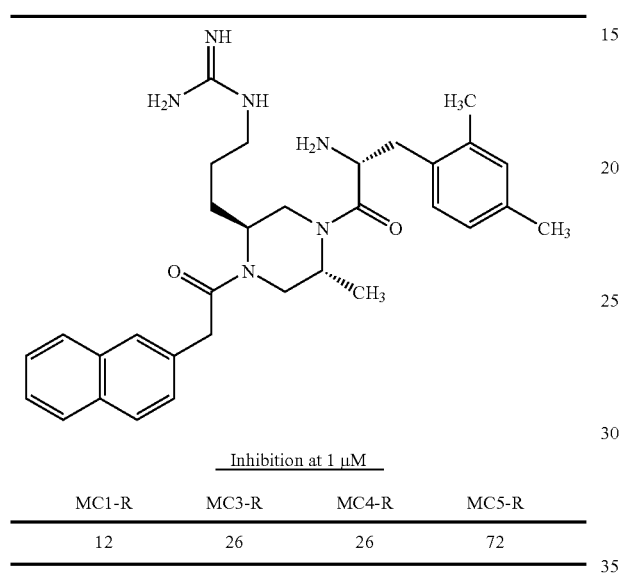

| Inhibition at 1 µM | | | |
|---|---|---|---|
| MC1-R | MC3-R | MC4-R | MC5-R |
| 12 | 26 | 26 | 72 |

EXAMPLE 49

N-[2-[4-[2(R)-Acetylamino-3-(4-chloro-phenyl)-propionyl]-2(S),5(S)-bis-(3-guanidino-propyl)-piperazin-1-yl]-1(R)-(4-chloro-benzyl)-2-oxo-ethyl]-acetamide The following compound is synthesized by the method of Scheme 9 using D-4-Cl-Phe as Q-COOH, and an acetyl group is attached to the amino group of D-4-Cl-Phe by conventional means, such as reaction of the compound with Ac-OSu in DMF.

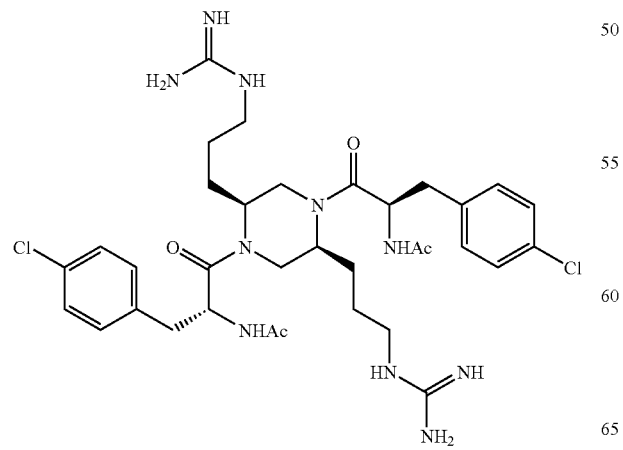

EXAMPLE 50

N-{3-[1-[2(R)-Amino-3-(4-chloro-phenyl)-propionyl]-5(R)-methyl-4-(2-naphthalen-2-yl-ethyl)-3-oxo-piperazin-2(S)-yl]-propyl}-guanidine The compound is synthesized by the method of Scheme 10 using 2-naphthyl acetic acid as J-COOH that is reacted with an aminopropanol derivative to obtain 10-1. D-4-Cl-Phe is employed as Q-COOH.

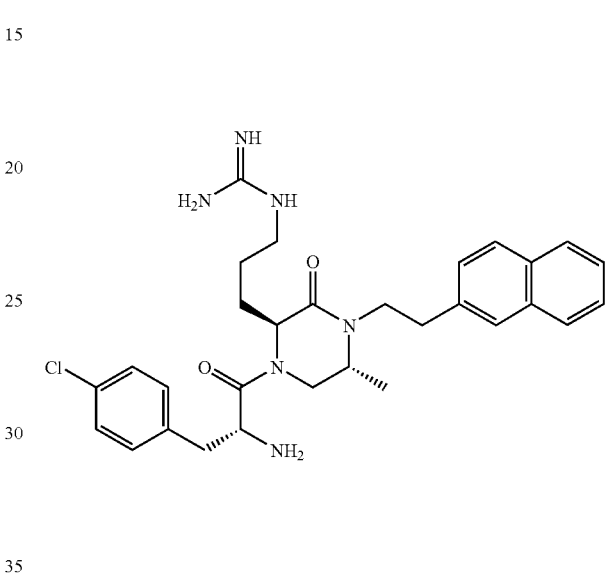

EXAMPLE 51

N-(3-{1-[2(R)-Amino-3-(4-chloro-phenyl)-propionyl]-5(R)-methyl-3-oxo-4-phenethyl-piperazin-2(S)-yl}-propyl)-guanidine The following compound is synthesized by the method of Example 48 using phenyl acetic acid as J-COOH.

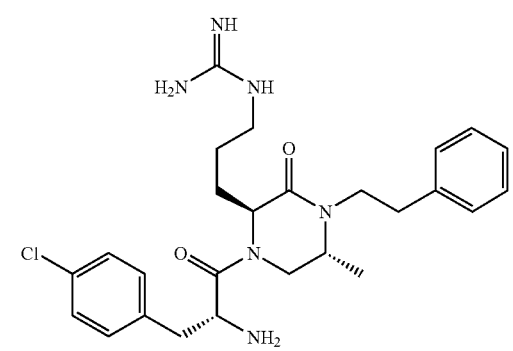

EXAMPLE 52

N-(3-{1-[2(R)-Amino-3-(4-chloro-phenyl)-propionyl]-4-[2-(1H-indol-3-yl)-ethyl]-5(R)-methyl-3-oxo-piperazin-2(S)-yl}-propyl)-guanidine The following compound is synthesized by the method of Example 48 using 3-indole acetic acid as J-COOH.

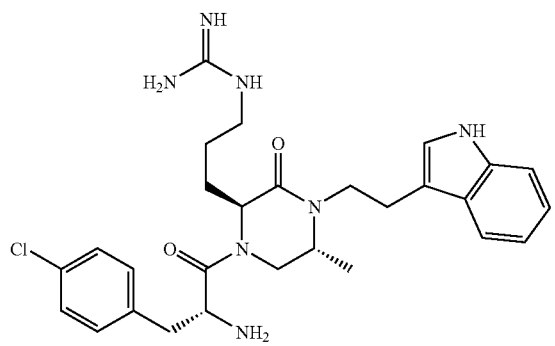

EXAMPLE 53

N-{3-[1-(2(R)-Amino-3-naphthalen-2-yl-propionyl)-5(R)-methyl-4-(2-naphthalen-2yl-ethyl)-3-oxo-piperazin-2(S)-yl]-propyl}-guanidine The following compound is synthesized by the method of Example 48 using 2-Nal amino acid as Q-COOH.

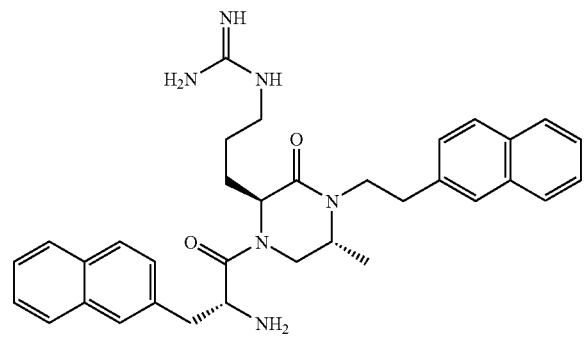

EXAMPLE 54

2(S)-Amino-N-{1 (R)-(4-chloro-benzyl)-2-[2(S)-(3-guanidino-propyl)-5(R)-methyl-4-(2-naphthalen-2-yl-ethyl)-3-oxo-piperazin-1-yl]-2-oxo-ethyl}-3-(1H-imidazol-4-yl)-propionamide The following compound is synthesized by the method of Example 48 where after introduction of D-4-Cl-Phe to the compound, a His derivative is attached at the N-terminus by methods similar to those described for the conversion of 10-4 to 10-5.

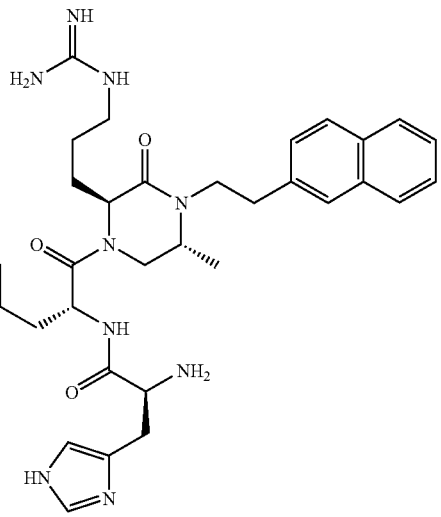

EXAMPLE 55

2(S)-Amino-N-{1(R)-(2,4-dimethyl-benzyl)-2-[2(S)-(3-guanidino-propyl)-5(R)-methyl-4-(2-naphthalen-2-yl-ethyl)-piperazin-1-yl]-2-oxo-ethyl}-3-(1H-imidazol-4-yl)-propionamide The following compound is synthesized by the method of Scheme 5 where after introduction of D-2,4 dimethyl-Phe to the compound, a His derivative is attached at the N-terminus by methods similar to those described for the conversion of 5-7 to 5-8.

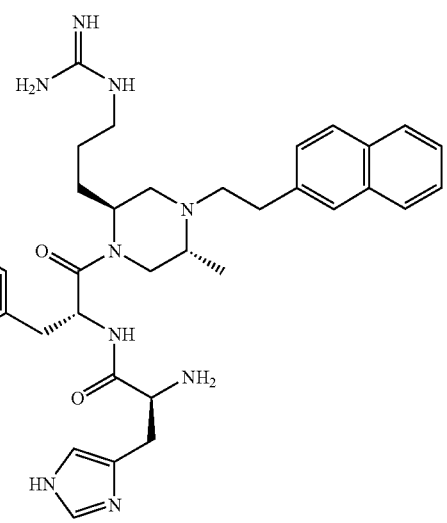

EXAMPLE 56

N-{3-[1-[2(R)-(PEG-Amino)-3-(4-chloro-phenyl)-propionyl]-5(R)-methyl-4-(2-naphthalen-2-yl-ethyl)-3-oxo-piperazin-2(S)-yl]-propyl}-guanidine The following compound is synthesized by the method of example 48 where after introduction of D-4-chloro-Phe to the compound, a polyethylene glycol (FW 100-10000) carboxylic acid derivative is attached at the N-terminus by methods similar to those described for the conversion of 10-4 to 10-5.

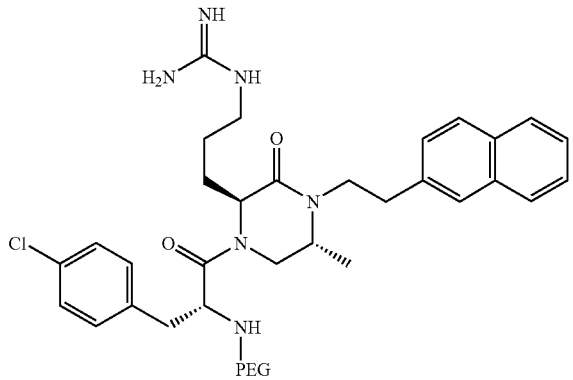

EXAMPLE 57

N-{3-[1-[2(R)-(PEG-Amino)-3-(4-chloro-phenyl)-propionyl]-5(R)-methyl-4-(2-naphthalen-2-yl-ethyl)-3-piperazin-2(S)-yl]-propyl}-guanidine The following compound is synthesized by the method of Scheme 5 where after introduction of D-4-Chloro-Phe to the compound, a polyethylene glycol (FW 100-10000) carboxylic acid derivative is attached at the N-terminus by methods similar to those described for the conversion of 5-7 to 5-8.

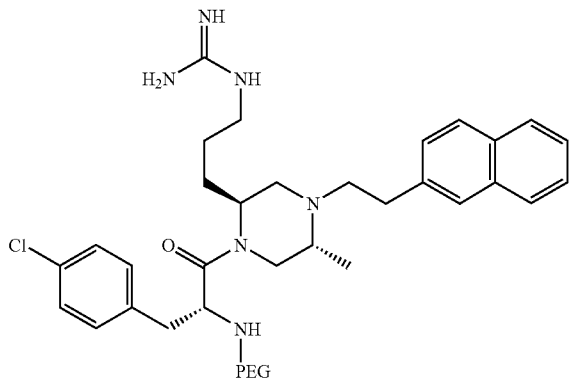

EXAMPLE 58

N-{3-[1-[2(R)-Amino-3-(2,4-dichloro-phenyl)-propionyl]-5(R),6(R)-dimethyl-4-(2-naphthalen-2-yl-ethyl)-piperazin-2(S)-yl]-propyl}-guanidine The following compound is synthesized by the methods of Scheme 3 and 4 where J-COOH is 2-naphthyl acetic acid and Q-COOH is D-2,4-dichoro-Phe.

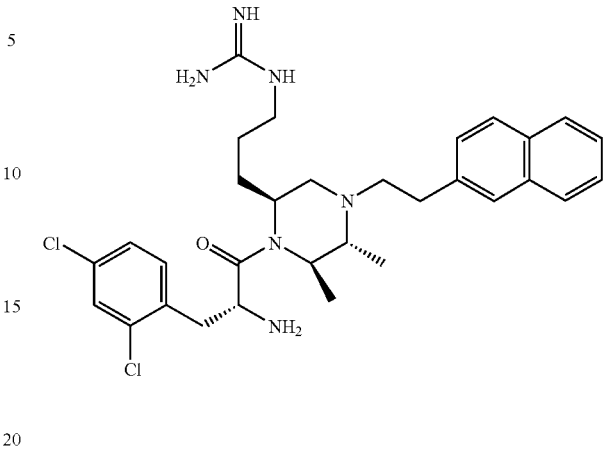

EXAMPLE 59

N-{3-[1-[2(R)-(PEG-Amino)-3-(4-chloro-phenyl)-propionyl]-5(R)-methyl-4-(2-naphthalen-2-yl-ethyl)-3-piperazin-2(S)-yl]-propyl}-guanidine The following compound is synthesized by the method of Scheme 5, wherein after introduction of D-4-chloro-Phe to the compound, a polyethylene glycol (FW 100-10000) carboxylic acid derivative is attached at the N-terminus by methods similar to those described for the conversion of 5-7 to 5-8.

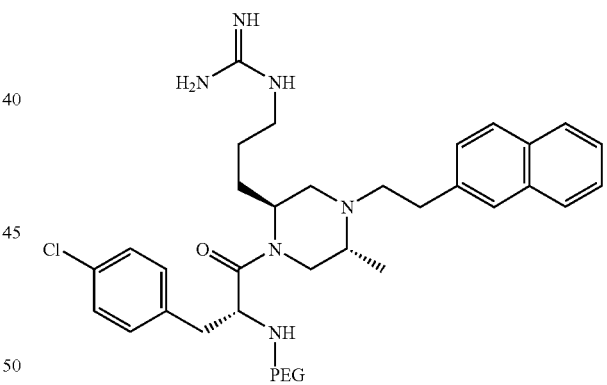

EXAMPLE 60

N-{2-[4-(2(R)-Amino-3-(2,4-dimethyl-phenyl)-2-yl-propionyl)-5(S)-(3-guanidino-propyl)-2(R)-methyl-piperazin-1-yl]-1(R)-benzyl-2-oxo-ethyl}-acetamide The following compound 1a synthesized by the method of Scheme 6 using Fmoc-D-Phe-OH as J-COOH, D-alanine methyl ester as $NH_2$—$CH(R_5)$—$COOCH_3$, and Boc-D-2,4-dimethyl-Phe-OH as Q-COOH. The J-COOH moiety is further modified by removal of the Fmoc group and reacting with acetic anhydride to form an acetamide moiety.

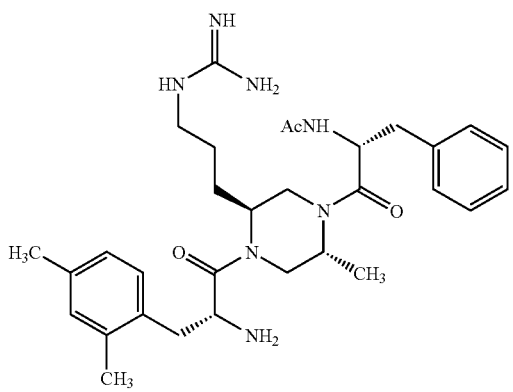

EXAMPLE 61

N-{2-[4-(2(R)-Amino-3-(2,4-dimethyl-phenyl)-2-yl-propionyl]-5(S)-(3-guanidino-propyl)-2(R)-methyl-piperazin-1-yl]-1(R)-(3-methyl-2,3-dihydro-1H-indol-3-ylmethyl)-2-oxo-ethyl]-acetamide The following compound is synthesized by the method of Scheme 6 using Fmoc-D-Trp(Boc)-OH as J-COOH, D-alanine methyl ester as $NH_2$—$CH(R_5)$—$COOCH_3$, and Boc-D-2,4-dimethyl-Phe-OH as Q-COOH. The J-COOH moiety is further modified by removal of the Fmoc group and reacting with acetic anhydride to form an acetamide moiety.

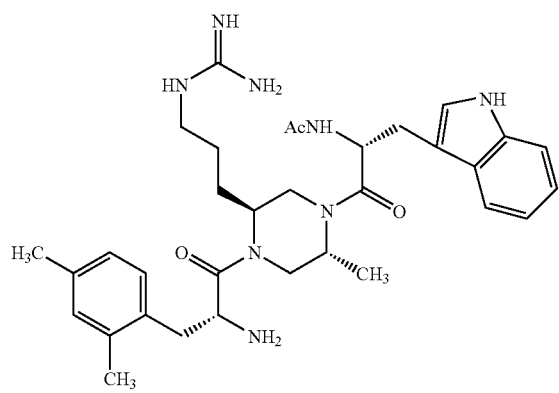

EXAMPLE 62

N-{1(R)-Benzyl-2-[4-[3-(2,4-dichloro-phenyl)-propionyl]-5(S)-(3-guanidino-propyl)-2(R)-methyl-piperazin-1-yl]-2-oxo-ethyl}-acetamide The following compound is synthesized by the method of Scheme 6 using Fmoc-D-Phe-OH as J-COOH, D-alanine methyl ester as $NH_2$—$CH(R_5)$—$COOCH_3$, and 3-(2,4-dichlorophenyl)-propionic acid as Q-COOH. The J-COOH moiety is further modified by removal of the Fmoc group and reacting with acetic anhydride to form an acetamide moiety.

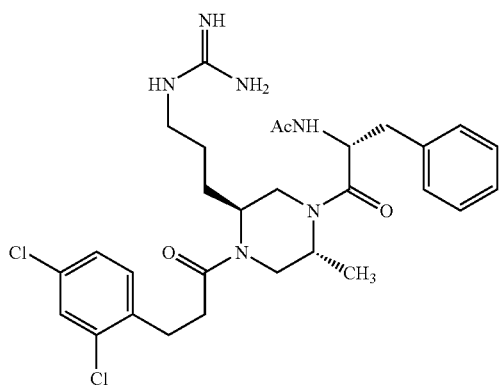

EXAMPLE 63

N-3-{1-[2(R)-Amino-3-(4-chloro-2-methyl-phenyl)-propionyl]-5(R)-methyl-4-phenylacetyl-piperazin-2(S)-yl}-propyl)-guanidine The following compound is synthesized by the method of Scheme 7 using phenylacetic acid as J-COOH, and Boc-D-4-chloro-2-methyl-Phe-OH as Q-COOH.

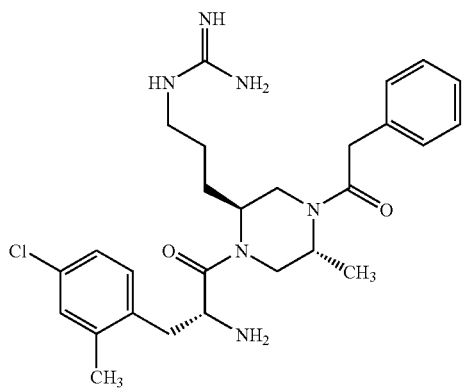

EXAMPLE 64

N-(3-{1-[2(R)-Amino-3-(4-chloro-2-methyl-phenyl)-propionyl]-5(R)-methyl-4-(3-phenyl-propionyl)-piperazin-2(S)-yl}-propyl)-guanidine The following compound is synthesized by the method of Scheme 7 using 3-phenylpropionic acid as J-COOH, and Boc-D-4-chloro-2-methyl-Phe-OH as Q-COOH.

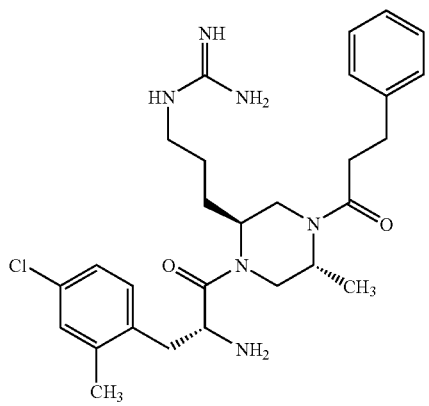

EXAMPLE 65

N-(3-{1-[2(R)-Amino-3-(4-chloro-2-methyl-phenyl)-propionyl]-5(R)-methyl-4-(4-phenyl-butyryl)-piperazin-2(S)-yl}-propyl)-guanidine The following compound is synthesized by the method of Scheme 7 using 4-phenylbutyric acid as J-COOH, and Boc-D-4-chloro-2-methyl-Phe-OH as Q-COOH.

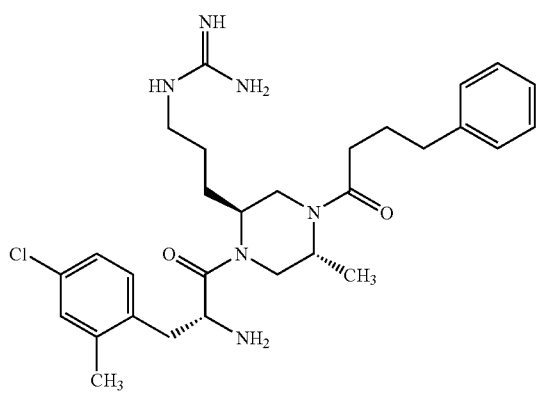

EXAMPLE 66

N-(3-{1-[3-(2,4-Dichloro-phenyl)-propionyl]-5(R)-methyl-4-phenylacetyl-piperazin-2(S)-yl}-propyl)-guanidine The following compound is synthesized by the method of Scheme 7 using phenylacetic acid as J-COOH and 3-(2,4-dichloro-phenyl)-propionic acid as Q-COOH.

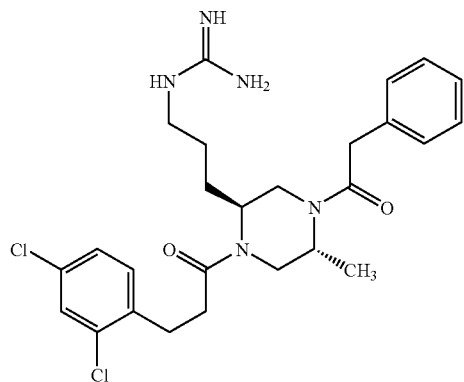

EXAMPLE 67

N-{3-[1-(2(R)-Amino-2-phenyl-acetyl)-5(R)-methyl-4-(3-phenyl-propionyl)-piperazin-2(S)-yl]-propyl}-guanidine The following compound is synthesized by the method of Scheme 7 using 3-phenylpropionic acid as J-COOH and Boc-D-phenylglycine as Q-COOH.

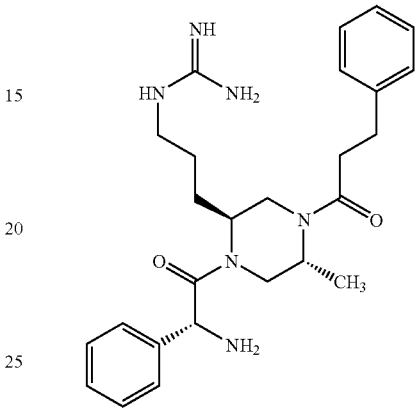

EXAMPLE 68

N-{3-[1-(2(R)-Amino-3-naphthalen-2-yl-propionyl)-5(R)-isobutyl-4-(2-naphthalen-2-yl-acetyl)-piperazin-2(S)-yl]-propyl}-guanidine The following compound is synthesized by the method of Scheme 7 using 2-Naphtylacetic acid as J-COOH, Fmoc-D-Leucine as Fmoc-NH—CH($R_5$)—OH and Boc-D-2-Nal-OH as Q-COOH.

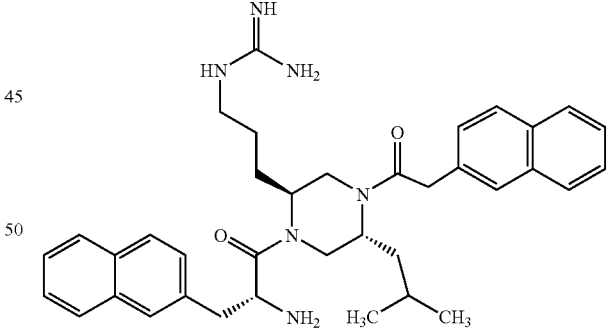

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound having the formula of structure I:

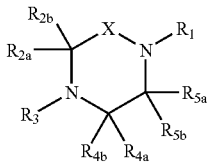

or an enantiomer, stereoisomer or diastereoisomer thereof, or a pharmaceutically acceptable salt thereof,
wherein
X is $CH_2$;
$R_1$ is $-L_1$-J;
one of $R_{2a}$ and $R_{2b}$ is $-L_2$-W and the remaining of $R_{2a}$ and $R_{2b}$ is hydrogen;
$R_3$ is $-L_3$-Q;
$L_1$ is a linker unit selected from the group consisting of $-(CH_2)_2-$, $-(CH_2)_3-$, $-(CH_2)_y-C(=O)-$, $-C(=O)-(CH_2)_y-$ and $-C(=O)-$;
J is a substituted or unsubstituted ring structure selected from the group consisting of

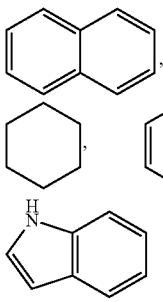 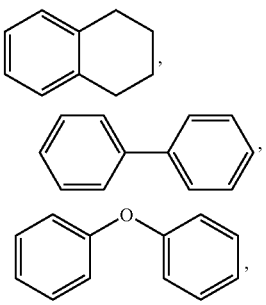

wherein, when substituted, J is substituted with one or more ring substituents independently selected from the group consisting of hydroxyl, halogen, sulfonamide, alkyl or aryl groups attached directly or through an ether linkage;
$L_2$ is $-(CH_2)_y-$;
W is $-NH-C(=NH)-NH_2$;
$L_3$ is a linker unit selected from the group consisting of
$-(CH_2)_y-CH(NR_{6a}R_{6b})-(CH_2)_y-$, $-(CH_2)_y-C(=O)-CH(NR_{6a}R_{6b})-(CH_2)_y-$, $-(CH_2)_y-C(=O)-$, $-(CH_2)_y-CH(CH_3)-C(=O)-$, $-C(=O)-(CH_2)_y-C(=O)-$, $-C(=O)-CH(NR_{6a}R_{6b})-(CH_2)_y-$, $-C(=O)-(CH_2)_y-$, $-C(=O)-(CH_2)_y-CH(NR_{6a}R_{6b})-$, $-C(=O)-(CH_2)_y-CH(NR_{6a}R_{6b})-(CH_2)_y-$, $-C(=O)-(CH_2)_y-CH(NHR_{6a}R_{6b})-C(=O)-$ and $-C(=O)-$;
$R_{6a}$ and $R_{6b}$ are each hydrogen;
Q is

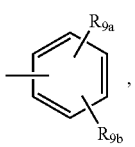

wherein $R_{9a}$ and $R_{9b}$ are ring substituents, wherein one or both are present and are the same or different and are independently hydroxyl, halogen, alkyl, or aryl groups attached directly or through an ether linkage;
$R_{5a}$ is a $C_1$ to $C_6$ aliphatic linear or branched chain;
$R_{5b}$ is hydrogen; and
each of $R_{4a}$ and $R_{4b}$ is hydrogen; and
y is at each occurrence independently from 1 to 6, provided that where any linker unit includes two y index values, the total of such y index values is from 2 to 6.

2. The compound of claim 1 wherein for $L_2$, y is from 1 to 4.

3. The compound of claim 1 wherein at least one Of $R_{9a}$ and $R_{9b}$ is selected from the group consisting of $-CH_3$ and $-OCH_3$.

4. The compound of claim 1 wherein at least one of $R_{9a}$ and $R_{9b}$ is selected from the group consisting of $-Cl$ and $-CF_3$.

5. The compound of claim 1 wherein $R_{5a}$ is selected from the group consisting of methyl and isobutyl.

6. The compound of claim 1 wherein
J is selected from the group consisting of naphthyl, phenyl, substituted phenyl, indole and substituted indole;
$L_2$ is $(CH_2)_3$;
$L_3$ is selected from the group consisting of $-C(=O)-(C-NR_{6a}R_{6b})-(CH_2)_y-$, $-C(=O)-(CH_2)_y-$ and $-(CH_2)_y-(C-NR_{6a}R_{6b})-(CH_2)_y-$; and
is methyl or isobutyl.

7. The compound of claim 1 and pharmaceutically acceptable salts thereof selected from the group consisting of:
N-{3-[1-[2(R)-Amino-3-(2,4-dichloro-phenyl)-propionyl]-5(R)-methyl-4-(2 naphthalen-2-yl-ethyl)-piperazin-2(S)-yl]-propyl}-guanidine;
N-{3-[1-[2(R)-Amino-3-(2,4-dichloro-phenyl)-propionyl]-5(S)-methyl-4-(2-naphthalen-2-yl-ethyl)-piperazin-2(S)-yl]-propyl}-guanidine;
N-{3-[1-[2(R)-Amino-3-(2-chloro-4-methyl-phenyl)-propionyl]-5(R)-methyl-4-(2-naphthalen-2-yl-ethyl)-piperazin-2(S)-yl]-propyl}-guanidine;
N-{3-[1-[2(R)-Amino-3-(4-chloro-2-methyl-phenyl)-propionyl]-5(R)-methyl-4-(2-naphthalen-2-yl-ethyl)-piperazin-2(S)-yl]-propyl}-guanidine;
N-{3-[1-[2(R)-Amino-3-(2,4-dichloro-phenyl)-propionyl]-5(S)-isobutyl-4-(2-naphthalen-2-yl-ethyl)-piperazin-2(S)-yl]-propyl}-guanidine;
N-{3-[1-[2(R)-Amino-3-(2,4-dichloro-phenyl)-propionyl]-5(R)-isobutyl-4-(2-naphthalen-2-yl-ethyl)-piperazin-2(S)-yl]-propyl}-guanidine;
N-{3-[1-[2(R)-Amino-3-(4-chloro-2-fluoro-phenyl)-propionyl]-5(R)-methyl-4-(2-naphthalen-2-yl-ethyl)-piperazin-2(S)-yl]-propyl}-guanidine;
N-{3-[1-[2(R)-Amino-3-(2,4-dimethyl-phenyl)-propionyl]-5(R)-methyl-4-(2-naphthalen-2-yl-ethyl)-piperazin-2(S)-yl]-propyl}-guanidine;
N-{3-[1-[2(R)-Amino-3-(2-chloro-4-trifluoromethyl-phenyl)-propionyl]-5(R)-methyl-4-(2-naphthalen-2-yl-ethyl)-piperazin-2(S)-yl]-propyl}-guanidine;
N-{3-[1-[2(R)-Amino-3-(4-chloro-phenyl)-propionyl]-5(R)-methyl-4-(2-naphthalen-2-yl-ethyl)-piperazin-2(S)-yl]-propyl}-guanidine;
N-{3-[1-[2(R)-Amino-3-(3,4-dichloro-phenyl)-propionyl]-5(R)-methyl-4-(2-naphthalen-2-yl-ethyl)-piperazin-2(S)-yl]-propyl}-guanidine;
N-{3-[1-[2(R)-Amino-3-(2,4-dimethyl-phenyl)-propionyl]-5(R)-methyl-4-(2-naphthalen-2-yl-methyl)-piperazin-2(S)-yl]-propyl}-guanidine;

N-(3-{1-(2(R)-Amino-(4-chloro-phenyl)-propionyl)-5(R)-methyl-4-[2-(1H-indol-3-yl)-ethyl]-piperazin-2(S)-yl}-propyl)-guanidine;

N-(3-{1-(2(R)-Amino-(4-chloro-2-methyl-phenyl)-propionyl)-5(R)-methyl-4-[2-(1H-indol-3-yl)-ethyl]-piperazin-2(S)-yl}-propyl)-guanidine;

N-{3-[1-[2(R)-Amino-3-(phenyl)-propionyl]-5(R)-methyl-4-(2-naphthalen-2-yl-ethyl)-piperazin-2(S)-yl]-propyl}-guanidine;

N-{3-[1-[2(R)-Amino-3-(4-methyl-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(4-methoxy-phenyl)-propionyl]-5(R)-methyl-4-(2-naphthalen-2-yl-ethyl)-piperazin-2(S)-yl]-propyl}-guanidine;

N-{3-[1-[2(R)-Amino-3-(2,4-dimethyl-phenyl)-propionyl]-5(R)-methyl-4-(2-naphthalen-2-yl-acetyl)-piperazin-2(S)-yl]-propyl}-guanidine;

N-{3-[1-[2(R)-Amino-3-(4-chloro-2-dimethyl-phenyl)-propionyl]-5(R)-methyl-4-(2-naphthalen-2-yl-acetyl)-piperazin-2(S)-yl]-propyl}-guanidine;

N-(3-{1-[2(R)-Amino-3-(4-chloro-2-methyl-phenyl)-propionyl]-5(R)-methyl-4-phenylacetyl-piperazin-2(S)-yl}-propyl)-guanidine;

N-(3-{1-[2(R)-Amino-3-(4-chloro-2-methyl-phenyl)-propionyl]-5(R)-methyl-4-(3-phenyl-propionyl)-piperazin-2(S)-yl}-propyl)-guanidine;

N-(3-{1-[2(R)-Amino-3-(4-chloro-2-methyl-phenyl)-propionyl]-5(R)-methyl-4-(4-phenyl-butyryl)-piperazin-2(S)-yl}-propyl)-guanidine;

N-(3-{1-[3-(2,4-Dichloro-phenyl)-propionyl]-5(R)-methyl-4-phenylacetyl-piperazin-2(S)-yl}-propyl)-guanidine; and N-{3-[1-(2(R)-Amino-2-phenyl-acetyl)-5(R)-methyl-4-(3-phenyl-propionyl)-piperazin-2(S)-yl]-propyl}-guanidine.

8. The compound of claim 1 wherein $R_{5a}$ is an (R)-configuration $C_1$ to $C_6$ aliphatic linear or branched chain.

9. The compound of claim 1 wherein $R_{5a}$ is (R)-methyl or (R)-isobutyl.

10. The compound of claim 8 wherein $L_1$ is selected from the group consisting of —$(CH_2)_2$— and —$(CH_2)_3$—.

11. A pharmaceutical composition, comprising a compound of any one of claims 1, 7 and 8 or a pharmaceutically acceptable salt thereof and a pharmaceutically acceptable carrier.

12. A method of treating obesity or cachexia in a mammal, comprising administering to the mammal a therapeutically effective amount of a pharmaceutical composition of claim 11.

13. The compound of claim 1 wherein $R_{5a}$ is an (R)-configuration $C_1$ to $C_6$ aliphatic linear or branched chain and wherein $L_1$ is selected from the group consisting of —C(=O)—$CH_2$—, —C(=O)—$(CH_2)_2$— and —C(=O)—$(CH_2)_3$—.

14. The compound of claim 1 wherein $R_{5a}$ is (R)-methyl or (R)-isobutyl and wherein $L_1$ is selected from the group consisting of —C(=O)—$CH_2$—, —C(=O)—$(CH_2)_2$— and —C(=O)—$(CH_2)_3$—.

15. A method of treating obesity or cachexia in a mammal, comprising administering to the mammal a therapeutically effective amount of a compound of any one of claims 1, 7 and 8.

* * * * *